US011358953B2

United States Patent
Panarese et al.

(10) Patent No.: US 11,358,953 B2
(45) Date of Patent: *Jun. 14, 2022

(54) FUNCTIONALIZED PEPTIDES AS ANTIVIRAL AGENTS

(71) Applicant: ENANTA PHARMACEUTICALS, INC., Watertown, MA (US)

(72) Inventors: Joseph D. Panarese, Newton, MA (US); Dexter Davis, Watertown, MA (US); Nathaniel Thomas Kenton, Watertown, MA (US); Samuel Bartlett, Brighton, MA (US); Sean M. Rafferty, Watertown, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/522,176

(22) Filed: Nov. 9, 2021

(65) Prior Publication Data

US 2022/0073499 A1   Mar. 10, 2022

Related U.S. Application Data

(63) Continuation of application No. 17/506,981, filed on Oct. 21, 2021, which is a continuation of application No. 17/379,409, filed on Jul. 19, 2021.

(60) Provisional application No. 63/054,048, filed on Jul. 20, 2020.

(51) Int. Cl.
| | |
|---|---|
| *C07D 403/12* | (2006.01) |
| *C07D 403/14* | (2006.01) |
| *C07D 405/14* | (2006.01) |
| *C07D 401/14* | (2006.01) |
| *A61P 31/14* | (2006.01) |
| *C07K 5/078* | (2006.01) |
| *C07K 5/097* | (2006.01) |
| *A61K 38/00* | (2006.01) |

(52) U.S. Cl.
CPC ............ *C07D 403/14* (2013.01); *A61P 31/14* (2018.01); *C07D 401/14* (2013.01); *C07D 403/12* (2013.01); *C07D 405/14* (2013.01); *C07K 5/06165* (2013.01); *C07K 5/0823* (2013.01); *A61K 38/00* (2013.01)

(58) Field of Classification Search
CPC ... C07D 403/12; C07D 403/14; C07D 405/14
See application file for complete search history.

(56) References Cited

U.S. PATENT DOCUMENTS

| | | | |
|---|---|---|---|
| 9,290,757 B2 | 3/2016 | Madison | |
| 9,309,284 B2 | 4/2016 | Chang et al. | |
| 9,328,147 B2 | 5/2016 | Wu et al. | |
| 9,347,044 B2 | 5/2016 | Brown et al. | |
| 9,428,739 B2 | 8/2016 | Colt et al. | |
| 9,447,382 B2 | 9/2016 | Mack | |
| 9,474,759 B2 | 10/2016 | Chang et al. | |
| 9,512,443 B2 | 12/2016 | Richmond et al. | |
| 9,587,235 B2 | 3/2017 | Buechler et al. | |
| 9,591,858 B2 | 3/2017 | Valles et al. | |
| 9,688,978 B2 | 6/2017 | Buechler et al. | |
| 9,772,328 B2 | 9/2017 | Stein et al. | |
| 9,791,436 B2 | 10/2017 | Alexandrov et al. | |
| 9,828,342 B2 | 11/2017 | Home et al. | |
| 9,975,885 B2 | 5/2018 | St John et al. | |
| 10,017,463 B2 | 7/2018 | Hedstrom et al. | |
| 10,023,879 B2 | 7/2018 | Flynn et al. | |
| 10,093,915 B2 | 10/2018 | Wu et al. | |
| 10,130,701 B2 | 11/2018 | Bickerton et al. | |
| 10,196,444 B2 | 2/2019 | Jarjour et al. | |

(Continued)

FOREIGN PATENT DOCUMENTS

| | | |
|---|---|---|
| WO | 2004101742 A3 | 6/2005 |
| WO | 2005113580 A1 | 12/2005 |

(Continued)

OTHER PUBLICATIONS

U.S. Appl. No. 17/379,409, filed Jul. 19, 2021.

(Continued)

*Primary Examiner* — Brian E McDowell

(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, thereof:

(I)

which inhibit coronavirus replication activity. The invention further relates to pharmaceutical compositions comprising a compound of Formula (I) or a pharmaceutically acceptable slat thereof, and methods of treating or preventing a coronavirus infection in a subject in need thereof, comprising administering to the subject a therapeutically effective amount of a compound of Formula (I) or a pharmaceutically acceptable salt thereof.

10 Claims, No Drawings

(56) References Cited

U.S. PATENT DOCUMENTS

| | | | |
|---|---|---|---|
| 10,221,396 | B2 | 3/2019 | Brown et al. |
| 10,260,048 | B2 | 4/2019 | Mack |
| 10,383,929 | B2 | 8/2019 | Morgan et al. |
| 10,428,142 | B2 | 10/2019 | Jarjour et al. |
| 10,457,731 | B2 | 10/2019 | Jarjour et al. |
| 10,472,618 | B2 | 11/2019 | Wu et al. |
| 10,479,975 | B2 | 11/2019 | Friedman |
| 10,590,084 | B2 | 3/2020 | Buckman et al. |
| 10,624,960 | B2 | 4/2020 | Morgan et al. |
| 10,639,358 | B2 | 5/2020 | Morgan et al. |
| 10,639,359 | B2 | 5/2020 | Morgan et al. |
| 10,646,558 | B2 | 5/2020 | Morgan et al. |
| 10,711,260 | B2 | 7/2020 | Wu et al. |
| 10,774,343 | B2 | 9/2020 | Morgan et al. |
| 10,784,994 | B2 | 9/2020 | Yi et al. |
| 10,793,843 | B2 | 10/2020 | Jarjour et al. |
| 10,927,367 | B2 | 2/2021 | Jarjour et al. |
| 10,934,261 | B2 | 3/2021 | Buckman et al. |
| 10,934,575 | B2 | 3/2021 | Grosveld et al. |
| 10,954,529 | B2 | 3/2021 | Flynn et al. |
| 10,959,969 | B1 | 3/2021 | Johnson |
| 10,986,848 | B2 | 4/2021 | Holz-Schietinger et al. |
| 11,013,779 | B2 | 5/2021 | Chang et al. |
| 11,020,466 | B2 | 6/2021 | Morgan et al. |
| 11,021,513 | B2 | 6/2021 | Schinazi et al. |
| 11,033,600 | B2 | 6/2021 | Chang et al. |
| 11,045,546 | B1 | 6/2021 | Kelly et al. |
| 11,058,763 | B2 | 7/2021 | Zhang et al. |
| 11,058,779 | B2 | 7/2021 | Lu et al. |
| 11,072,787 | B2 | 7/2021 | Wu et al. |
| 11,124,497 | B1 | 9/2021 | Arnold et al. |
| 11,174,231 | B1 | 11/2021 | Arnold et al. |
| 11,207,370 | B2 | 12/2021 | Schinazi et al. |
| 2005/0143320 | A1 | 6/2005 | Yang et al. |
| 2006/0014821 | A1 | 1/2006 | He et al. |
| 2009/0137818 | A1 | 5/2009 | Hilgenfeld et al. |
| 2014/0243341 | A1 | 8/2014 | Chang et al. |
| 2021/0355111 | A1 | 11/2021 | Arnold et al. |

FOREIGN PATENT DOCUMENTS

| | | | |
|---|---|---|---|
| WO | 2006061714 | A3 | 8/2006 |
| WO | 2013049382 | A3 | 5/2013 |
| WO | 2013166319 | A1 | 11/2013 |
| WO | 2018042343 | A2 | 3/2018 |
| WO | 2021205296 | A1 | 10/2021 |
| WO | 2021206876 | A1 | 10/2021 |
| WO | 2021206877 | A1 | 10/2021 |
| WO | 2021207409 | A2 | 10/2021 |
| WO | 2021226546 | A1 | 11/2021 |
| WO | 2021250648 | A1 | 12/2021 |
| WO | 2021252491 | A1 | 12/2021 |
| WO | 2022020711 | A1 | 1/2022 |

OTHER PUBLICATIONS

U.S. Appl. No. 17/479,244, filed Sep. 20, 2021.
U.S. Appl. No. 17/479,248, filed Sep. 20, 2021.
U.S. Appl. No. 17/479,455, filed Sep. 20, 2021.
U.S. Appl. No. 17/479,530, filed Sep. 20, 2021.
U.S. Appl. No. 17/479,669, filed Sep. 20, 2021.
U.S. Appl. No. 17/506,981, filed Oct. 21, 2021.
Halford, B., "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.
Halford, B, "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.
Konno, S. et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, Jul. 27, 2021, pp. 1-14.
Lee., C. et al., "Structural Basis of Inhibition Specificities of 3C and 3C-like Proteases by Zinc-coordinating and Peptidomimetic Compounds", J. Biological Chem., vol. 284, No. 12, Mar. 20, 2009, 7646-7655.
Yang, S. et al., "Synthesis, Crystal Structure, Structure-Activity Relationships, and Antiviral Activity of a Potent SARS Coronavirus 3CL Protease Inhibitor", J. Med. Chem., vol. 49, Jul. 14, 2006, 4971-4980.
U.S. Appl. No. 63/067,669, filed Aug. 19, 2020.
U.S. Appl. No. 63/039,297, filed Jun. 15, 2020.
U.S. Appl. No. 63/036,866, filed Jun. 9, 2020.

FUNCTIONALIZED PEPTIDES AS ANTIVIRAL AGENTS

RELATED APPLICATIONS

This application is a continuation application of U.S. application Ser. No. 17/506,980, filed on Oct. 21, 2021, which is a continuation application of U.S. application Ser. No. 17/379,409, filed on Jul. 19, 2021, which claims the benefit of U.S. Provisional Application No. 63/054,048, filed on Jul. 20, 2020. The entire teachings of the above applications are incorporated herein by reference.

TECHNICAL FIELD

The invention relates to compounds and methods of inhibiting coronavirus replication activity by contacting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are family of single-stranded, positive-strand RNA viruses with viral envelopes, classified within the Nidovirales order. The coronavirus family comprises pathogens of many animal species, including humans, horses, cattle, pigs, birds, cats and monkeys, and have been known for more than 60 years. The isolation of the prototype murine coronavirus strain JHM, for example, was reported in 1949. Coronaviruses are common viruses that generally cause mild to moderate upper-respiratory tract illnesses in humans, and are named for the crown-like spikes on their envelope surface. There are four major sub-groups known as alpha, beta, gamma and delta coronaviruses, with the first coronaviruses identified in the mid-1960s. The coronaviruses known to infect humans include alpha coronaviruses 229E and NL63; and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS). People are commonly infected with human coronaviruses 229E, NL63, OC43 and HKU1, and symptoms usually include mild to moderate upper-respiratory tract illnesses of short duration, such as runny nose, cough, sore throat and fever. Occasionally human coronaviruses result in lower-respiratory tract illnesses, such as pneumonia, although this is more common in people with cardiopulmonary disease or compromised immune systems, or in the elderly. Transmission of the common human coronaviruses is not fully understood. However, it is likely that human coronaviruses spread from an infected person to others through the air by coughing and sneezing, and through close personal contact, such as touching or shaking hands. These viruses may also spread by touching contaminated objects or surfaces then touching the mouth, nose, or eyes.

Coronaviruses are enveloped, positive-sense, single-stranded RNA viruses. The genomic RNA of CoVs has a 5'-cap structure and 3'-poly-A tail, and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO2018042343, WO2018023054, WO2005113580, and WO2006061714).

More effective therapies for coronavirus infections are needed due to this high unmet clinical need. This invention describes the methods to prepare and methods for use of compounds that are believed to inhibit the coronavirus lifecycle. Compounds of this type might be used to treat coronavirus infections and decrease occurrence of disease complications such as organ failure or death.

There is a need in the art for novel therapeutic agents that treat, ameliorate or prevent coronavirus infection. Administration of these therapeutic agents to a coronavirus infected patient, either as monotherapy or in combination with other coronavirus treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

The present invention provides compounds represented by Formula (I), and pharmaceutically acceptable salts, N-oxides, esters and prodrugs thereof,

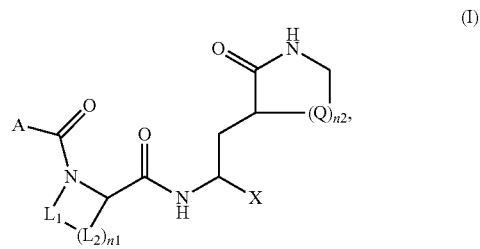

wherein:
A is selected from:
 1) Optionally substituted —$C_1$-$C_8$ alkyl;
 2) Optionally substituted —$C_3$-$C_{12}$ cycloalkyl;
 3) Optionally substituted 3- to 12-membered heterocycloalkyl;
 4) Optionally substituted aryl; and
 5) Optionally substituted heteroaryl;

$L_1$ is —C($R_{11}R_{12}$)—;
$L_2$ is —C($R_{11}R_{12}$)—;
n1 is 0, 1, 2, 3, or 4;
X is optionally substituted —$C_1$-$C_6$ alkyl, —CN, —C(O)$R_{15}$, —C(O)N$R_{13}R_{14}$, or —C(O)C(O)N$R_{13}R_{14}$;
Each Q is —C($R_{11}'R_{12}'$)—;
n2 is 0, 1, 2, 3 or 4; preferably n2 is not 0;
Each $R_{11}$, $R_{11}'$, $R_{12}$, and $R_{12}'$ is independently selected from:
  1) Hydrogen;
  2) Halogen;
  3) —O$R_{16}$;
  4) —S$R_{16}$;
  5) —N$R_{13}R_{14}$;
  6) —OC(O)N$R_{13}R_{14}$;
  7) Optionally substituted —$C_1$-$C_6$ alkyl;
  8) Optionally substituted —$C_3$-$C_8$ cycloalkyl;
  9) Optionally substituted 3- to 8-membered heterocycloalkyl;
  10) Optionally substituted aryl; and
  11) Optionally substituted heteroaryl;
  alternatively, $R_{11}$ and $R_{12}$ are taken together with the carbon atom to which they are attached to form an optionally substituted 3- to 8-membered carbocyclic or heterocyclic ring;
  alternatively, when n1 is not 0, two adjacent $R_{11}$ groups are taken together with the carbon atoms to which they are attached to form an optionally substituted 3- to 8-membered carbocyclic or heterocyclic ring;
  alternatively, n1 is 2, 3 or 4, and the $R_{11}$ groups on two non-adjacent carbon atoms are taken together with the carbon atoms to which they are attached to form an optionally substituted bridging moiety; in this embodiment,

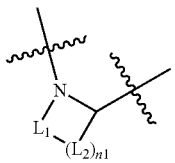

is preferably an optionally substituted 6-12-membered bridged heterocyclic ring system;
$R_{13}$ and $R_{14}$ are each independently selected from:
  1) Hydrogen;
  2) Optionally substituted —$C_1$-$C_6$ alkyl;
  3) Optionally substituted —$C_3$-$C_8$ cycloalkyl;
  4) Optionally substituted 3- to 8-membered heterocycloalkyl;
  5) Optionally substituted aryl;
  6) Optionally substituted arylalkyl;
  7) Optionally substituted heteroaryl;
  8) Optionally substituted heteroarylalkyl;
  9) —C(O)$R_{15}$;
  10) —S(O)$_2R_{16}$; and
  11) —NH$_2$;
  alternatively, $R_{13}$ and $R_{14}$ are taken together with the nitrogen atom to which they are attached to form an optionally substituted 3- to 8-membered heterocyclic ring.
$R_{15}$ is selected from:
  1) Hydrogen;
  2) Halogen;
  3) —OH;
  4) Optionally substituted —$C_1$-$C_6$ alkyl;
  5) Optionally substituted —$C_1$-$C_6$ alkoxy;
  6) Optionally substituted —$C_3$-$C_8$ cycloalkyl;
  7) Optionally substituted 3- to 8-membered heterocloalkyl;
  8) Optionally substituted aryl;
  9) Optionally substituted arylalkyl;
  10) Optionally substituted heteroaryl; and
  11) Optionally substituted heteroarylalkyl;
$R_{16}$ is selected from:
  1) Hydrogen;
  2) —OH;
  3) Optionally substituted —$C_1$-$C_6$ alkyl;
  4) Optionally substituted —$C_3$-$C_8$ cycloalkyl;
  5) Optionally substituted 3- to 8-membered heterocycloalkyl;
  6) Optionally substituted aryl;
  7) Optionally substituted arylalkyl;
  8) Optionally substituted heteroaryl, and
  9) Optionally substituted heteroarylalkyl.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), $R_{13}$ and $R_{14}$ are each independently selected from hydrogen; optionally substituted —$C_1$-$C_6$ alkyl; optionally substituted —$C_3$-$C_8$ cycloalkyl; optionally substituted 3- to 8-membered heterocycloalkyl; optionally substituted aryl; optionally substituted heteroaryl; —C(O)$R_{15}$; —S(O)$_2R_{16}$; and —NH$_2$; alternatively, $R_{13}$ and $R_{14}$ are taken together with the nitrogen atom to which they are attached to form an optionally substituted 3- to 8-membered heterocyclic ring; $R_{15}$ is selected from hydrogen; halogen; —OH; optionally substituted —$C_1$-$C_6$ alkyl; optionally substituted —$C_1$-$C_6$ alkoxy; optionally substituted —$C_3$-$C_8$ cycloalkyl; optionally substituted 3- to 8-membered heterocycloalkyl; optionally substituted aryl; and optionally substituted heteroaryl; and $R_{16}$ is selected from hydrogen; —OH; optionally substituted —$C_1$-$C_6$ alkyl; optionally substituted —$C_3$-$C_8$ cycloalkyl; optionally substituted 3- to 8-membered heterocycloalkyl; optionally substituted aryl; and optionally substituted heteroaryl.

In certain embodiments of the compounds of Formula (I), X is —CN.

In certain embodiments of the compounds of Formula (I), X is —C(O)CH$_2$OC(O)$R_{21}$, —C(O)CH$_2$C(O)$_2R_{21}$, —C(O)CH$_2$O$R_{21}$, or —C(O)CH$_2R_{22}$; $R_{21}$ is hydrogen, optionally substituted —$C_1$-$C_6$ alkyl, optionally substituted —$C_3$-$C_8$ cycloalkyl, optionally substituted 3- to 8-membered heterocycloalkyl, optionally substituted aryl, or optionally substituted heteroaryl; and $R_{22}$ is halogen, or —N$R_{13}R_{14}$.

In certain embodiments of the compounds of Formula (I), X is —C(O)C(O)NH$R_{21}$, and $R_{21}$ is as previously defined. Preferably, $R_{21}$ is optionally substituted benzyl, optionally substituted methyl, optionally substituted isopropyl, optionally substituted t-butyl, or optionally substituted cyclohexyl.

In certain embodiments of the compounds of Formula (I), X is —C(O)$R_{21}$, and $R_{21}$ is previously defined.

In certain embodiments of the compounds of Formula (I), X is —CH$R_{21}$OC(O)$R_{21}$, —CH$R_{21}$C(O)$_2R_{21}$, —CH$R_{21}$(O$R_{21}$), or —CH(O$R_{21}$)$_2$, and $R_{21}$ is previously defined.

In certain embodiments, X is selected from —CN, —C(O)H,

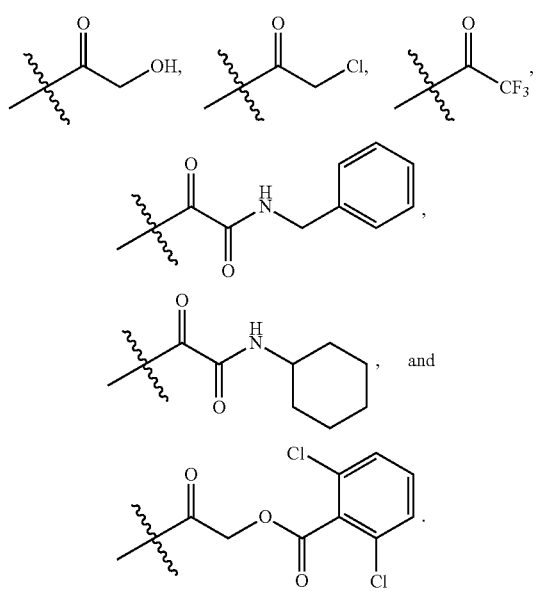
In preferred embodiments, X is —CN.
In certain embodiments of the compounds of Formula (I), A is derived from one of the following by removal of a hydrogen atom and is optionally substituted:
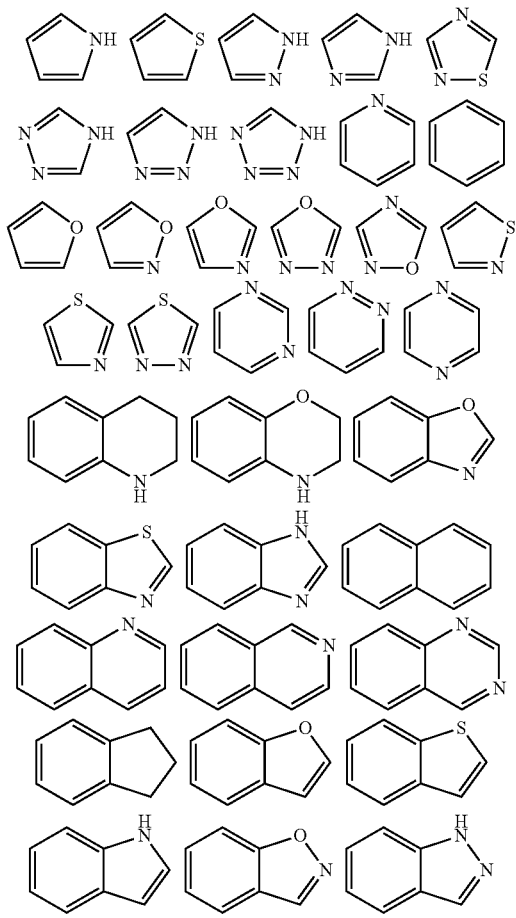
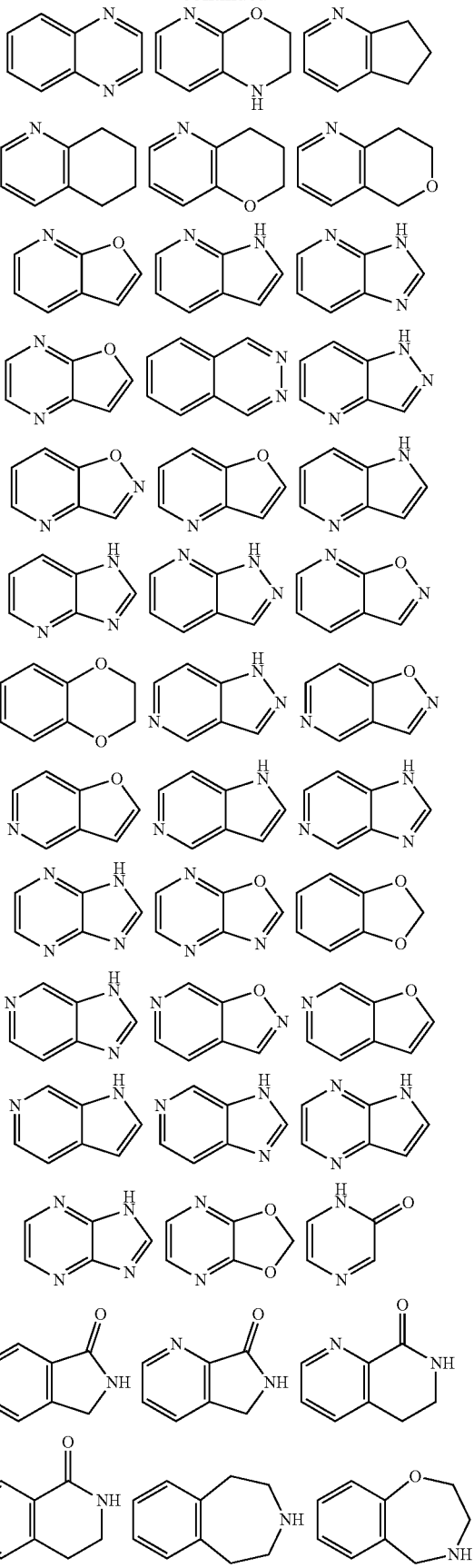

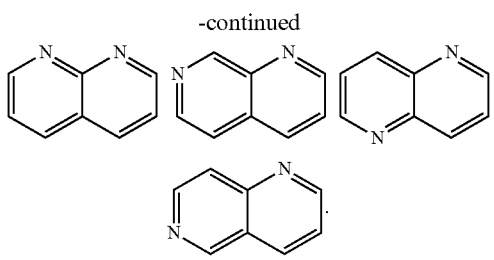

In certain embodiments of the compounds of Formula (I), A is selected from the following groups, and A is optionally substituted:

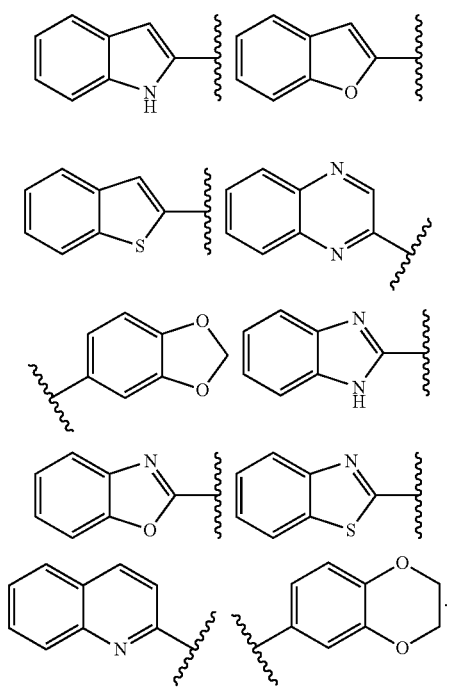

Preferably, A has 0, 1 or 2 substituents. Preferably the substituents are independently selected from fluoro, chloro, hydroxy, methoxy, fluoromethoxy, difluoromethoxy, and trifluoromethoxy.

In certain embodiments of the compounds of Formula (I), A is —$CH_2R_{23}$, and $R_{23}$ is —$NR_{13}R_{14}$, optionally substituted —$C_3$-$C_{12}$ cycloalkyl, optionally substituted 3- to 12-membered heterocycloalkyl, optionally substituted aryl, or optionally substituted heteroaryl.

In certain embodiments of the compounds of Formula (I), A is —$CR_{23}R_{24}R_{25}$, wherein $R_{24}$ is hydrogen, halogen, optionally substituted —$C_1$-$C_6$ alkyl, optionally substituted —$C_1$-$C_6$ alkoxy, optionally substituted —$C_3$-$C_{12}$ cycloalkyl, optionally substituted 3- to 12-membered heterocycloalkyl, optionally substituted aryl, optionally substituted arylalkyl, optionally substituted heteroaryl, or optionally substituted heteroarylalkyl; $R_{25}$ is hydrogen or halogen; and $R_{23}$ is as previously defined.

In certain embodiments of the compounds of Formula (I), A is —$C(NR_{13}R_{14})R_{24}R_{25}$, wherein $R_{13}$, $R_{14}$, $R_{24}$, and $R_{25}$ are as previously defined.

In certain embodiments of the compounds of Formula (I), A is

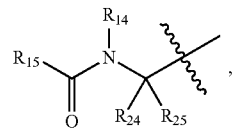

wherein $R_{14}$, $R_{15}$, $R_{24}$, and $R_{25}$ are as previously defined. In certain embodiments, $R_{14}$ and $R_{25}$ are hydrogen and $R_{24}$ is $C_1$-$C_6$-alkyl, preferably t-butyl. $R_{15}$ is preferably benzyl, $C_1$-$C_6$-alkyl, or $C_3$-$C_8$-cycloalkyl.

In certain embodiments of the compounds of Formula (I), at least one Q is —$CH_2$—. In certain embodiments of the compounds of Formula (I) all Qs are —$CH_2$—.

In certain embodiments, the compound of Formula (I) is represented by one of Formulae (II-1)~(11-2), or a pharmaceutically acceptable salt thereof:

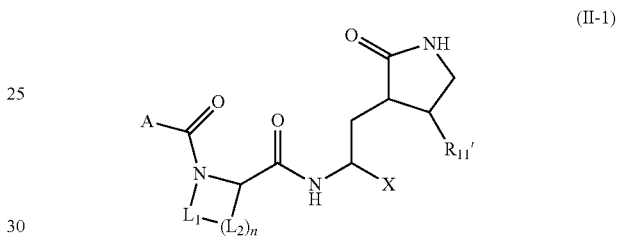

(II-1)

(II-2)

wherein A, $L_1$, $L_2$, n, $R_{11}'$, and X are as previously defined.

In certain embodiments, the compound of Formula (I) is represented by one of Formulae (II-1a)~(II-2a), or a pharmaceutically acceptable salt thereof:

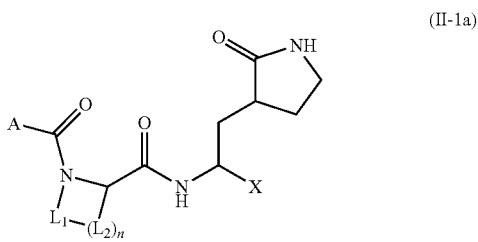

(II-1a)

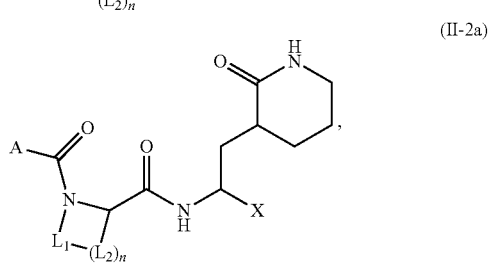

(II-2a)

wherein A, $L_1$, $L_2$, n, and X are as previously defined.

In certain embodiments, the compound of Formula (I) is represented by one of Formulae (III-1)~(III-2), or a pharmaceutically acceptable salt thereof:

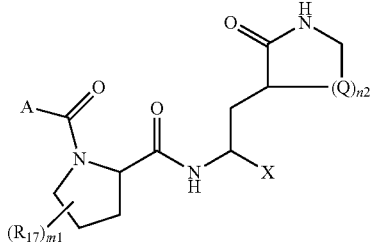
(III-1)

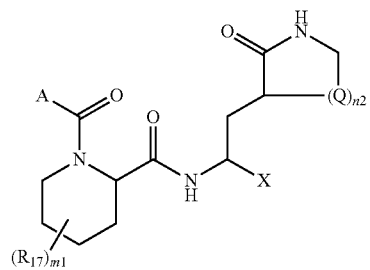
(III-2)

wherein A, Q, n2, and X are as previously defined; $R_{17}$ is halogen, —$OR_{16}$, —$SR_{16}$; —$NR_{13}R_{14}$; —$OC(O)NR_{13}R_{14}$; optionally substituted —$C_1$-$C_6$ alkyl; optionally substituted —$C_3$-$C_8$ cycloalkyl; optionally substituted 3- to 8-membered heterocycloalkyl; optionally substituted aryl; or optionally substituted heteroaryl; m1 is 0, 1, 2 or 3, and m2 is 0, 1, 2, 3, or 4. Preferably, m1 is 0 and m2 is 0.

In certain embodiments, the compound of Formula (I) is represented by one of Formulae (IV-1)~(IV-4), or a pharmaceutically acceptable salt thereof:

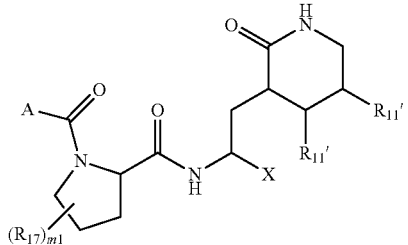
(IV-1)

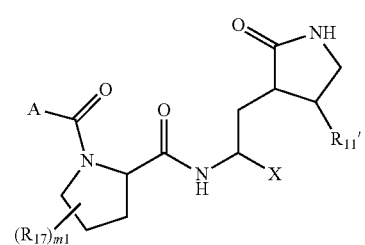
(IV-2)

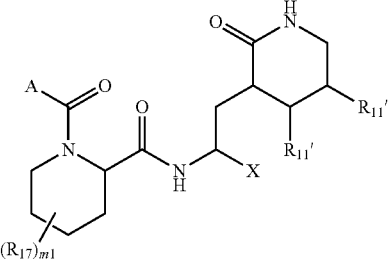
(IV-3)

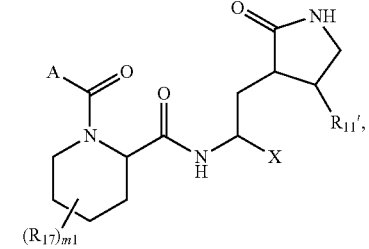
(IV-4)

wherein A, $R_{17}$, $R_{11}'$, m1, m2, and X are as previously defined.

In certain embodiments, the compound of Formula (I) is represented by one of Formulae (IV-1a)~(IV-4a), or a pharmaceutically acceptable salt thereof:

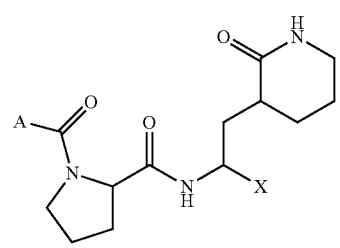
(IV-1a)

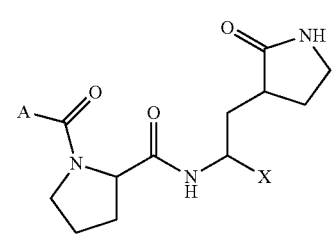
(IV-2a)

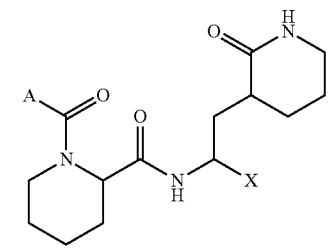
(IV-3a)

-continued

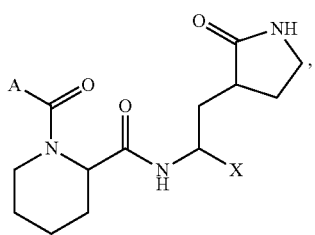
(IV-4a)

wherein A and X are as previously defined.

In certain embodiments, the compound of Formula (I) is represented by one of Formulae (V-1)~(V-4), or a pharmaceutically acceptable salt thereof:

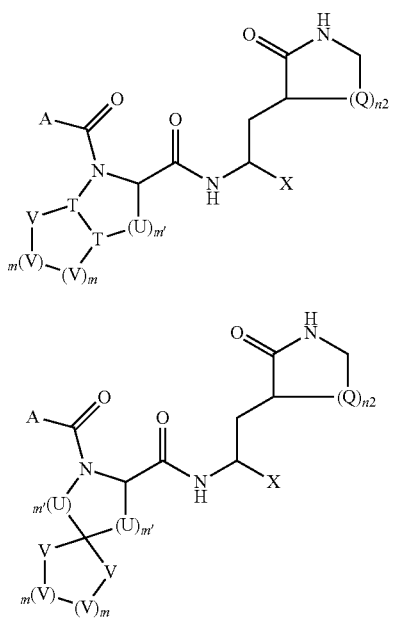
(V-1)

(V-2)

(V-3)

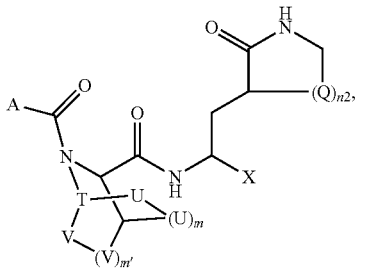
(V-4)

wherein each T is $CR_{11}$; each U is $-C(R_{11}R_{12})-$; each V is $-O-$, $-S-$, $-C(R_{11}R_{12})-$, or $-N(R_{13}R_{14})-$; m is 0, 1 or 2; m' is 0, 1, 2, or 3; and A, Q, n2, $R_{11}$, $R_{12}$, $R_{13}$, $R_{14}$, and X are as previously defined.

In certain embodiments, the compound of Formula (I) is represented by one of Formulae (VI-1)~(VI-6), or a pharmaceutically acceptable salt thereof:

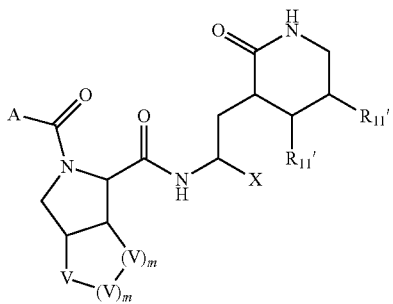
(VI-1)

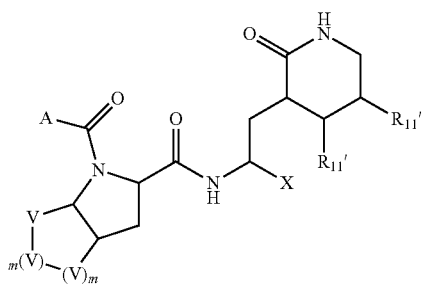
(VI-2)

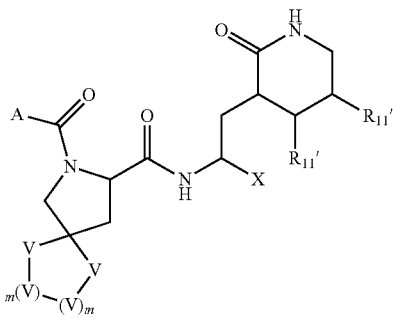
(VI-5)

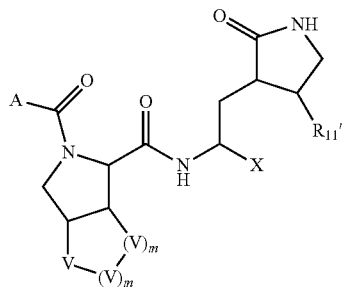
(VI-3)

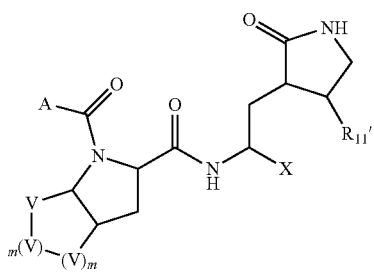
(VI-4)

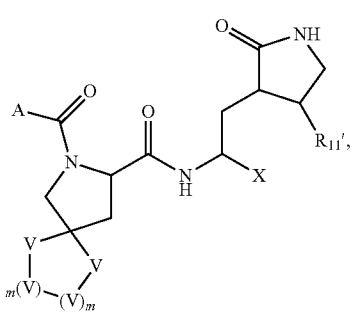
(VI-6)

wherein A, $R_{11}$, V, m, and X are as previously defined.

In certain embodiments, the compound of Formula (I) is represented by one of Formulae (VI-1a)~(VI-8a), or a pharmaceutically acceptable salt thereof:

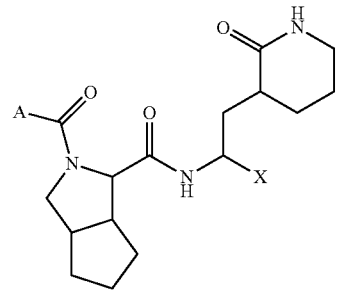
(VI-1a)

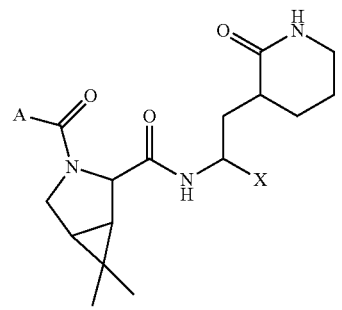
(VI-2a)

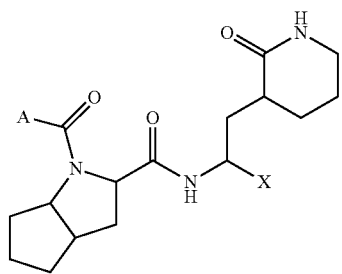
(VI-3a)

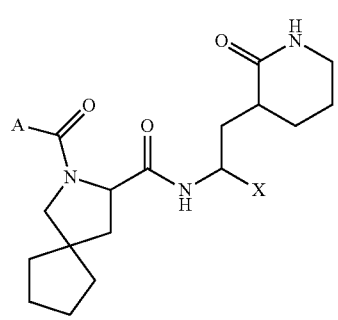
(VI-4a)

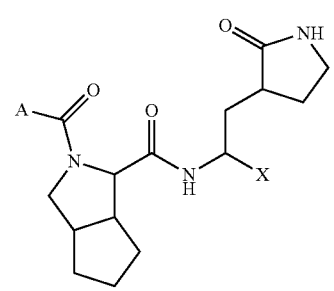
(VI-5a)

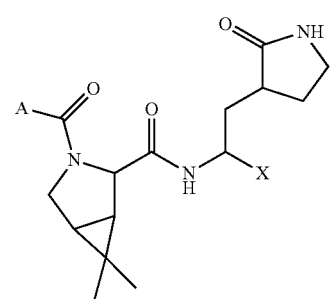
(VI-6a)

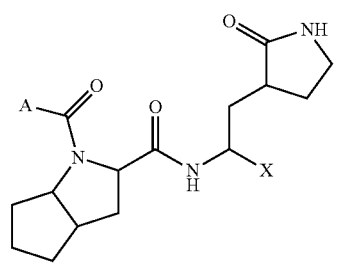
(VI-7a)

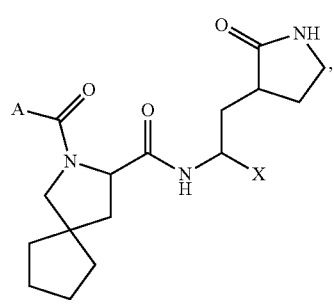
(VI-8a)

wherein A and X are as previously defined.

In certain embodiments, the compound of Formula (I) is represented by one of Formulae (VII-1)~(VII-6), or a pharmaceutically acceptable salt thereof:

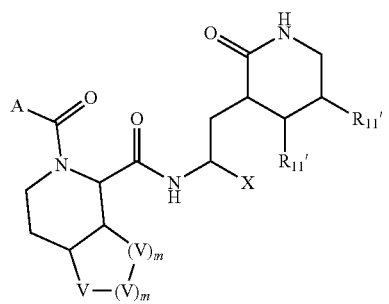
(VII-1)
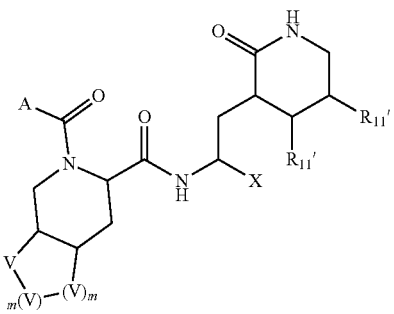
(VII-2)
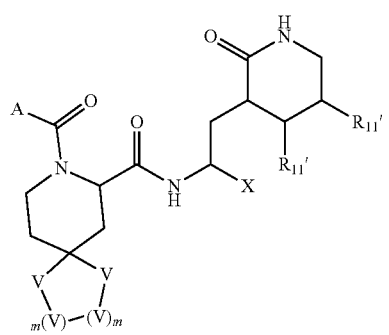
(VII-5)
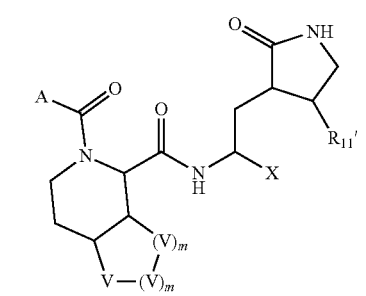
(VII-3)
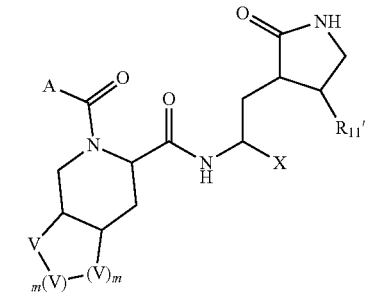
(VII-4)
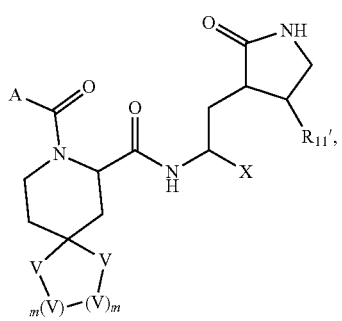
(VII-6)
wherein A, $R_{11}'$, V, m, and X are as previously defined.
In certain embodiments, the compound of Formula (I) is represented by one of Formulae (VII-1a)~(VII-6a), or a pharmaceutically acceptable salt thereof:
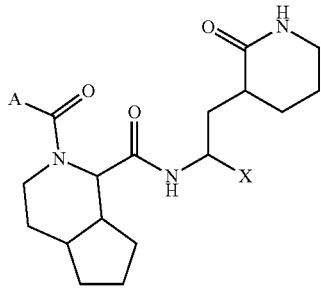
(VII-1a)
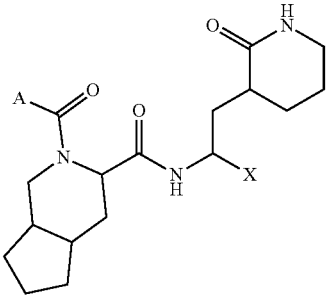
(VII-2a)
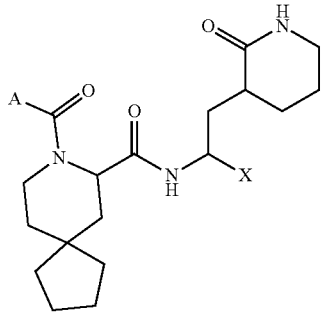
(VII-3a)

(VII-4a)
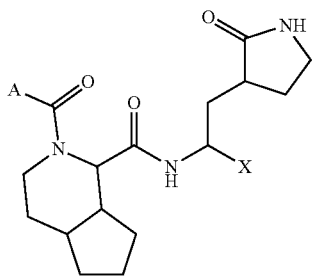

(VII-5a)
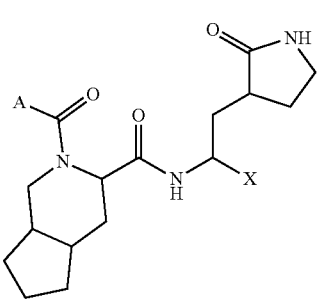

(VII-6a)
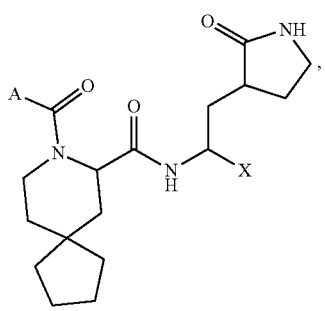

wherein A and X are as previously defined.

In certain embodiments, the present invention relates to compounds of Formulae (VI-1)~(VI-4), or Formulae (VII-1)~(VII-4), and pharmaceutically acceptable salts thereof, wherein

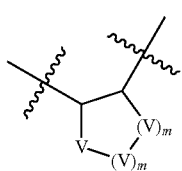

is selected from the groups below:

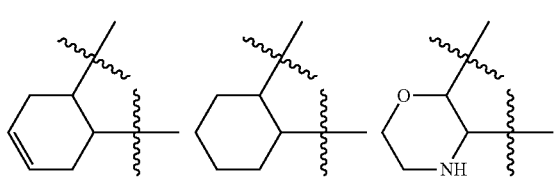

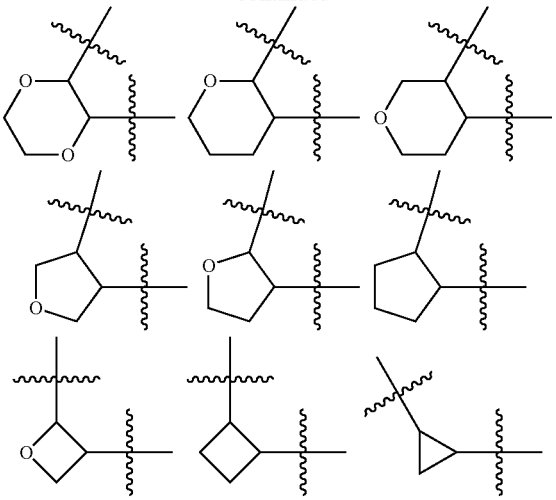

each of which is optionally substituted.

In certain embodiments, the present invention relates to compounds of Formulae (VI-5)~(VI-6), or Formulae (VII-5)~(VII-6), and pharmaceutically acceptable salts thereof, wherein

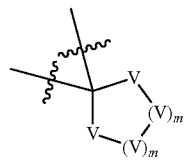

is selected from the groups below:

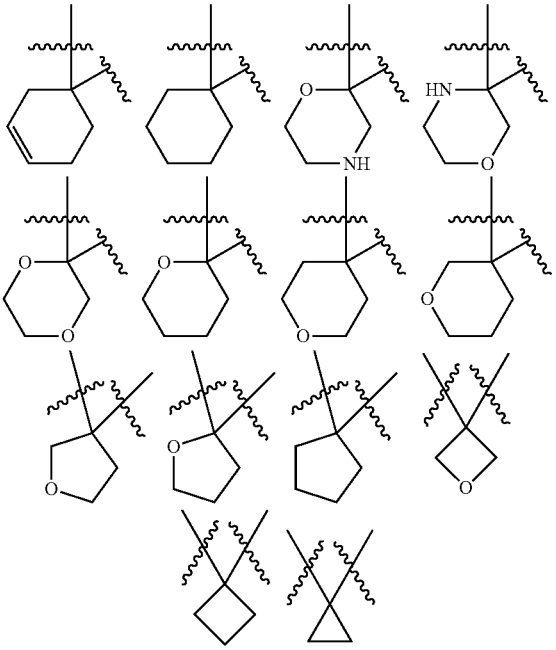

each of which is optionally substituted.

In certain embodiments, the present invention relates to compounds of Formulae (VI-1)~(VI-6), or Formulae (VII- 1)~(VII-6), and pharmaceutically acceptable salts thereof, wherein A is selected from the groups below:

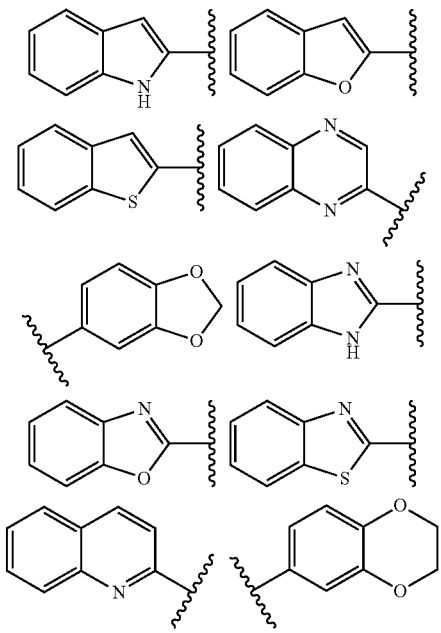

each of which is optionally substituted. Preferably, A has 0, 1 or 2 substituents. Preferably the substituents are independently selected from fluoro, chloro, hydroxy, methoxy, fluoromethoxy, difluoromethoxy, and trifluoromethoxy.

In certain embodiments, the present invention relates to a compound of one of Formulae (VI-1)~(VI-6), and Formulae (VII-1)~(VII-6), or a pharmaceutically acceptable salt thereof, wherein A is —$CH_2R_{23}$, and $R_{23}$ is previously defined.

In certain embodiments, the present invention relates to a compound of one of Formulae (VI-1)~(VI-6), and Formulae (VII-1)~(VII-6), or a pharmaceutically acceptable salt thereof, wherein X is —CN, —C(O)$CH_2$OC(O)$R_{21}$, —C(O)$CH_2$C(O)$R_{21}$, —C(O)$CH_2$O$R_{21}$, —C(O)$CH_2R_{22}$, —C(O)C(O)NH$R_{21}$, —C(O)$R_{21}$, —CH$R_{21}$OC(O)$R_{21}$, —CH$R_{21}$C(O)$_2R_{21}$, —CH$R_{21}$(O$R_{21}$), or —CH(O$R_{21}$)$_2$, and $R_{21}$ and $R_{22}$ are as previously defined.

In certain embodiments, the compound of Formula (I) is represented by one of Formulae (VIII-1)~(VIII-12), or a pharmaceutically acceptable salt thereof:

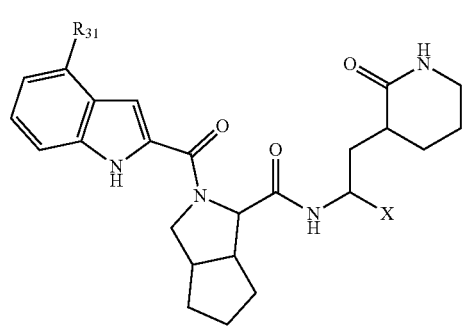

(VIII-1)

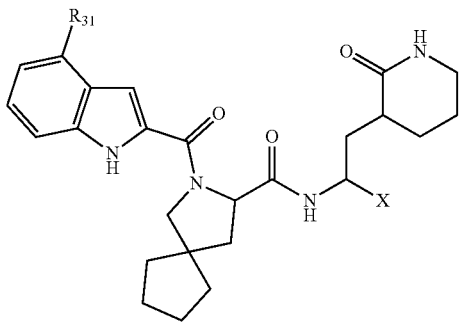

(VIII-2)

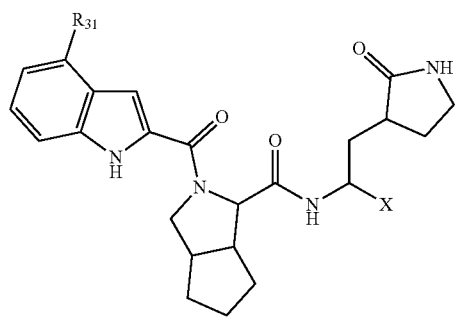

(VIII-3)

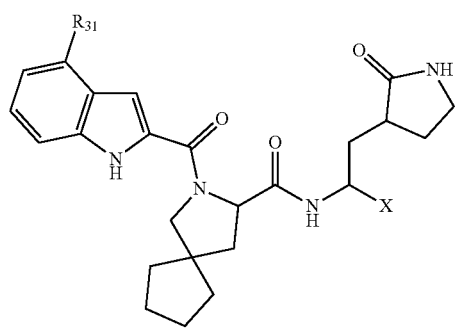

(VIII-4)

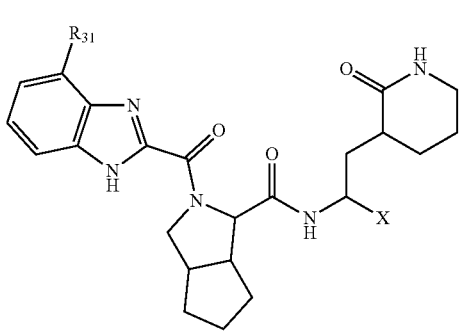

(VIII-5)

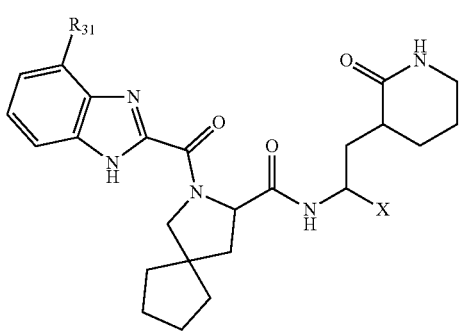

(VIII-6)

-continued

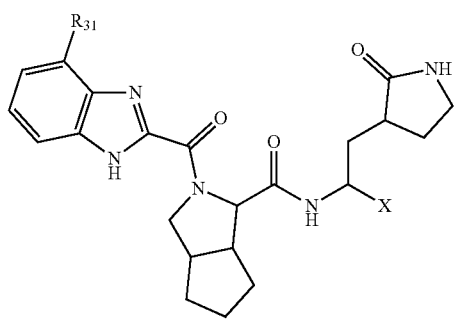
(VIII-7)

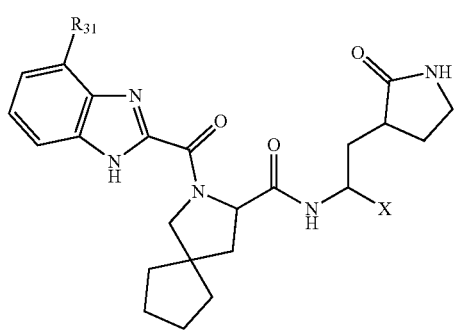
(VIII-8)

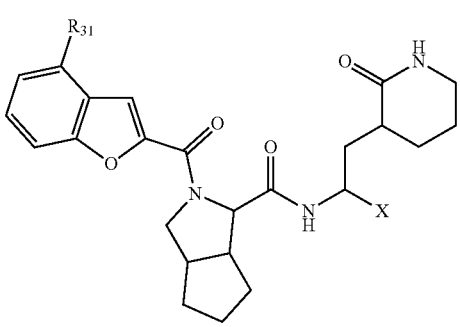
(VIII-9)

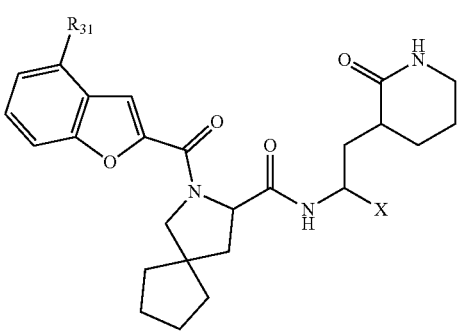
(VIII-10)

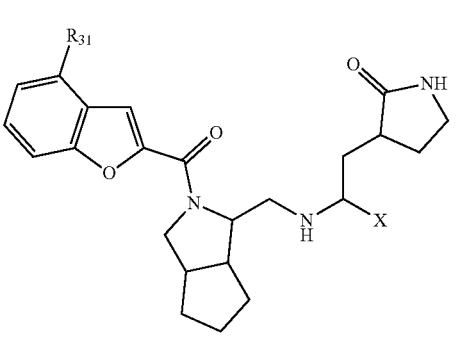
(VIII-11)

-continued

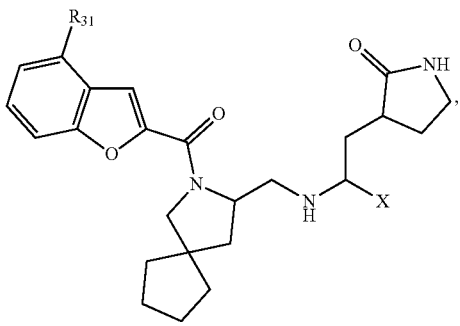
(VIII-12)

wherein $R_{31}$ is hydrogen, —F, —Cl, —OCH$_3$, or —OCHF$_2$; X is as previously defined. Preferably X is —CN, —C(O)CH$_2$OC(O)R$_{21}$, —C(O)CH$_2$C(O)$_2$R$_{21}$, —C(O)CH$_2$OR$_{21}$, —C(O)CH$_2$R$_{22}$, —C(O)C(O)NHR$_{21}$, —C(O)R$_{21}$, —CHR$_{21}$OC(O)R$_{21}$, —CHR$_{21}$C(O)$_2$R$_{21}$, —CHR$_{21}$(OR$_{21}$), or —CH(OR$_{21}$)$_2$, and R$_{21}$ and R$_{22}$ are as previously defined.

In certain embodiments, the compound of Formula (I) is represented by one of Formulae (IX-1)~(IX-8), or a pharmaceutically acceptable salt thereof:

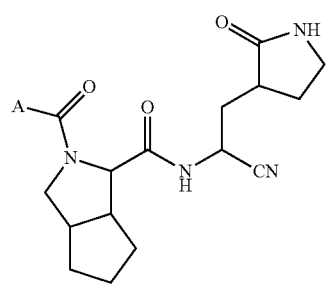
(IX-1)

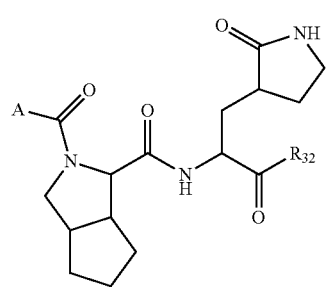
(IX-2)

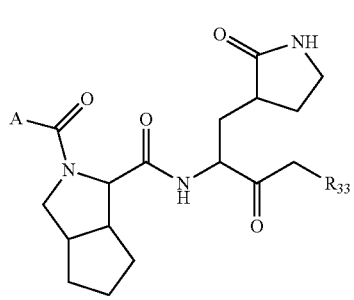
(IX-3)

-continued

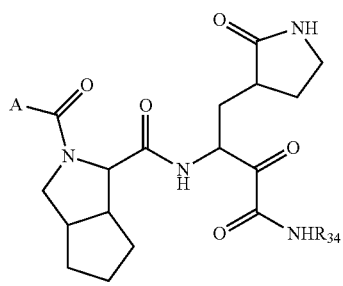
(IX-4)

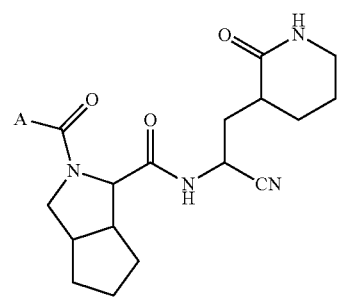
(IX-5)

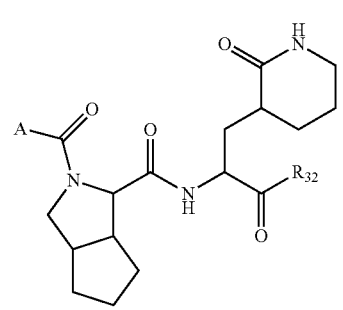
(IX-6)

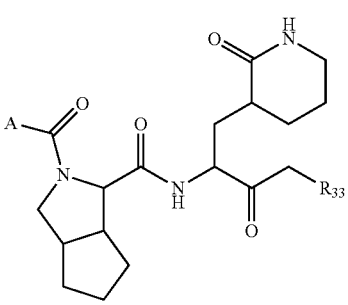
(IX-7)

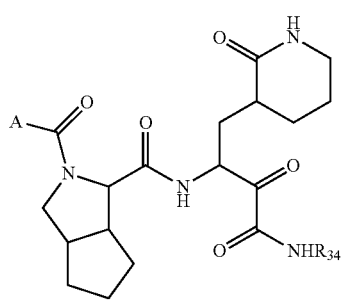
(IX-8)

wherein $R_{32}$ is hydrogen, —F, Cl, —CH$_3$, —CF$_3$ or —OR; $R_{33}$ is —Cl, —Br, —OR$_{21}$, —NHR$_{21}$, or —OC(O)R$_{21}$; $R_{34}$ is $R_{21}$, preferably, $R_{34}$ is optionally substituted —C$_1$-C$_6$ alkyl, optionally substituted —C$_3$-C$_8$ cycloalkyl, or optionally substituted 3- to 8-membered heterocycloalkyl, more preferably, $R_{34}$ is benzyl, cyclohexyl, isopropyl, t-butyl or optionally substituted methyl; and $R_{21}$ and A are as previously defined.

In certain embodiments, the compound of Formula (I) is represented by one of Formulae (IX-1)~(IX-8), or a pharmaceutically acceptable salt thereof, wherein $R_{32}$, $R_{33}$, and $R_{34}$ are as previously defined; A is selected from the groups below:

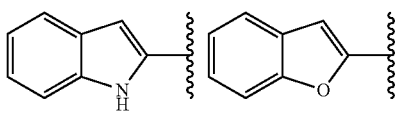

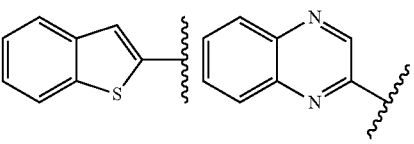

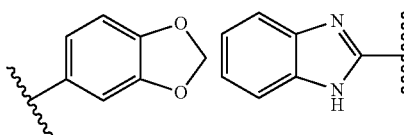

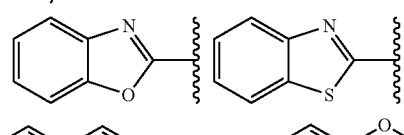

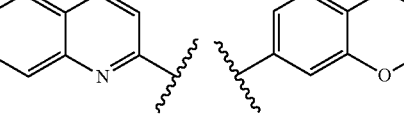

each of which is optionally substituted. Preferably, A has 0, 1 or 2 substituents. Preferably the substituents are independently selected from fluoro, chloro, hydroxy, methoxy, fluoromethoxy, difluoromethoxy, and trifluoromethoxy.

In certain embodiments, the compound of Formula (I) is represented by one of Formulae (IX-1)~(IX-8), wherein A is —CH$_2$R$_{23}$; $R_{23}$, $R_{32}$, $R_{33}$, and $R_{34}$ are as previously defined.

In certain embodiments, the compound of Formula (I) is represented by Formula (X-a) or a pharmaceutically acceptable salt thereof, wherein A and X are as previously defined,

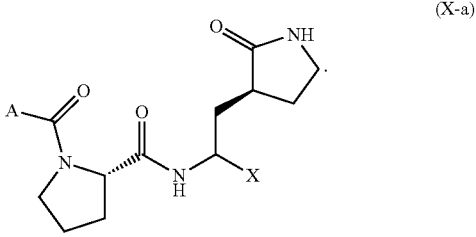
(X-a)

Representative compounds of the invention include, but are not limited to, compounds according to Formula (X-a), and pharmaceutically acceptable salts thereof, wherein A and X are delineated for each compound in Table 1.

TABLE 1
| Entry | A | X |
|---|---|---|
| A1 | 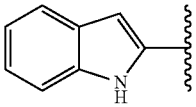 [SMILES: *c1cc2ccccc2[nH]1] | —CN |
| A2 | 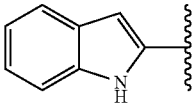 [SMILES: *c1cc2ccccc2[nH]1] | —C(O)H |
| A3 | 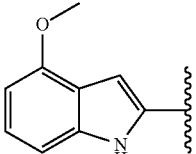 | —CN |
| A4 | 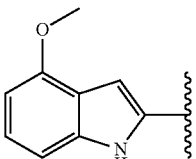 | —C(O)H |
| A5 | 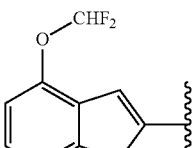 | —CN |
| A6 | 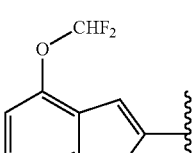 | —C(O)H |
| A7 | 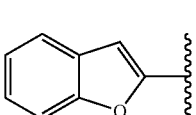 | —CN |
| A8 | 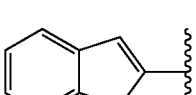 | —C(O)H |
| A9 | 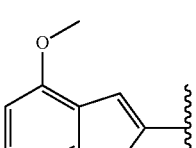 | —CN |
| A10 | 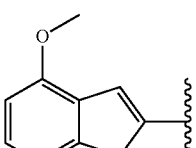 | —C(O)H |
| A11 | 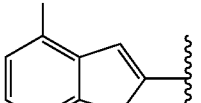 | —CN |
| A12 | 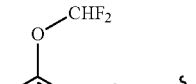 | —C(O)H |
| A13 | 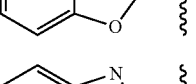 | —CN |
| A14 | 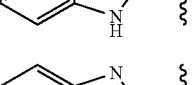 | —C(O)H |
| A15 | 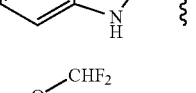 | —CN |
| A16 | 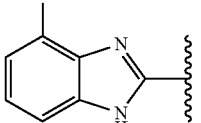 | —C(O)H |
| A17 | 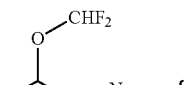 | —CN |
| A18 | 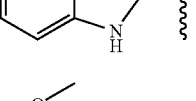 | —C(O)H |
| A19 | 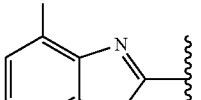 | 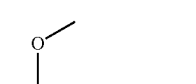 |
| A20 | 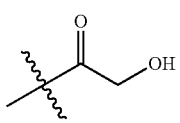 [SMILES: *C(=O)CO] | 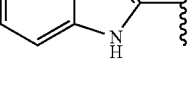 |

TABLE 1-continued
| Entry | A | X |
|---|---|---|
| A21 | 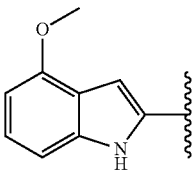 [SMILES: *c1cc2c(OC)cccc2[nH]1] | 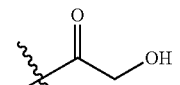 |
| A22 | 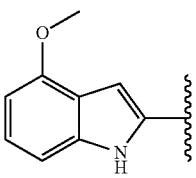 [SMILES: *c1cc2c(OC)cccc2[nH]1] | 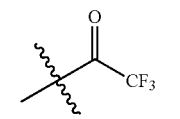 |
| A23 | 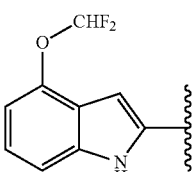 | 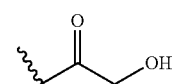 |
| A24 | 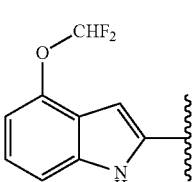 | 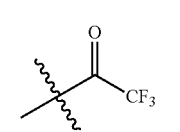 |
| A25 | 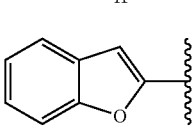 | 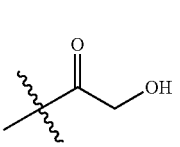 [SMILES: *C(=O)CO] |
| A26 | 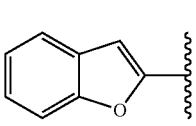 | 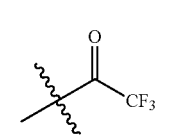 |
| A27 | 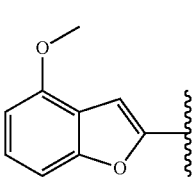 [SMILES: *c1cc2c(OC)cccc2o1] | 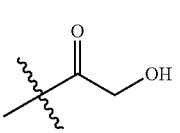 [SMILES: *C(=O)CO] |
| A28 | 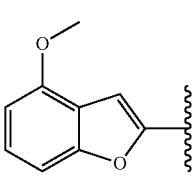 [SMILES: *c1cc2c(OC)cccc2o1] | 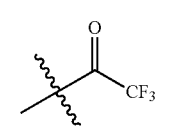 |
| A29 | 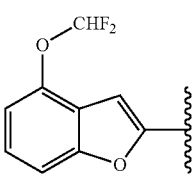 [SMILES: *c1cc2c(OC(F)F)cccc2o1] | 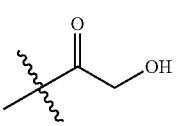 [SMILES: *C(=O)CO] |
TABLE 1-continued
| Entry | A | X |
|---|---|---|
| A30 | 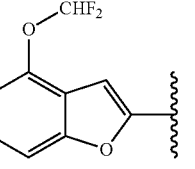 | 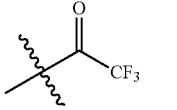 [SMILES: *C(=O)C(F)(F)F] |
| A31 | 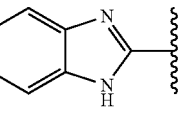 | 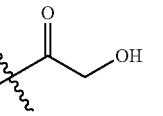 |
| A32 | 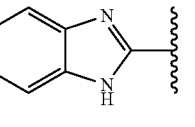 | 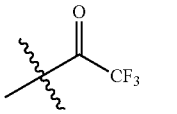 |
| A33 | 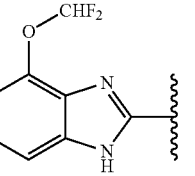 | 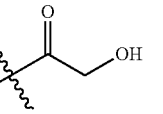 |
| A34 | 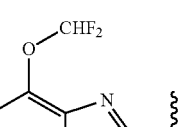 | 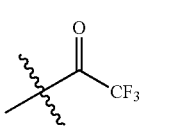 [SMILES: *C(=O)C(F)(F)F] |
| A35 | 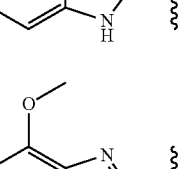 | 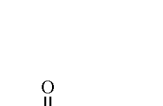 |
| A36 | 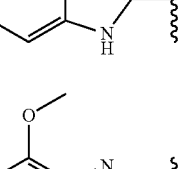 |  |
| A37 | 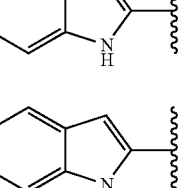 | 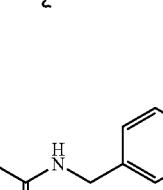 |
| A38 | 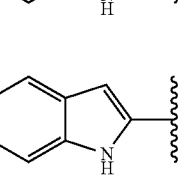 | 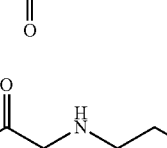 |

TABLE 1-continued

| Entry | A | X |
|---|---|---|
| A39 | 4-methoxy-1H-indol-2-yl | -C(O)C(CH3)-C(O)NH-benzyl |
| A40 | 4-methoxy-1H-indol-2-yl | -C(O)C(CH3)-C(O)NH-cyclohexyl |
| A41 | 4-(difluoromethoxy)-1H-indol-2-yl | -C(O)C(CH3)-C(O)NH-benzyl |
| A42 | 4-(difluoromethoxy)-1H-indol-2-yl | -C(O)C(CH3)-C(O)NH-cyclohexyl |
| A43 | benzofuran-2-yl | -C(O)C(CH3)-C(O)NH-benzyl |
| A44 | benzofuran-2-yl | -C(O)C(CH3)-C(O)NH-cyclohexyl |
| A45 | 4-methoxybenzofuran-2-yl | -C(O)C(CH3)-C(O)NH-benzyl |
| A46 | 4-methoxybenzofuran-2-yl | -C(O)C(CH3)-C(O)NH-cyclohexyl |
| A47 | 4-(difluoromethoxy)benzofuran-2-yl | -C(O)C(CH3)-C(O)NH-benzyl |
| A48 | 4-(difluoromethoxy)benzofuran-2-yl | -C(O)C(CH3)-C(O)NH-cyclohexyl |
| A49 | 1H-benzimidazol-2-yl | -C(O)C(CH3)-C(O)NH-benzyl |
| A50 | 1H-benzimidazol-2-yl | -C(O)C(CH3)-C(O)NH-cyclohexyl |
| A51 | 4-(difluoromethoxy)-1H-benzimidazol-2-yl | -C(O)C(CH3)-C(O)NH-benzyl |
| A52 | 4-(difluoromethoxy)-1H-benzimidazol-2-yl | -C(O)C(CH3)-C(O)NH-cyclohexyl |
| A53 | 4-methoxy-1H-benzimidazol-2-yl | -C(O)C(CH3)-C(O)NH-benzyl |
| A54 | 4-methoxy-1H-benzimidazol-2-yl | -C(O)C(CH3)-C(O)NH-cyclohexyl |

In certain embodiments, the compound of Formula (I) is represented by Formula (X-b) or a pharmaceutically acceptable salt thereof, wherein A and X are as previously defined,

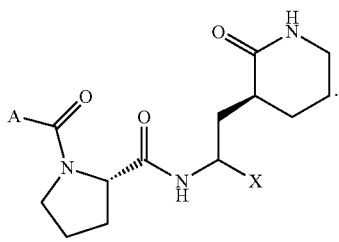

(X-b)

Representative compounds of the invention include, but are not limited to, compounds according to Formula (X-b), and pharmaceutically acceptable salts thereof, wherein A and X are delineated for each compound in Table 2.

TABLE 2

| Entry | A | X |
|---|---|---|
| B1 | 2-indolyl | —CN |
| B2 | 2-indolyl | —C(O)H |
| B3 | 4-methoxy-2-indolyl | —CN |
| B4 | 4-methoxy-2-indolyl | —C(O)H |
| B5 | 4-(OCHF$_2$)-2-indolyl | —CN |
| B6 | 4-(OCHF$_2$)-2-indolyl | —C(O)H |
| B7 | 2-benzofuranyl | —CN |

TABLE 2-continued

| Entry | A | X |
|---|---|---|
| B8 | 2-benzofuranyl | —C(O)H |
| B9 | 4-methoxy-2-benzofuranyl | —CN |
| B10 | 4-methoxy-2-benzofuranyl | —C(O)H |
| B11 | 4-(OCHF$_2$)-2-benzofuranyl | —CN |
| B12 | 4-(OCHF$_2$)-2-benzofuranyl | —C(O)H |
| B13 | 2-benzimidazolyl | —CN |
| B14 | 2-benzimidazolyl | —C(O)H |
| B15 | 4-(OCHF$_2$)-2-benzimidazolyl | —CN |
| B16 | 4-(OCHF$_2$)-2-benzimidazolyl | —C(O)H |
| B17 | 4-methoxy-2-benzimidazolyl | —CN |

TABLE 2-continued

| Entry | A | X |
|---|---|---|
| B18 | 4-methoxy-1H-benzimidazol-2-yl | —C(O)H |
| B19 | 1H-indol-2-yl | —C(O)CH₂OH (α,α-dimethyl) |
| B20 | 1H-indol-2-yl | —C(O)CF₃ (α,α-dimethyl) |
| B21 | 4-methoxy-1H-indol-2-yl | —C(O)CH₂OH (α,α-dimethyl) |
| B22 | 4-methoxy-1H-indol-2-yl | —C(O)CF₃ (α,α-dimethyl) |
| B23 | 4-(difluoromethoxy)-1H-indol-2-yl | —C(O)CH₂OH (α,α-dimethyl) |
| B24 | 4-(difluoromethoxy)-1H-indol-2-yl | —C(O)CF₃ (α,α-dimethyl) |
| B25 | benzofuran-2-yl | —C(O)CH₂OH (α,α-dimethyl) |
| B26 | benzofuran-2-yl | —C(O)CF₃ (α,α-dimethyl) |
| B27 | 4-methoxybenzofuran-2-yl | —C(O)CH₂OH (α,α-dimethyl) |
| B28 | 4-methoxybenzofuran-2-yl | —C(O)CF₃ (α,α-dimethyl) |
| B29 | 4-(difluoromethoxy)benzofuran-2-yl | —C(O)CH₂OH (α,α-dimethyl) |
| B30 | 4-(difluoromethoxy)benzofuran-2-yl | —C(O)CF₃ (α,α-dimethyl) |
| B31 | 1H-benzimidazol-2-yl | —C(O)CH₂OH (α,α-dimethyl) |
| B32 | 1H-benzimidazol-2-yl | —C(O)CF₃ (α,α-dimethyl) |
| B33 | 4-(difluoromethoxy)-1H-benzimidazol-2-yl | —C(O)CH₂OH (α,α-dimethyl) |
| B34 | 4-(difluoromethoxy)-1H-benzimidazol-2-yl | —C(O)CF₃ (α,α-dimethyl) |
| B35 | 4-methoxy-1H-benzimidazol-2-yl | —C(O)CH₂OH (α,α-dimethyl) |

TABLE 2-continued

| Entry | A | X |
|---|---|---|
| B36 | 4-methoxy-1H-benzimidazol-2-yl | -C(O)C(CH3)2-CF3 (α,α-dimethyl trifluoromethyl ketone) |
| B37 | 1H-indol-2-yl | -C(O)C(CH3)2-C(O)NH-CH2Ph |
| B38 | 1H-indol-2-yl | -C(O)C(CH3)2-C(O)NH-cyclohexyl |
| B39 | 4-methoxy-1H-indol-2-yl | -C(O)C(CH3)2-C(O)NH-CH2Ph |
| B40 | 4-methoxy-1H-indol-2-yl | -C(O)C(CH3)2-C(O)NH-cyclohexyl |
| B41 | 4-(OCHF2)-1H-indol-2-yl | -C(O)C(CH3)2-C(O)NH-CH2Ph |
| B42 | 4-(OCHF2)-1H-indol-2-yl | -C(O)C(CH3)2-C(O)NH-cyclohexyl |
| B43 | benzofuran-2-yl | -C(O)C(CH3)2-C(O)NH-CH2Ph |
| B44 | benzofuran-2-yl | -C(O)C(CH3)2-C(O)NH-cyclohexyl |
| B45 | 4-methoxy-benzofuran-2-yl | -C(O)C(CH3)2-C(O)NH-CH2Ph |
| B46 | 4-methoxy-benzofuran-2-yl | -C(O)C(CH3)2-C(O)NH-cyclohexyl |
| B47 | 4-(OCHF2)-benzofuran-2-yl | -C(O)C(CH3)2-C(O)NH-CH2Ph |
| B48 | 4-(OCHF2)-benzofuran-2-yl | -C(O)C(CH3)2-C(O)NH-cyclohexyl |
| B49 | 1H-benzimidazol-2-yl | -C(O)C(CH3)2-C(O)NH-CH2Ph |
| B50 | 1H-benzimidazol-2-yl | -C(O)C(CH3)2-C(O)NH-cyclohexyl |
| B51 | 4-(OCHF2)-1H-benzimidazol-2-yl | -C(O)C(CH3)2-C(O)NH-CH2Ph |
| B52 | 4-(OCHF2)-1H-benzimidazol-2-yl | -C(O)C(CH3)2-C(O)NH-cyclohexyl |
| B53 | 4-methoxy-1H-benzimidazol-2-yl | -C(O)C(CH3)2-C(O)NH-CH2Ph |

TABLE 2-continued

| Entry | A | X |
|---|---|---|
| B54 | 4-methoxybenzimidazol-2-yl | 2-oxo-N-cyclohexyl-acetamide with gem-dimethyl |

In certain embodiments, the compound of Formula (I) is represented by Formula (X-c) or a pharmaceutically acceptable salt thereof, wherein A and X are previously defined,

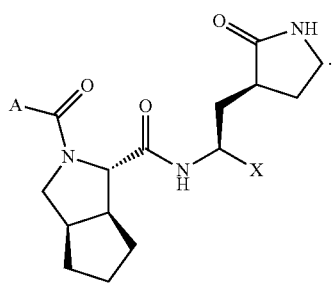

(X-c)

Representative compounds of the invention include, but are not limited to, compounds according to Formula (X-c), and pharmaceutically acceptable salts thereof, wherein A and X are delineated for each compound in Table 3.

TABLE 3

| Entry | A | X |
|---|---|---|
| C1 | indol-2-yl | —CN |
| C2 | indol-2-yl | —C(O)H |
| C3 | 4-methoxyindol-2-yl | —CN |
| C4 | 4-methoxyindol-2-yl | —C(O)H |
| C5 | 4-(OCHF$_2$)indol-2-yl | —CN |
| C6 | 4-(OCHF$_2$)indol-2-yl | —C(O)H |
| C7 | benzofuran-2-yl | —CN |
| C8 | benzofuran-2-yl | —C(O)H |
| C9 | 4-methoxybenzofuran-2-yl | —CN |
| C10 | 4-methoxybenzofuran-2-yl | —C(O)H |
| C11 | 4-(OCHF$_2$)benzofuran-2-yl | —CN |
| C12 | 4-(OCHF$_2$)benzofuran-2-yl | —C(O)H |
| C13 | benzimidazol-2-yl | —CN |
| C14 | benzimidazol-2-yl | —C(O)H |

TABLE 3-continued
| Entry | A | X |
|---|---|---|
| C15 | 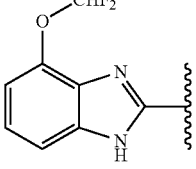 [SMILES: *c1nc2c(OC)cccc2[nH]1] | —CN |
| C16 | 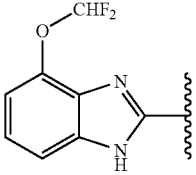 | —C(O)H |
| C17 | 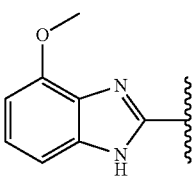 | —CN |
| C18 | 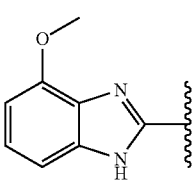 [SMILES: *c1nc2c(OC)cccc2[nH]1] | —C(O)H |
| C19 | 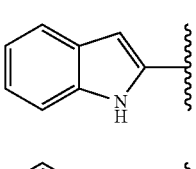 | 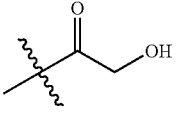 [SMILES: *C(=O)CO] |
| C20 | 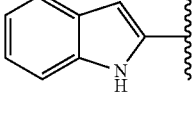 | 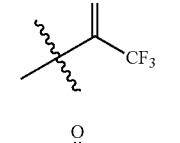 |
| C21 | 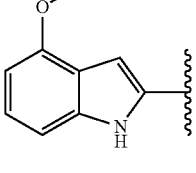 | 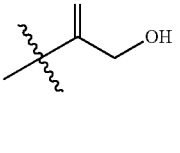 |
| C22 | 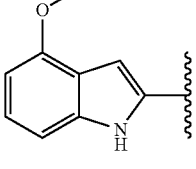 | 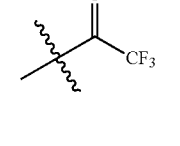 |
| C23 | 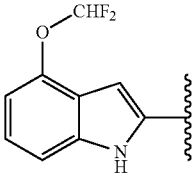 [SMILES: *c1cc2c(OC(F)F)cccc2[nH]1] | 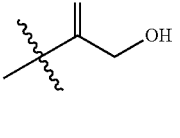 |
| C24 | 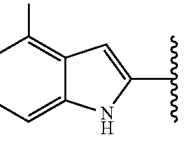 | 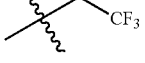 |
| C25 | 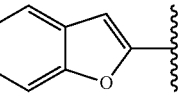 | 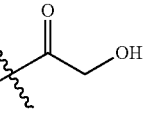 |
| C26 | 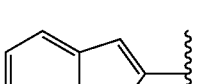 | 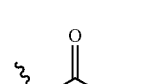 |
| C27 | 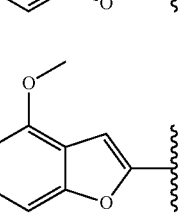 | 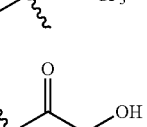 |
| C28 | 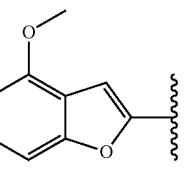 | 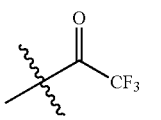 [SMILES: *C(=O)C(F)(F)F] |
| C29 | 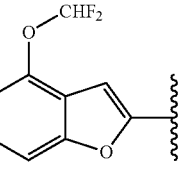 | 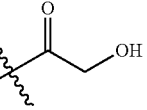 |
| C30 | 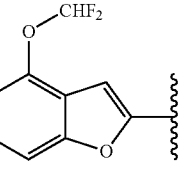 | 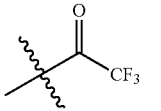 [SMILES: *C(=O)C(F)(F)F] |
| C31 | 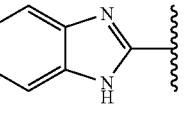 | 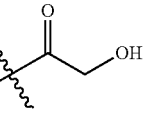 |
| C32 | 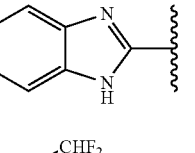 | 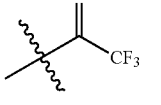 |
| C33 | 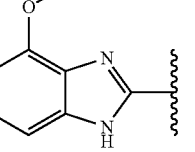 | 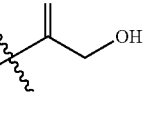 |

TABLE 3-continued

| Entry | A | X |
|---|---|---|
| C34 | 4-(OCHF$_2$)-benzimidazol-2-yl | -C(CH$_3$)(-)C(O)CF$_3$ |
| C35 | 4-methoxy-benzimidazol-2-yl | -C(CH$_3$)(-)C(O)CH$_2$OH |
| C36 | 4-methoxy-benzimidazol-2-yl | -C(CH$_3$)(-)C(O)CF$_3$ |
| C37 | 1H-indol-2-yl | -C(CH$_3$)(-)C(O)C(O)NHCH$_2$Ph |
| C38 | 1H-indol-2-yl | -C(CH$_3$)(-)C(O)C(O)NHCy |
| C39 | 4-methoxy-1H-indol-2-yl | -C(CH$_3$)(-)C(O)C(O)NHCH$_2$Ph |
| C40 | 4-methoxy-1H-indol-2-yl | -C(CH$_3$)(-)C(O)C(O)NHCy |
| C41 | 4-(OCHF$_2$)-1H-indol-2-yl | -C(CH$_3$)(-)C(O)C(O)NHCH$_2$Ph |
| C42 | 4-(OCHF$_2$)-1H-indol-2-yl | -C(CH$_3$)(-)C(O)C(O)NHCy |
| C43 | benzofuran-2-yl | -C(CH$_3$)(-)C(O)C(O)NHCH$_2$Ph |
| C44 | benzofuran-2-yl | -C(CH$_3$)(-)C(O)C(O)NHCy |
| C45 | 4-methoxy-benzofuran-2-yl | -C(CH$_3$)(-)C(O)C(O)NHCH$_2$Ph |
| C46 | 4-methoxy-benzofuran-2-yl | -C(CH$_3$)(-)C(O)C(O)NHCy |
| C47 | 4-(OCHF$_2$)-benzofuran-2-yl | -C(CH$_3$)(-)C(O)C(O)NHCH$_2$Ph |
| C48 | 4-(OCHF$_2$)-benzofuran-2-yl | -C(CH$_3$)(-)C(O)C(O)NHCy |
| C49 | benzimidazol-2-yl | -C(CH$_3$)(-)C(O)C(O)NHCH$_2$Ph |
| C50 | benzimidazol-2-yl | -C(CH$_3$)(-)C(O)C(O)NHCy |

TABLE 3-continued

| Entry | A | X |
|---|---|---|
| C51 | 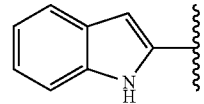 [SMILES: *c1cc2ccccc2[nH]1] | 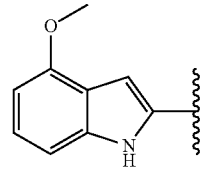 [SMILES: *c1cc2c(OC)cccc2[nH]1] |
| C52 | 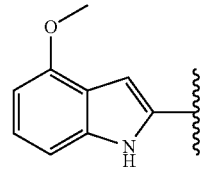 [SMILES: *c1cc2c(OC)cccc2[nH]1] | 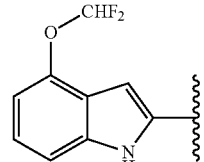 |
| C53 | 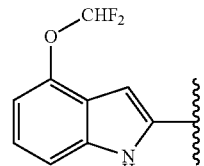 [SMILES: *c1cc2c(OC(F)F)cccc2o1] | 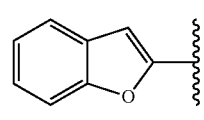 [SMILES: *c1cc2ccccc2o1] |
| C54 | 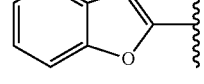 | 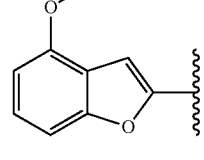 |

In certain embodiments, the compound of Formula (I) is represented by Formula (X-d) or a pharmaceutically acceptable salt thereof, wherein A and X are previously defined,

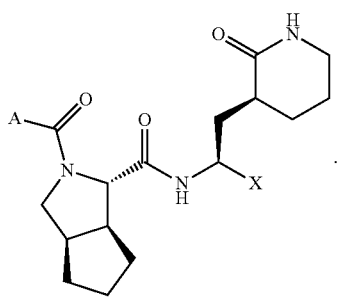

(X-d)

Representative compounds of the invention include, but are not limited to, compounds according to Formula (X-d), and pharmaceutically acceptable salts thereof, wherein A and X are delineated for each compound in Table 4.

TABLE 4

| Entry | A | X |
|---|---|---|
| D1 |  | —CN |

TABLE 4-continued

| Entry | A | X |
|---|---|---|
| D2 | indole | —C(O)H |
| D3 | 4-methoxyindole | —CN |
| D4 | 4-methoxyindole | —C(O)H |
| D5 | 4-OCHF₂-indole | —CN |
| D6 | 4-OCHF₂-indole | —C(O)H |
| D7 | benzofuran | —CN |
| D8 | benzofuran | —C(O)H |
| D9 | 4-methoxybenzofuran | —CN |
| D10 | 4-methoxybenzofuran | —C(O)H |

TABLE 4-continued

| Entry | A | X |
|---|---|---|
| D11 | 4-(OCHF2)-benzofuran-2-yl | —CN |
| D12 | 4-(OCHF2)-benzofuran-2-yl | —C(O)H |
| D13 | 1H-benzimidazol-2-yl | —CN |
| D14 | 1H-benzimidazol-2-yl | —C(O)H |
| D15 | 4-(OCHF2)-1H-benzimidazol-2-yl | —CN |
| D16 | 4-(OCHF2)-1H-benzimidazol-2-yl | —C(O)H |
| D17 | 4-(OMe)-1H-benzimidazol-2-yl | —CN |
| D18 | 4-(OMe)-1H-benzimidazol-2-yl | —C(O)H |
| D19 | 1H-indol-2-yl | —C(CH3)(C(O)CH2OH) |
| D20 | 1H-indol-2-yl | —C(CH3)(C(O)CF3) |
| D21 | 4-(OMe)-1H-indol-2-yl | —C(CH3)(C(O)CH2OH) |
| D22 | 4-(OMe)-1H-indol-2-yl | —C(CH3)(C(O)CF3) |
| D23 | 4-(OCHF2)-1H-indol-2-yl | —C(CH3)(C(O)CH2OH) |
| D24 | 4-(OCHF2)-1H-indol-2-yl | —C(CH3)(C(O)CF3) |
| D25 | benzofuran-2-yl | —C(CH3)(C(O)CH2OH) |
| D26 | benzofuran-2-yl | —C(CH3)(C(O)CF3) |
| D27 | 4-(OMe)-benzofuran-2-yl | —C(CH3)(C(O)CH2OH) |
| D28 | 4-(OMe)-benzofuran-2-yl | —C(CH3)(C(O)CF3) |
| D29 | 4-(OCHF2)-benzofuran-2-yl | —C(CH3)(C(O)CH2OH) |

TABLE 4-continued

| Entry | A | X |
|---|---|---|
| D30 | 4-(OCHF₂)-benzofuran-2-yl | -C(CH₃)(C(O)CF₃)- |
| D31 | 1H-benzimidazol-2-yl | -C(CH₃)(C(O)CH₂OH)- |
| D32 | 1H-benzimidazol-2-yl | -C(CH₃)(C(O)CF₃)- |
| D33 | 4-(OCHF₂)-1H-benzimidazol-2-yl | -C(CH₃)(C(O)CH₂OH)- |
| D34 | 4-(OCHF₂)-1H-benzimidazol-2-yl | -C(CH₃)(C(O)CF₃)- |
| D35 | 4-methoxy-1H-benzimidazol-2-yl | -C(CH₃)(C(O)CH₂OH)- |
| D36 | 4-methoxy-1H-benzimidazol-2-yl | -C(CH₃)(C(O)CF₃)- |
| D37 | 1H-indol-2-yl | -C(CH₃)(C(O)C(O)NHCH₂Ph)- |
| D38 | 1H-indol-2-yl | -C(CH₃)(C(O)C(O)NHCy)- |
| D39 | 4-methoxy-1H-indol-2-yl | -C(CH₃)(C(O)C(O)NHCH₂Ph)- |
| D40 | 4-methoxy-1H-indol-2-yl | -C(CH₃)(C(O)C(O)NHCy)- |
| D41 | 4-(OCHF₂)-1H-indol-2-yl | -C(CH₃)(C(O)C(O)NHCH₂Ph)- |
| D42 | 4-(OCHF₂)-1H-indol-2-yl | -C(CH₃)(C(O)C(O)NHCy)- |
| D43 | benzofuran-2-yl | -C(CH₃)(C(O)C(O)NHCH₂Ph)- |
| D44 | benzofuran-2-yl | -C(CH₃)(C(O)C(O)NHCy)- |
| D45 | 4-methoxy-benzofuran-2-yl | -C(CH₃)(C(O)C(O)NHCH₂Ph)- |
| D46 | 4-methoxy-benzofuran-2-yl | -C(CH₃)(C(O)C(O)NHCy)- |
| D47 | 4-(OCHF₂)-benzofuran-2-yl | -C(CH₃)(C(O)C(O)NHCH₂Ph)- |

TABLE 4-continued

| Entry | A | X |
|---|---|---|
| D48 | 4-(OCHF2)-benzofuran-2-yl | -C(O)C(CH3)2C(O)NH-cyclohexyl |
| D49 | 1H-benzimidazol-2-yl | -C(O)C(CH3)2C(O)NH-benzyl |
| D50 | 1H-benzimidazol-2-yl | -C(O)C(CH3)2C(O)NH-cyclohexyl |
| D51 | 4-(OCHF2)-1H-benzimidazol-2-yl | -C(O)C(CH3)2C(O)NH-benzyl |
| D52 | 4-(OCHF2)-1H-benzimidazol-2-yl | -C(O)C(CH3)2C(O)NH-cyclohexyl |
| D53 | 4-methoxy-1H-benzimidazol-2-yl | -C(O)C(CH3)2C(O)NH-benzyl |
| D54 | 4-methoxy-1H-benzimidazol-2-yl | -C(O)C(CH3)2C(O)NH-cyclohexyl |

In certain embodiments, the compound of Formula (I) is represented by Formula (X-e) or a pharmaceutically acceptable salt thereof, wherein A and X are previously defined,

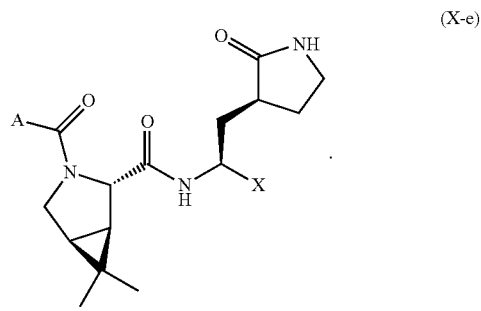

(X-e)

Representative compounds of the invention include, but are not limited to, compounds according to Formula (X-e), and pharmaceutically acceptable salts thereof, wherein A and X are delineated for each compound in Table 5.

TABLE 5

| Entry | A | X | Entry | A | X |
|---|---|---|---|---|---|
| E1 | 1H-indol-2-yl | —CN | E2 | 1H-indol-2-yl | —C(O)H |
| E3 | 4-methoxy-1H-indol-2-yl | —CN | E4 | 4-methoxy-1H-indol-2-yl | —C(O)H |
| E5 | 4-(OCHF2)-1H-indol-2-yl | —CN | E6 | 4-(OCHF2)-1H-indol-2-yl | —C(O)H |

TABLE 5-continued
| Entry | A | X | Entry | A | X |
|---|---|---|---|---|---|
| E7 | 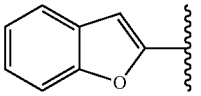 [SMILES: *c1cc2ccccc2o1] | —CN | E8 | 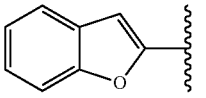 [SMILES: *c1cc2ccccc2o1] | —C(O)H |
| E9 | 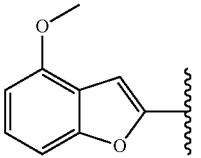 [SMILES: *c1cc2c(OC)cccc2o1] | —CN | E10 | 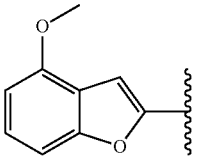 [SMILES: *c1cc2c(OC)cccc2o1] | —C(O)H |
| E11 | 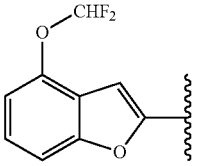 [SMILES: *c1cc2c(OC(F)F)cccc2o1] | —CN | E12 | 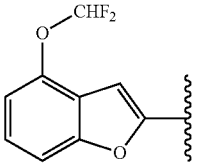 [SMILES: *c1cc2c(OC(F)F)cccc2o1] | —C(O)H |
| E13 | 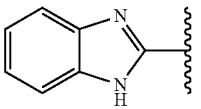 | —CN | E14 | 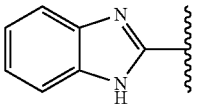 | —C(O)H |
| E15 | 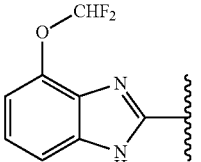 | —CN | E16 | 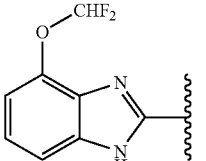 | —C(O)H |
| E17 | 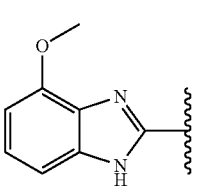 | —CN | E18 | 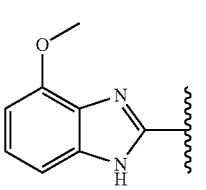 | —C(O)H |
| E19 | 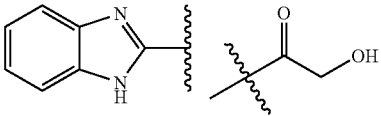 | 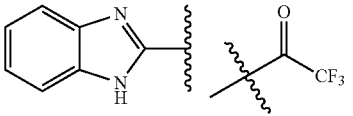 | E20 | 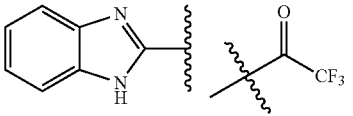 | 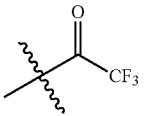 [SMILES: *C(=O)C(F)(F)F] |
| E21 | 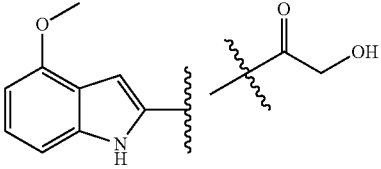 | 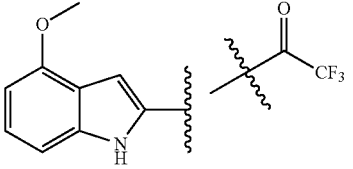 | E22 | 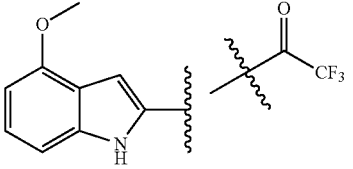 | 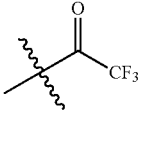 |
| E23 | 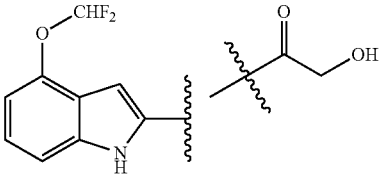 | 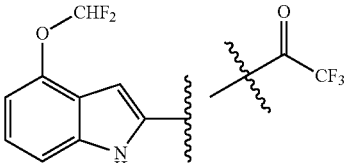 | E24 | 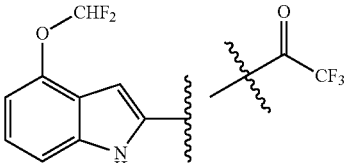 | 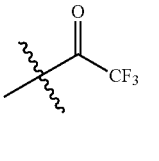 [SMILES: *C(=O)C(F)(F)F] |
| E25 | 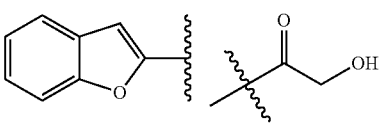 | 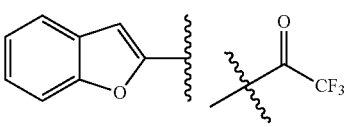 | E26 | 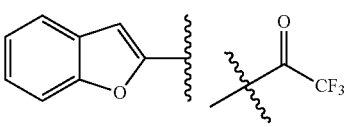 | 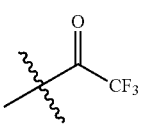 [SMILES: *C(=O)C(F)(F)F] |

TABLE 5-continued

| Entry | A | X | Entry | A | X |
|---|---|---|---|---|---|
| E27 | 4-methoxybenzofuran-2-yl | -C(O)CH₂OH | E28 | 4-methoxybenzofuran-2-yl | -C(O)CF₃ |
| E29 | 4-(OCHF₂)benzofuran-2-yl | -C(O)CH₂OH | E30 | 4-(OCHF₂)benzofuran-2-yl | -C(O)CF₃ |
| E31 | 1H-benzimidazol-2-yl | -C(O)CH₂OH | E32 | 1H-benzimidazol-2-yl | -C(O)CF₃ |
| E33 | 4-(OCHF₂)-1H-benzimidazol-2-yl | -C(O)CH₂OH | E34 | 4-(OCHF₂)-1H-benzimidazol-2-yl | -C(O)CF₃ |
| E35 | 4-methoxy-1H-benzimidazol-2-yl | -C(O)CH₂OH | E36 | 4-methoxy-1H-benzimidazol-2-yl | -C(O)CF₃ |
| E37 | 1H-indol-2-yl | -C(O)C(O)NHCH₂Ph | E38 | 1H-indol-2-yl | -C(O)C(O)NHCy |
| E39 | 4-methoxy-1H-indol-2-yl | -C(O)C(O)NHCH₂Ph | E40 | 4-methoxy-1H-indol-2-yl | -C(O)C(O)NHCy |
| E41 | 4-(OCHF₂)-1H-indol-2-yl | -C(O)C(O)NHCH₂Ph | E42 | 4-(OCHF₂)-1H-indol-2-yl | -C(O)C(O)NHCy |
| E43 | benzofuran-2-yl | -C(O)C(O)NHCH₂Ph | E44 | benzofuran-2-yl | -C(O)C(O)NHCy |

TABLE 5-continued

| Entry | A | X | Entry | A | X |
|---|---|---|---|---|---|
| E45 | 4-methoxybenzofuran-2-yl | -C(O)C(CH3)(-)C(O)NHCH2Ph | E46 | 4-methoxybenzofuran-2-yl | -C(O)C(CH3)(-)C(O)NH-cyclohexyl |
| E47 | 4-(OCHF2)benzofuran-2-yl | -C(O)C(CH3)(-)C(O)NHCH2Ph | E48 | 4-(OCHF2)benzofuran-2-yl | -C(O)C(CH3)(-)C(O)NH-cyclohexyl |
| E49 | 1H-benzimidazol-2-yl | -C(O)C(CH3)(-)C(O)NHCH2Ph | E50 | 1H-benzimidazol-2-yl | -C(O)C(CH3)(-)C(O)NH-cyclohexyl |
| E51 | 4-(OCHF2)-1H-benzimidazol-2-yl | -C(O)C(CH3)(-)C(O)NHCH2Ph | E52 | 4-(OCHF2)-1H-benzimidazol-2-yl | -C(O)C(CH3)(-)C(O)NH-cyclohexyl |
| E53 | 4-methoxy-1H-benzimidazol-2-yl | -C(O)C(CH3)(-)C(O)NHCH2Ph | E54 | 4-methoxy-1H-benzimidazol-2-yl | -C(O)C(CH3)(-)C(O)NH-cyclohexyl |

In certain embodiments, the compound of Formula (I) is represented by Formula (X-f) or a pharmaceutically acceptable salt thereof, wherein A and X are previously defined,

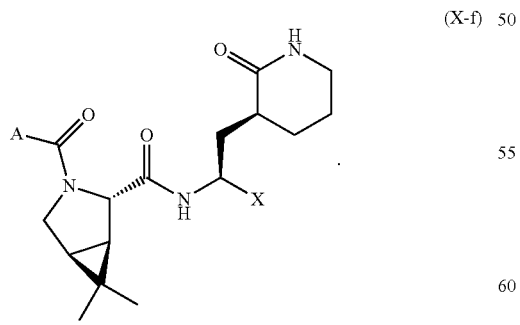

(X-f)

Representative compounds of the invention include, but are not limited to, compounds according to Formula (X-f), and pharmaceutically acceptable salts thereof, wherein A and X are delineated for each compound in Table 6.

TABLE 6

| Entry | A | X | Entry | A | X |
|---|---|---|---|---|---|
| F1 | indole-2-yl | —CN | F2 | indole-2-yl | —C(O)H |
| F3 | 4-methoxyindole-2-yl | —CN | F4 | 4-methoxyindole-2-yl | —C(O)H |
| F5 | 4-(difluoromethoxy)indole-2-yl | —CN | F6 | 4-(difluoromethoxy)indole-2-yl | —C(O)H |
| F7 | benzofuran-2-yl | —CN | F8 | benzofuran-2-yl | —C(O)H |
| F9 | 4-methoxybenzofuran-2-yl | —CN | F10 | 4-methoxybenzofuran-2-yl | —C(O)H |
| F11 | 4-(difluoromethoxy)benzofuran-2-yl | —CN | F12 | 4-(difluoromethoxy)benzofuran-2-yl | —C(O)H |
| F13 | benzimidazol-2-yl | —CN | F14 | benzimidazol-2-yl | —C(O)H |
| F15 | 4-(difluoromethoxy)benzimidazol-2-yl | —CN | F16 | 4-(difluoromethoxy)benzimidazol-2-yl | —C(O)H |
| F17 | 4-methoxybenzimidazol-2-yl | —CN | F18 | 4-methoxybenzimidazol-2-yl | —C(O)H |
| F19 | indole-2-yl | —C(CH₃)(C(O)CH₂OH) | F20 | indole-2-yl | —C(CH₃)(C(O)CF₃) |

TABLE 6-continued

| Entry | A | X | Entry | A | X |
|---|---|---|---|---|---|
| F21 | 4-methoxy-1H-indol-2-yl | -C(O)CH(CH3)CH2OH | F22 | 4-methoxy-1H-indol-2-yl | -C(O)C(CH3)(CF3)- |
| F23 | 4-(difluoromethoxy)-1H-indol-2-yl | -C(O)CH(CH3)CH2OH | F24 | 4-(difluoromethoxy)-1H-indol-2-yl | -C(O)C(CH3)(CF3)- |
| F25 | benzofuran-2-yl | -C(O)CH(CH3)CH2OH | F26 | benzofuran-2-yl | -C(O)C(CH3)(CF3)- |
| F27 | 4-methoxybenzofuran-2-yl | -C(O)CH(CH3)CH2OH | F28 | 4-methoxybenzofuran-2-yl | -C(O)C(CH3)(CF3)- |
| F29 | 4-(difluoromethoxy)benzofuran-2-yl | -C(O)CH(CH3)CH2OH | F30 | 4-(difluoromethoxy)benzofuran-2-yl | -C(O)C(CH3)(CF3)- |
| F31 | 1H-benzimidazol-2-yl | -C(O)CH(CH3)CH2OH | F32 | 1H-benzimidazol-2-yl | -C(O)C(CH3)(CF3)- |
| F33 | 4-(difluoromethoxy)-1H-benzimidazol-2-yl | -C(O)CH(CH3)CH2OH | F34 | 4-(difluoromethoxy)-1H-benzimidazol-2-yl | -C(O)C(CH3)(CF3)- |
| F35 | 4-methoxy-1H-benzimidazol-2-yl | -C(O)CH(CH3)CH2OH | F36 | 4-methoxy-1H-benzimidazol-2-yl | -C(O)C(CH3)(CF3)- |
| F37 | 1H-indol-2-yl | -C(O)C(CH3)(C(O)NHCH2Ph)- | F38 | 1H-indol-2-yl | -C(O)C(CH3)(C(O)NHCy)- |

TABLE 6-continued

| Entry | A | X | Entry | A | X |
|---|---|---|---|---|---|
| F39 | 4-methoxyindole | α-ketoamide-N-benzyl | F40 | 4-methoxyindole | α-ketoamide-N-cyclohexyl |
| F41 | 4-(OCHF₂)indole | α-ketoamide-N-benzyl | F42 | 4-(OCHF₂)indole | α-ketoamide-N-cyclohexyl |
| F43 | benzofuran | α-ketoamide-N-benzyl | F44 | benzofuran | α-ketoamide-N-cyclohexyl |
| F45 | 4-methoxybenzofuran | α-ketoamide-N-benzyl | F46 | 4-methoxybenzofuran | α-ketoamide-N-cyclohexyl |
| F47 | 4-(OCHF₂)benzofuran | α-ketoamide-N-benzyl | F48 | 4-(OCHF₂)benzofuran | α-ketoamide-N-cyclohexyl |
| F49 | benzimidazole | α-ketoamide-N-benzyl | F50 | benzimidazole | α-ketoamide-N-cyclohexyl |
| F51 | 4-(OCHF₂)benzimidazole | α-ketoamide-N-benzyl | F52 | 4-(OCHF₂)benzimidazole | α-ketoamide-N-cyclohexyl |
| F53 | 4-methoxybenzimidazole | α-ketoamide-N-benzyl | F54 | 4-methoxybenzimidazole | α-ketoamide-N-cyclohexyl |

In certain embodiments, the compound of Formula (I) is represented by one of Formulae (XI-1)~(XI-8), or a pharmaceutically acceptable salt thereof, (XI-1)
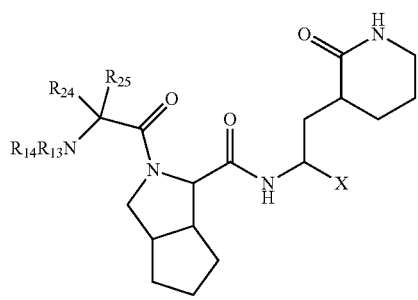
(XI-2)
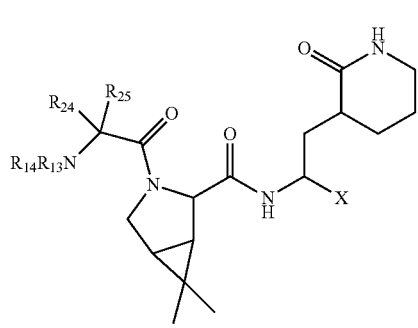
(XI-3)
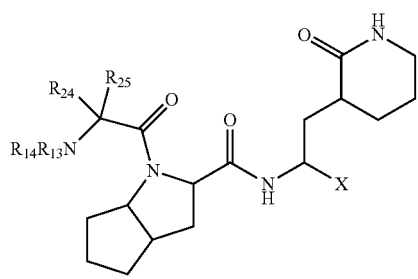
(XI-4)
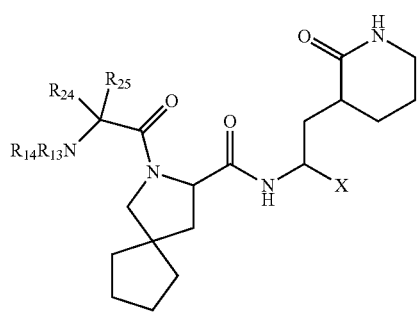
(XI-5)
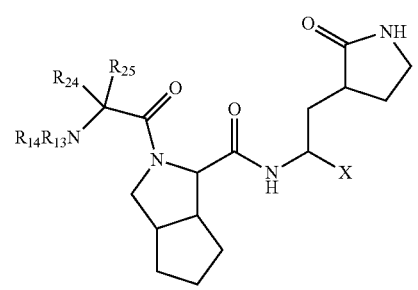
(XI-6)
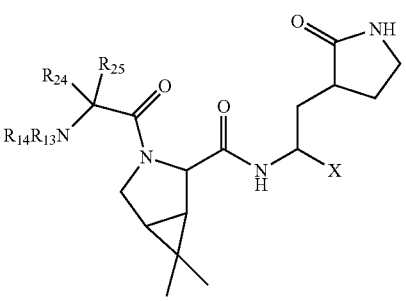
(XI-7)
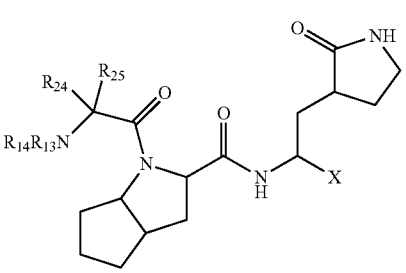
(XI-8)
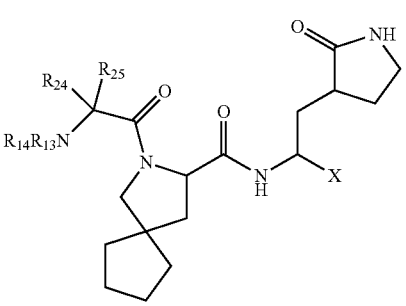
wherein $R_{13}$, $R_{14}$, $R_{24}$, $R_{25}$, and X are as previously defined.
In certain embodiments, the compound of Formula (I) is represented by one of Formulae (XII-1)~(XII-4), or a pharmaceutically acceptable salt thereof,
(XII-1)
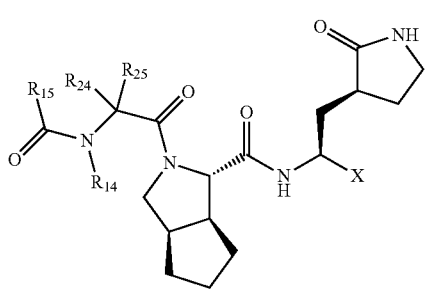
(XII-2)
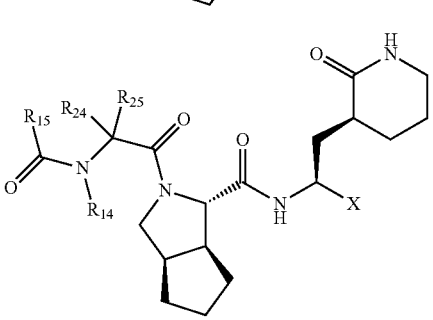

-continued (XII-3)

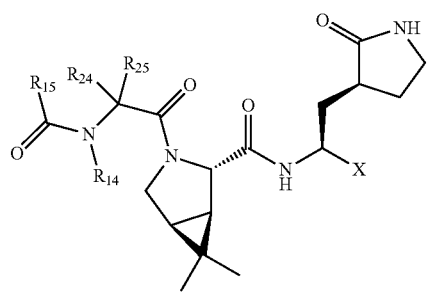

(XIII-3)

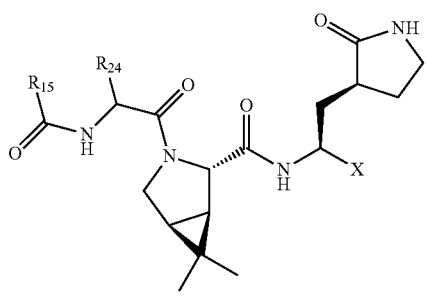

(XIII-4)

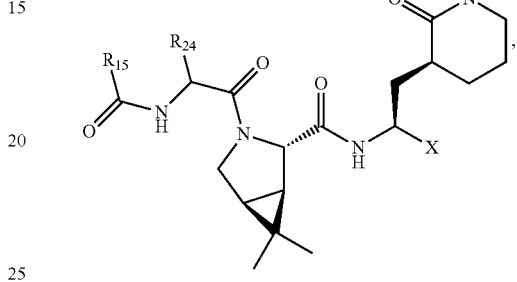

wherein $R_{15}$, $R_{24}$, and X are as previously defined. Preferably X is —CN; and $R_{24}$ is optionally substituted —$C_1$-$C_6$ alkyl, such as t-butyl.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the invention provides a method of treating or preventing a coronavirus infection in a subject, such as a human, in need thereof, comprising the step of administering to the subject a therapeutically effective amount of a compound of Formula (I) or a pharmaceutically acceptable salt thereof. The coronavirus can be an alpha, beta, gamma or delta coronavirus. In certain embodiments, the coronavirus is one which infects humans, such as coronavirus 229E, coronavirus NL63, coronavirus OC43, coronavirus HKU1, SARS-CoV-1, SARS-CoV-2, and MERS-CoV. In certain embodiments, the coronavirus is SARS-CoV-1, SARS-CoV-2, or MERS-CoV. Preferably the coronavirus is SARS-CoV-2.

Embodiments of the present invention provide administration of a compound to a healthy or virus-infected patient, either as a single agent or in combination with (1) another agent that is effective in treating or preventing coronavirus infections, (2) another agent that improves immune response and robustness, or (3) another agent that reduces inflammation and/or pain.

The compounds described herein, or salts, solvates or hydrates thereof, are believed to have activity in preventing, halting or reducing the effects of coronavirus by inhibiting the viral 3C or 3C-Like protease, thereby interfering with or (XII-4)

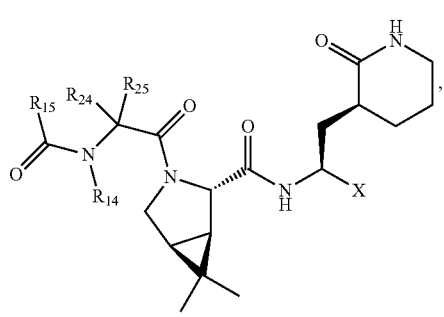

wherein $R_{14}$, $R_{15}$, $R_{24}$, $R_{25}$, and X are as previously defined.

In certain embodiments, the compound of Formula (I) is represented by one of Formulae (XIII-1)~(XIII-4), or a pharmaceutically acceptable salt thereof, (XIII-1)

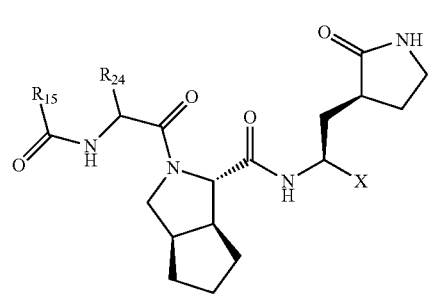

(XIII-2)

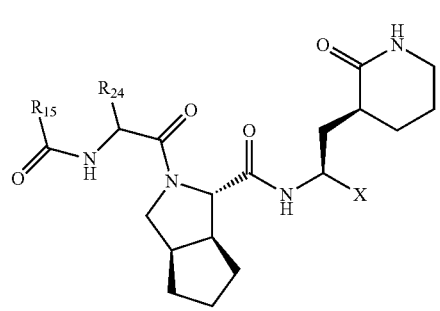

preventing the polyprotein processing of the translated viral genome, in the host cell, rendering the virus unable to replicate.

In a further aspect, this invention provides for a method of treating a respiratory disorder in a subject in need thereof, comprising administering to the subject a therapeutically effective amount of a compound of Formula (I) or a pharmaceutically acceptable salt thereof. Such respiratory disorders include, but are not limited to, an acute airway disease or a chronic airway disease. Examples of such respiratory disorders include acute asthma, lung disease secondary to environmental exposures, acute lung infection, and chronic lung infection.

The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating a coronavirus infection in an individual in need thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_2$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O—heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH— heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)— heteroaryl, —S(O)-heterocycloalkyl, —$SO_2NH_2$, —$SO_2NH$—$C_1$-$C_2$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$- alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and N02. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antituberculosis agents, and antiviral agents, including those listed at https://www.drugs.com/drug-class/anti-infectives.html. In general, combination therapy is typically preferred over alternation therapy because it induces multiple simultaneous stresses on the virus.

Although the invention has been described with respect to various preferred embodiments, it is not intended to be limited thereto, but rather those skilled in the art will recognize that variations and modifications may be made therein which are within the spirit of the invention and the scope of the appended claims.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH for acetic acid; $Boc_2O$ for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or $(i-Pr)_2EtN$ for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; $Et_2O$ for diethyl ether; HATU for O-(7-azabenzotriazol-2-yl)-N,N,N',N',-tetramethyluronium Hexafluorophosphate; HCl for hydrogen chloride; $K_2CO_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethylpiperidinate; MeOH for methanol; Mg for magnesium; MOM for methoxymethyl; Ms for mesyl or $—SO_2—CH_3$; NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4Cl$ for ammonium chloride; Ni for nickel; OH for hydroxyl; $OsO_4$ for osmium tetroxide; OTf for triflate; PPA for polyphophoric acid; PTSA forp-toluenesulfonic acid; PPTS for pyridiniump-toluenesulfonate; TBAF for tetrabutylammonium fluoride; TEA or $Et_3N$ for triethylamine; TES for triethylsilyl; TESCI for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or $PPh_3$ for triphenyl-phosphine; Tos or Ts for tosyl or $—SO_2—C_6H_4CH_3$; $Ts_2O$ for tolylsulfonic anhydride or tosyl-anhydride; TsOH for p-tolylsulfonic acid; Pd for palladium; Ph for phenyl; $Pd_2(dba)_3$ for tris(dibenzylideneacetone) dipalladium (0); $Pd(PPh_3)_4$ for tetrakis(triphenylphosphine)-palladium (0); $PdCl_2(PPh_3)_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; and TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction Scheme 1

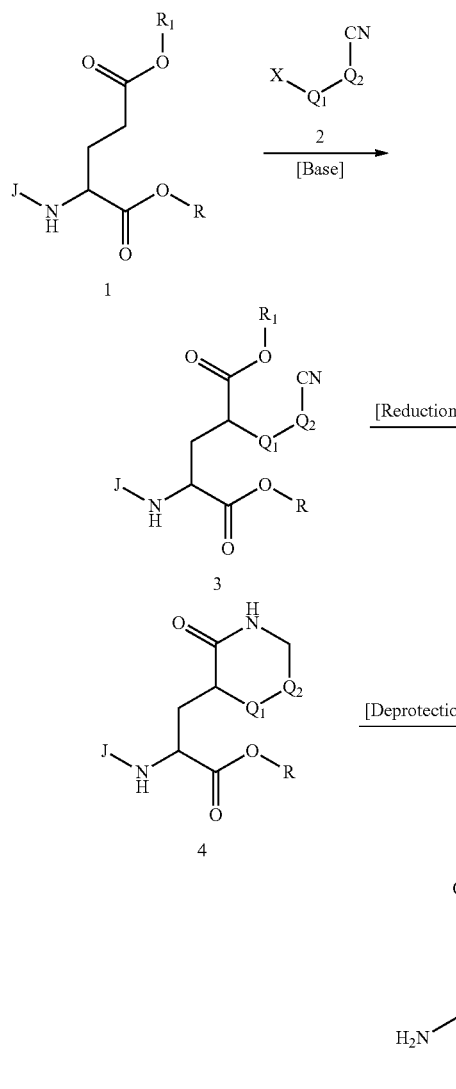

Illustrated in Scheme 1, compounds such as 5 ($Q_1$ is defined as Q, $Q_2$ is defined as Q; R defined as H, optionally substituted alkyl, optionally substituted aryl, or optionally substituted heterocyclic) can be prepared according to the illustrated synthetic methods herein, or by similar methods known to those skilled in the art. Intermediate 1 ($R_1$ defined as H, optionally substituted alkyl, optionally substituted aryl, or optionally substituted heterocyclic; J defined as an amino protecting group) can be reacted in a carbon-carbon bond forming reaction with nitrile 2 (X defined as halogen, OMs, OAc, OTf, OTs, or OTf), typically mediated by a base (denoted as [Base]) including, but not limited to: LDA, LiHMDS or LiTMP. Intermediate 3 can be reduced (denoted as [Reduction]), typically mediated by a reducing agent including, but not limited to: $LiBH_4$ or $NaBH_4$. Lactam 4 can be reacted in a deprotection step (denoted as [Deprotection]), typically mediated by an acidic reagent including, but not limited to: TFA or HCl to produce compound 5. Alternatively, lactam 4 can be reacted in a deprotection step (denoted as [Deprotection]), mediated by a reducing agent including, but not limited to hydrogen over palladium on carbon to produce compound 5.

Scheme 2

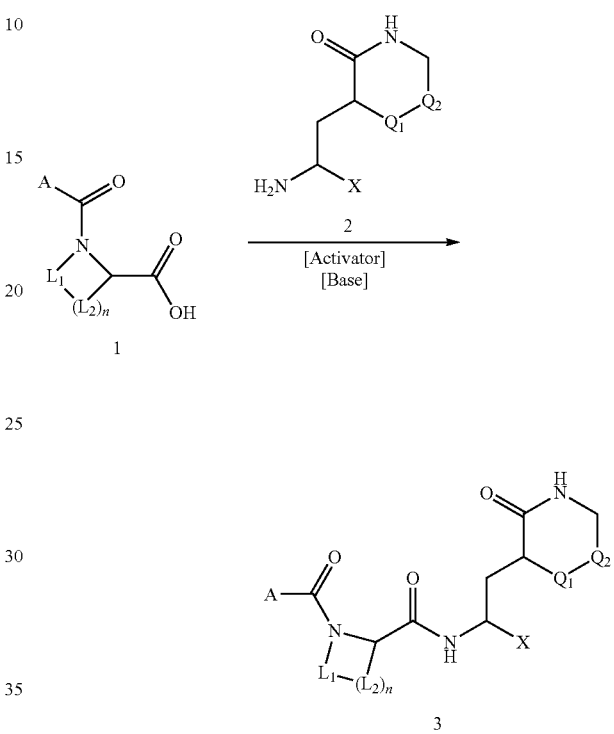

Illustrated in Scheme 2, compounds such as 3 ($Q_1$ is defined as Q, $Q_2$ is defined as Q A, $L_1$, and $L_2$, as defined previously) can be prepared according to the illustrated synthetic methods herein, or by similar methods known to those skilled in the art. Acid 1 can be reacted in a coupling reaction with amine 2 (X as defined previously), typically mediated by a base (denoted as [Base]) including, but not limited to: DIPEA, $Et_3N$, or DBU and an activator (denoted as [Activator]) including, but not limited to: HATU or EDC.

Scheme 3

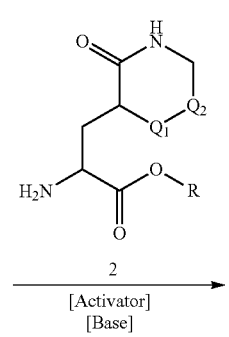

83

-continued

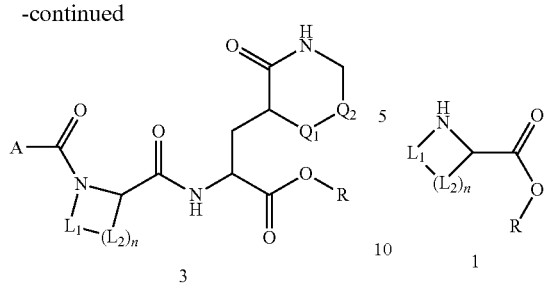

3

Illustrated in Scheme 3, compounds such as 3 ($Q_1$ is defined as Q, $Q_2$ is defined as Q; A, $L_1$, and $L_2$ as defined previously; R defined as H, optionally substituted alkyl, optionally substituted aryl, or optionally substituted heterocyclic) can be prepared according to the illustrated synthetic methods herein, or by similar methods known to those skilled in the art.

Acid 1 can be reacted in a coupling reaction with amine 2, typically mediated by a base (denoted as [Base]) including, but not limited to: DIPEA, $Et_3N$, or DBU and an activator (denoted as [Activator]) including, but not limited to: HATU or EDC.

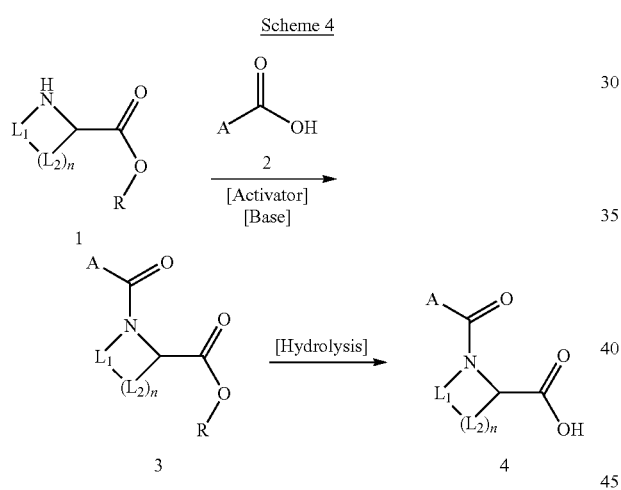

Illustrated in Scheme 4, compounds such as 4 (A, $L_1$, and $L_2$ as defined previously) can be prepared according to the illustrated synthetic methods herein, or by similar methods known to those skilled in the art. Amine 1 (R defined as H, optionally substituted alkyl, optionally substituted aryl, or optionally substituted heterocyclic) can be reacted in a coupling reaction with acid 2 (A as defined previously), typically mediated by a base (denoted as [Base]) including, but not limited to: DIPEA, $Et_3N$, or DBU and an activator (denoted as [Activator]) including, but not limited to: HATU or EDC. Ester 3 can be reacted in a hydrolysis reaction (denoted as [Hydrolysis]), typically mediated by an acidic reagent including, but not limited to: TFA or HCl to produce acid 4. Alternatively, ester 3 can be reacted in a hydrolysis reaction (denoted as [Hydrolysis]), typically mediated by a basic reagent including, but not limited to: NaOH, LiOH, or $Me_3SnOH$ to produce acid 4. Alternatively, ester 3 can be reacted in a hydrolysis reaction (denoted as [Hydrolysis]), typically mediated by a reducing agent including, but not limited to hydrogen over palladium on carbon to produce acid 4.

84

Scheme 4b

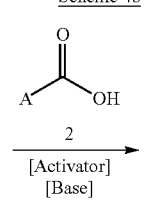

3

Illustrated in Scheme 4b, compounds such as 3 (A, $L_1$, and $L_2$ as defined previously) can be prepared according to the illustrated synthetic methods herein, or by similar methods known to those skilled in the art. Amine 1 (R defined as H, optionally substituted alkyl, optionally substituted aryl, or optionally substituted heterocyclic) can be reacted in a coupling reaction with an activated form of acid 2 (A as defined previously), of which acid activation occurs by reaction with an activator (denoted as [Activator]) to produce an intermediate activated ester intermediate. The aforementioned coupling reaction between amine 1 and an activated form of acid 2 is mediated by a base (denoted as [Base]) including, but not limited to: NaOH, $NaHCO_3$, or KOH to produce amide 3.

Scheme 5

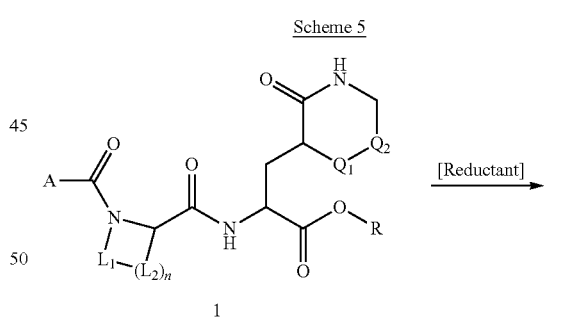

-continued

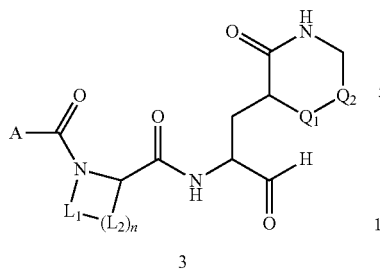

3

Illustrated in Scheme 5, compounds such as 3 (Q$_1$ is defined as Q, Q$_2$ is defined as Q; A, L$_1$, and L$_2$ as defined previously) can be prepared according to the illustrated synthetic methods herein, or by similar methods known to those skilled in the art. Intermediate 1 (R defined as H, optionally substituted alkyl, optionally substituted aryl, or optionally substituted heterocyclic) can be reacted in a reduction reaction using a reagent (denoted as [Reductant]) including, but not limited to LiBH$_4$ or NaBH$_4$ to produce alcohol 2. This can undergo an oxidation reaction using a reagent, or group of reagents (denoted as [Oxidant]) including, but not limited to: SO$_3$-pyridine, DMP, or Ac$_2$O/DMSO to produce aldehyde 3.

Scheme 6

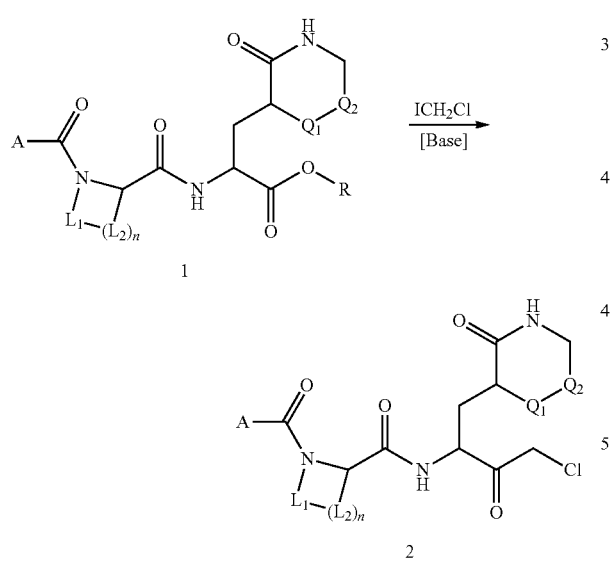

Illustrated in Scheme 6, compounds such as 2 (Q$_1$ is defined as Q, Q$_2$ is defined as Q; A, L$_1$, and L$_2$ as defined previously) can be prepared according to the illustrated synthetic methods herein, or by similar methods known to those skilled in the art. Ester 1 (R defined as H, optionally substituted alkyl, optionally substituted aryl, or optionally substituted heterocyclic) can be reacted with ICH$_2$Cl and a basic reagent (denoted as [Base]) including, but not limited to LDA or nBuLi to produce 2.

Scheme 7

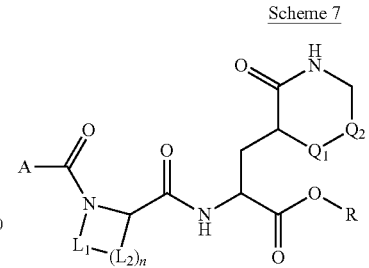 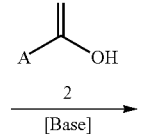

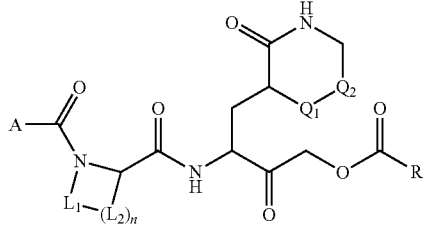

3

Illustrated in Scheme 7, compounds such as 3 (Q$_1$ is defined as Q, Q$_2$ is defined as Q; A, L$_1$, and L$_2$ as defined previously; R defined as optionally substituted alkyl, optionally substituted aryl, or optionally substituted heterocyclic) can be prepared according to the illustrated synthetic methods herein, or by similar methods known to those skilled in the art. Halide 1 can be reacted with acid 2 and a basic reagent (denoted as [Base]) including, but not limited to CsF or NaF to produce ester 3.

Scheme 8

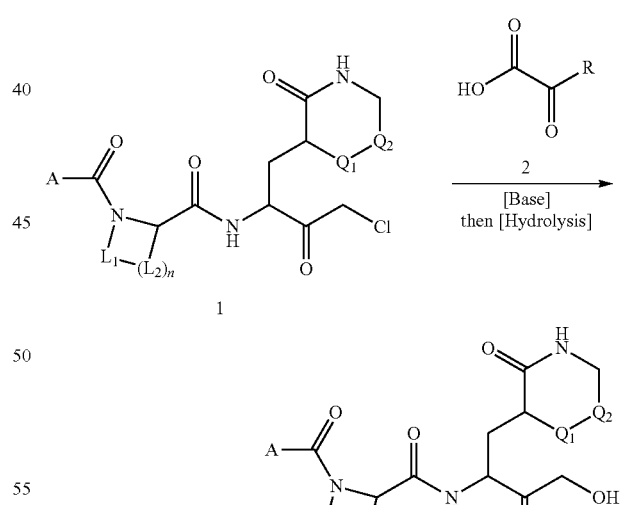

Illustrated in Scheme 8, compounds such as 3 (Q$_1$ is defined as Q, Q$_2$ is defined as Q; A, L$_1$, and L$_2$ as defined previously) can be prepared according to the illustrated synthetic methods herein, or by similar methods known to those skilled in the art. Halide 1 can be reacted with acid 2 and a basic reagent (denoted as [Base]) including, but not limited to CsF or NaF to produce an intermediate ester, which can then be reacted in a hydrolysis reaction (denoted as [Hydrolysis]) mediated by a reagent including, but not limited to: $K_2CO_3$ or $Cs_2CO_3$ to produce alcohol 3.

Scheme 9

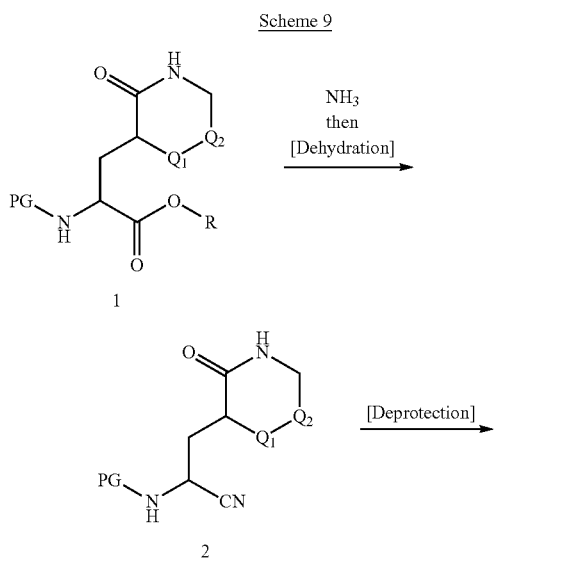

Illustrated in Scheme 9, compounds such as 3 ($Q_1$ is defined as Q, $Q_2$ is defined as Q) can be prepared according to the illustrated synthetic methods herein, or by similar methods known to those skilled in the art. Ester 1 (R defined as optionally substituted aryl or alkyl; PG defined as a nitrogen based protecting group) can be reacted with ammonia to produce an intermediate amide, which can then undergo a dehydration reaction, denoted as [Dehydration] that is mediated by a reagent including, but not limited to: $Pd(CO_2CF_3)_2$ or TFAA, to produce nitrile 2. This can undergo a deprotection reaction, denoted as [Deprotection], that is mediated by a reagent including, but not limited to: TFA, HCl, palladium, or platinum to produce primary amine 3.

Scheme 10

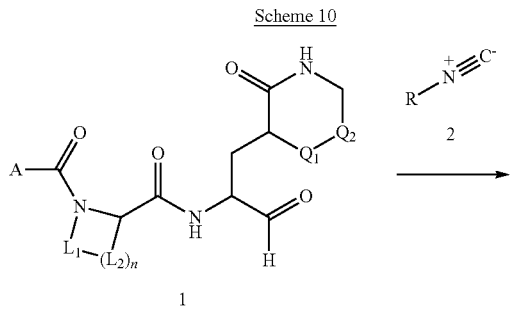

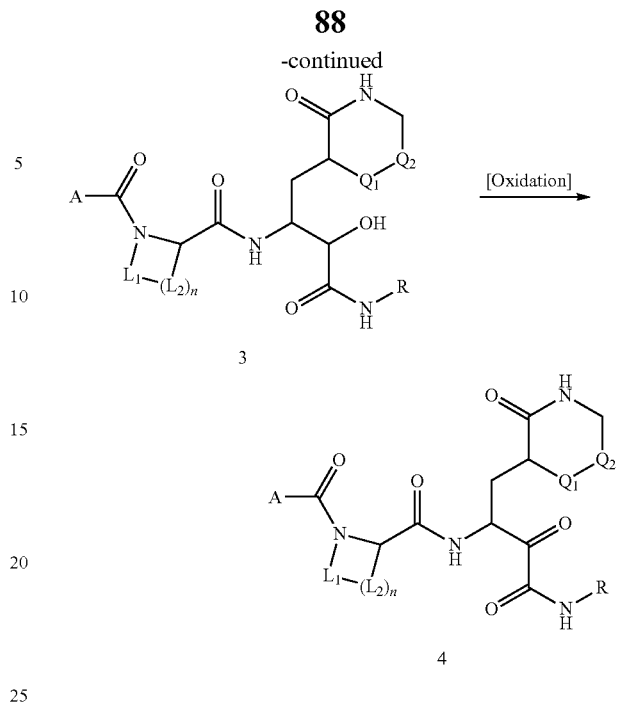

Illustrated in Scheme 10, compounds such as 4 ($Q_1$ is defined as Q, $Q_2$ is defined as Q; A, $L_1$, and $L_2$ as defined previously; R defined as optionally substituted alkyl, optionally substituted cycloalkyl, or optionally substituted heterocyclic) can be prepared according to the illustrated synthetic methods herein, or by similar methods known to those skilled in the art. Aldehyde 1 can be reacted with isonitrile 2 to form intermediate hydroxy amide 3. This intermediate can undergo an oxidation reaction, denoted as [Oxidation] that is mediated by a reagent including, but not limited to: sulfur trioxide pyridine complex (Py-$SO_3$), DMSO, oxalyl chloride, and/or acetic anhydride, to produce keto-amide 4.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. [M+H]$^+$ refers to mono-isotopic molecular weights.

NMR spectra were run on a Bruker 400 MHz spectrometer. Spectra were measured at 298K and referenced using the solvent peak. Chemical shifts for $^1$H NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Ex1: Synthesis of (1S,3aR,6aS)—N—((S)-4-chloro-3-oxo-1-((S)-2-oxopyrrolidin-3-yl)butan-2-yl)-2-(4-methoxy-1H-indole-2-carbonyl)octahydrocyclopenta[c]pyrrole-1-carboxamide

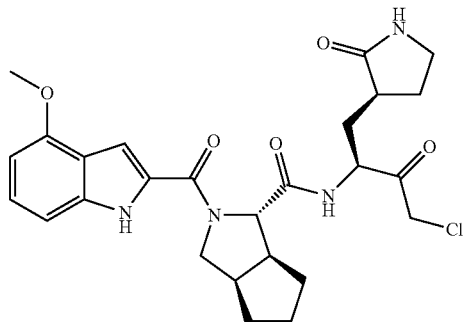 [SMILES: COc1cccc2[nH]c(C(=O)N3C[C@@H]4CCC[C@@H]4[C@H]3C(=O)N[C@@H](C[C@@H]3CCNC3=O)C(=O)CCl)cc12]

Step 1: A suspension of 4-methoxy-1H-indole-2-carboxylic acid (3.6 g) in DCM (94 mL) was cooled to 0° C. Then tert-butyl (1S,3aR,6aS)-octahydrocyclopenta[c]pyrrole-1-carboxylate oxalate (6.81 g) was added, followed by DMAP (0.690 g). Then EDC (7.22 g) was added and the reaction was allowed to stir at 0° C. for 30 minutes, then overnight at r.t. The mixture was then washed with water (1×30 mL), and the organic layer was dried over Na$_2$SO$_4$, filtered, and concentrated. The crude product was used directly in the next step.

Step 2: Trifluoroacetic acid (32.6 mL) was added to a solution of methyl (1S,3aR,6aS)-2-(4-methoxy-1H-indole-2-carbonyl)octahydrocyclopenta[c]pyrrole-1-carboxylate (7.24 g) in DCM (106 mL) at room temperature. The resulting solution was stirred at room temperature for 2 h, then concentrated. The crude residue was purified on silica gel (ethyl acetate:cyclohexane 0-100%) to provide (1S,3aR,6aS)-2-(4-methoxy-1H-indole-2-carbonyl)octahydrocyclopenta[c]pyrrole-1-carboxylic acid (4 g, 58% yield over two steps).

Step 3: A vial was charged with (S)-3-((S)-2-amino-4-chloro-3-oxobutyl)pyrrolidin-2-one hydrochloride (150 mg), DMF (3 mL), HATU (239 mg), and (1S,3aR,6aS)-2-(4-methoxy-1H-indole-2-carbonyl)octahydrocyclopenta[c]pyrrole-1-carboxylic acid (212 mg) then cooled to 0° C. Then, Hunig's base (261 mg) was added. The reaction mixture was stirred for 75 minutes, then diluted with ethyl acetate, washed three times with sat. NaHCO$_3$, water, and brine. The organic layers were dried over sodium sulfate, filtered, and concentrated. The residue was purified on silica gel to provide (1S,3aR,6aS)—N—((S)-4-chloro-3-oxo-1-((S)-2-oxopyrrolidin-3-yl)butan-2-yl)-2-(4-methoxy-1H-indole-2-carbonyl)octahydrocyclopenta[c]pyrrole-1-carboxamide as a light brown foam (195 mg, 61% yield). ESI MS m/z=516.1 [M+H]$^+$.

Ex2: Synthesis of (S)-3-((1S,3aR,6aS)-2-(4-methoxy-1H-indole-2-carbonyl)octahydrocyclopenta[c]pyrrole-1-carboxamido)-2-oxo-4-((S)-2-oxopyrrolidin-3-yl)butyl 2,6-dichlorobenzoate

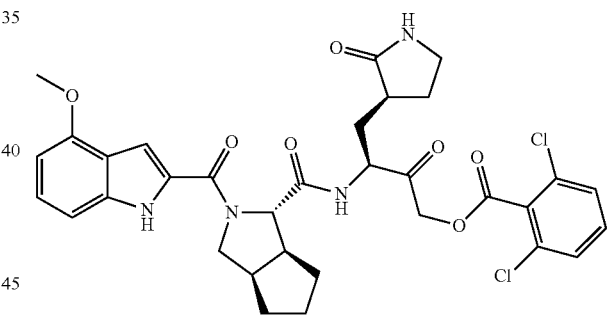

Step 1: A vial was charged with 2,6-dichlorobenzoic acid (62 mg), cesium fluoride (91 mg), and (1S,3aR,6aS)—N—((S)-4-chloro-3-oxo-1-((S)-2-oxopyrrolidin-3-yl)butan-2-yl)-2-(4-methoxy-1H-indole-2-carbonyl)octahydrocyclopenta[c]pyrrole-1-carboxamide (140 mg). The vial was purged with nitrogen gas, then DMF (2 mL) was added. The reaction mixture was heated at 65° C. for one hour. After cooling to room temperature, the reaction mixture was partitioned between ethyl acetate and water. The organic phase was washed with sat. NaHCO$_3$, water, and brine. The organic layers were concentrated and the residue was purified on silica gel to provide (S)-3-((1S,3aR,6aS)-2-(4-methoxy-1H-indole-2-carbonyl)octahydrocyclopenta[c]pyrrole-1-carboxamido)-2-oxo-4-((S)-2-oxopyrrolidin-3-yl)butyl 2,6-dichlorobenzoate (115 mg, 63% yield). ESI MS m/z=670.1 [M+H]$^+$.

Ex3: Synthesis of (1S,3aR,6aS)—N—((S)-1-cyano-2-((S)-2-oxopyrrolidin-3-yl)ethyl)-2-(4-(difluoromethoxy)-1H-indole-2-carbonyl)octahydrocyclopenta[c]pyrrole-1-carboxamide

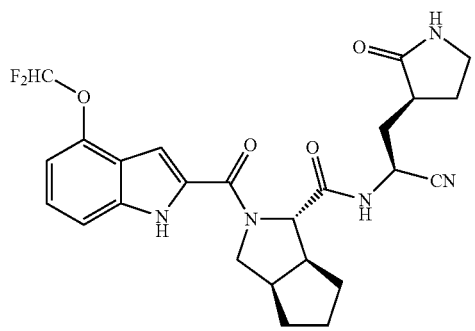 [SMILES: N#C[C@H](C[C@@H]1CCNC1=O)NC(=O)[C@@H]1[C@H]2CCC[C@H]2CN1C(=O)c1cc2c(OC(F)F)cccc2[nH]1]

Step 1: Into a 350 mL sealed tube was placed a solution of methyl (2S)-2-[(tert-butoxycarbonyl)amino]-3-[(3S)-2-oxopyrrolidin-3-yl]propanoate (25.00 g, 87.312 mmol, 1.00 equiv) in NH$_3$(g) in MeOH (250 mL, 7 mol/L). The resulting solution was stirred for 16 h at 70 degrees C. The reaction was concentrated under vacuum. The residue was purified by silica gel column (DCM/MeOH=1:0-10:1). This resulted in 15 g (63.32%) of tert-butyl N-[(1S)-1-carbamoyl-2-[(3S)-2-oxopyrrolidin-3-yl]ethyl]carbamate as a white solid.

Step 2: Into a 3-L 4-necked round-bottom flask purged and maintained with an inert atmosphere of nitrogen, was placed tert-butyl N-[(1S)-1-carbamoyl-2-[(3S)-2-oxopyrrolidin-3-yl]ethyl]carbamate (150.00 g, 552.859 mmol, 1.00 equiv), dichloroacetonitrile (607.81 g, 5528.590 mmol, 10.00 equiv) in ACN (900 mL) and water (900 mL). This was followed by the addition of Pd(CO$_2$CF$_3$)$_2$ (11.03 g, 33.172 mmol, 0.06 equiv) at room temperature. The resulting solution was stirred for 16 h at room temperature. The resulting mixture was extracted with DCM (3×600 mL). The combined organic layers were washed with brine (1×1 L), dried over anhydrous sodium sulfate. After filtration, the filtrate was concentrated under reduced pressure. The residue was applied onto a silica gel column with ethyl acetate/petroleum ether (2:1). The combined product fractions were concentrated then the residue was triturated under DCM and the resultant solid was isolated and dried under vacuum. This resulted in (51 g, 36.42%) of tert-butyl ((S)-1-cyano-2-((S)-2-oxopyrrolidin-3-yl)ethyl)carbamate as a white solid. ESI MS m/z=254.1 [M+H]$^+$. 1HNMR (CDCl$_3$) δ 6.30 (s, 1H), 5.90 (s, 1H), 4.77-4.59 (m, 1H), 3.48-3.31 (m, 2H), 2.49 (dddd, J=23.7, 11.8, 7.3, 2.7 Hz, 2H), 2.38-2.23 (m, 1H), 2.02-1.79 (m, 2H), 1.48 (s, 9H).

Step 3: Trifluoroacetic acid (790 μL) was added to a solution of tert-butyl ((S)-1-cyano-2-((S)-2-oxopyrrolidin-3-yl)ethyl)carbamate (20 mg, 0.079 mmol) and DCM (0.790 mL) at 22° C. After 15 min, the resulting solution was concentrated directly in vacuo. The residue was redissolved in methanol (2 mL) and concentrated in vacuo, then redissolved in ethyl acetate (2 mL) and concentrated once more. The crude (S)-2-amino-3-((S)-2-oxopyrrolidin-3-yl)propanenitrile 2,2,2-trifluoroacetate was used without further purification. 1HNMR (DMSO-d$_6$) δ 8.94 (bs, 2H), 4.80 (dd, J=8.7, 6.6 Hz, 1H), 3.24-3.16 (m, 2H), 2.50 (m, 1H), 2.30 (dddd, J=12.1, 8.8, 5.6, 3.4 Hz, 1H), 2.15 (ddd, J=14.5, 8.1, 6.6 Hz, 1H), 1.97-1.91 (m, 1H), 1.74 (ddt, J=12.5, 10.5, 9.0 Hz, 1H).

Step 4: 4-(difluoromethoxy)-1H-indole-2-carboxylic acid (3.5 g, 15.41 mmol) was suspended in 25 mL DCM and 4.5 mL THF. Oxalyl chloride (1.618 mL, 18.49 mmol) was then added dropwise at 22° C., followed by DMF (3 drops). After 15 minutes, the mixture had become homogenous and TLC analysis (MeOH-quenched aliquot) showed full conversion. The resulting solution was concentrated directly to afford crude 4-(difluoromethoxy)-1H-indole-2-carbonyl chloride as a red oil, which was used immediately without further purification.

Step 5: Ethyl (1S,3aR,6aS)-octahydrocyclopenta[c]pyrrole-1-carboxylate hydrochloride (9.57 g, 43.6 mmol), was suspended in EtOH (87 mL), then aqueous 5 N sodium hydroxide (37 mL, 185 mmol) was added at 22° C. with vigorous stirring. After 1 h, the ethanol was distilled in vacuo to afford ~40 mL of a viscous aqueous solution containing sodium (1S,3aR,6aS)-octahydrocyclopenta[c]pyrrole-1-carboxylate, which was used directly.

Step 6: Crude 4-(difluoromethoxy)-1H-indole-2-carbonyl chloride (2.161 g, 8.8 mmol) was dissolved in THF (5 mL) at 22° C. The aqueous solution of sodium (1S,3aR,6aS)-octahydrocyclopenta[c]pyrrole-1-carboxylate (16 mL) was then poured in at 22° C. with vigorous stirring. After 1 h of stirring 1 N HCl was added until the pH of the solution was about 1. The resulting aqueous suspension was extracted twice with DCM, then the pooled organic fractions were dried over MgSO$_4$, filtered and concentrated. The resulting oil was subjected to silica gel chromatography to afford (1S,3aR,6aS)-2-(4-(difluoromethoxy)-1H-indole-2-carbonyl)octahydrocyclopenta[c]pyrrole-1-carboxylic acid (2.67 g, 7.33 mmol, 83% yield) as a pale yellow solid. 1HNMR (DMSO-d$_6$) δ 12.64 (bs, 1H), 11.88 (s, 1H), 7.38-7.29 (m, 1H), 7.20 (m, 1H), 7.00-6.95 (m, 1H), 6.82 (m, 1H), 4.36 (d, J=3.6 Hz, 1H), 4.13 (dd, J=10.5, 8.2 Hz, 1H), 3.81 (dd, J=10.5, 4.3 Hz, 1H), 3.70 (m, 1H), 2.90-2.79 (m, 1H), 2.64 (m, 1H), 2.02-1.90 (m, 1H), 1.88-1.66 (m, 3H), 1.58 (m, 4H).

Step 7: HATU (69.6 mg, 0.183 mmol) was added to a solution of (1S,3aR,6aS)-2-(4-(difluoromethoxy)-1H-indole-2-carbonyl)octahydrocyclopenta[c]pyrrole-1-carboxylic acid (57.8 mg, 0.159 mmol), (S)-2-amino-3-((S)-2-oxopyrrolidin-3-yl)propanenitrile 2,2,2-trifluoroacetate (32.6 mg, 0.122 mmol), DMF (0.407 mL), and Et$_3$N (150 μl, 1.08 mmol) at 22° C. The resulting solution was stirred for 24 h at 22° C., then purified directly via RPHPLC to afford (1S,3aR,6aS)—N—((S)-1-cyano-2-((S)-2-oxopyrrolidin-3-yl)ethyl)-2-(4-(difluoromethoxy)-1H-indole-2-carbonyl)octahydrocyclopenta[c]pyrrole-1-carboxamide as a white solid (2 mg). ESI MS m/z=500.1 [M+H]$^+$.

Ex4: Synthesis of (1S,3aR,6aS)—N—((S)-1-cyano-2-((S)-2-oxopyrrolidin-3-yl)ethyl)-2-(4-methoxy-1H-indole-2-carbonyl)octahydrocyclopenta[c]pyrrole-1-carboxamide

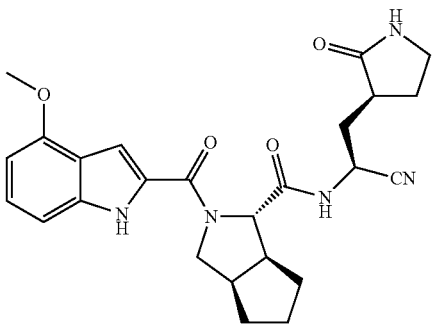 [SMILES: COc1cccc2[nH]c(C(=O)N3C[C@@H]4CCC[C@@H]4[C@H]3C(=O)N[C@H](C#N)C[C@@H]3CCNC3=O)cc12]

The synthesis of Ex4 was of a similar nature as the synthesis of Ex3, with the following changes:
1. 4-methoxy-1H-indole-2-carboxylic acid was used in place of 4-(difluoromethoxy)-1H-indole-2-carboxylic acid in Step 4.

Characterization data for Ex4 was obtained: ESI MS m/z=464.1 [M+H]$^+$. 1HNMR (Chloroform-d) δ 9.77 (s, 1H), 8.18 (d, J=7.1 Hz, 1H), 7.22 (t, J=8.1 Hz, 1H), 7.11-7.00 (m, 2H), 6.76 (s, 1H), 6.50 (d, J=7.7 Hz, 1H), 4.92 (t, J=8.3 Hz, 1H), 4.54 (d, J=3.2 Hz, 1H), 4.24 (t, J=9.4 Hz, 1H), 3.96 (s, 3H), 3.84 (dd, J=10.8, 4.8 Hz, 1H), 3.32 (m, 2H), 3.04 (m, 1H), 2.87 (m, 1H), 2.65 (m, 1H), 2.33 (m, 2H), 2.11-1.50 (m, 10H).

Ex5: Synthesis of (1S,3aR,6aS)-2-(4-(difluoromethoxy)-1H-indole-2-carbonyl)-N—((S)-1-oxo-3-((S)-2-oxopyrrolidin-3-yl)propan-2-yl)octahydrocyclopenta[c]pyrrole-1-carboxamide

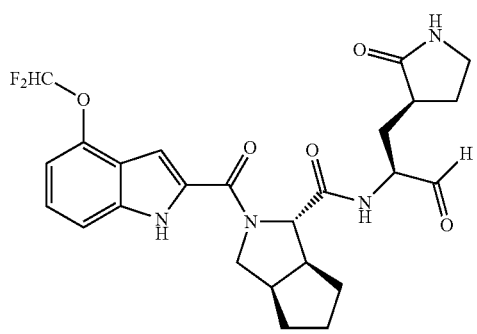 [SMILES: O=C[C@H](C[C@@H]1CCNC1=O)NC(=O)[C@@H]1[C@H]2CCC[C@H]2CN1C(=O)c1cc2c(OC(F)F)cccc2[nH]1]

Step 1: Methyl (S)-2-amino-3-((S)-2-oxopyrrolidin-3-yl)propanoate hydrochloride (0.880 g, 3.95 mmol) and (1S,3aR,6aS)-2-(4-(difluoromethoxy)-1H-indole-2-carbonyl)octahydrocyclopenta[c]pyrrole-1-carboxylic acid (1.01 g, 2.77 mmol) were dissolved in a mixture of DMF and DCM (1:1 v/v, 26 mL), and the resulting solution was cooled to 0° C. under a nitrogen atmosphere. HATU (1.126 g, 2.96 mmol) then was added in one portion. After 3 min of stirring, added Hunig's base (1.656 mL, 9.48 mmol) dropwise. After stirring for 30 min at 0° C., precooled 1 N HCl (15 mL) was added, followed by water (40 mL). The resulting mixture was extracted with DCM twice. The pooled organic fractions were twice washed with saturated aqueous NaHCO$_3$, then brine, then dried over MgSO$_4$ and concentrated. The resulting brown oil was subjected to silica gel chromatography to afford methyl (S)-2-((1S,3aR,6aS)-2-(4-(difluoromethoxy)-1H-indole-2-carbonyl)octahydrocyclopenta[c]pyrrole-1-carboxamido)-3-((S)-2-oxopyrrolidin-3-yl)propanoate (1.42 g, 2.67 mmol, 96% yield) as a white foam. 1HNMR (Chloroform-d) δ 9.87 (s, 1H), 7.85 (d, J=7.2 Hz, 1H), 7.29 (d, J=8.2 Hz, 1H), 7.20 (d, J=8.0 Hz, 1H), 6.97 (s, 1H), 6.90-6.45 (m, 3H), 6.01 (s, 1H), 4.63 (app s, 1H), 4.56 (m, 1H), 4.22 (t, J=9.4 Hz, 1H), 3.80 (dd, J=10.5, 4.6 Hz, 1H), 3.73 (m, 4H), 3.26 (m, 2H), 3.00 (m, 1H), 2.86 (m, 1H), 2.55 (m, 1H), 2.41-2.30 (m, 1H), 2.23-2.11 (m, 1H), 2.04 (m, 2H), 1.98-1.85 (m, 3H), 1.85-1.72 (m, 3H), 1.48 (m, 2H), 1.43 (m, 1H).

Step 2: Methyl (S)-2-((1S,3aR,6aS)-2-(4-(difluoromethoxy)-1H-indole-2-carbonyl)octahydrocyclopenta[c]pyrrole-1-carboxamido)-3-((S)-2-oxopyrrolidin-3-yl)propanoate (1.42 g, 2.67 mmol) was dissolved in THF (26.7 mL) and cooled to 0° C. with stirring under a nitrogen atmosphere. Lithium borohydride (2 M in THF, 6.67 mL, 13.33 mmol) was then added dropwise over 4-5 min. After 40 min at 0° C., 1 M HCl (1 eq, 13.5 mL) was then slowly added over 5 min. The resulting turbid solution was partitioned between EtOAc and water and the phases were separated. The aqueous phase was extracted thrice with EtOAc, and the pooled organic fractions were dried over MgSO$_4$ and concentrated. The residue was subjected to silica gel chromatography to afford (1S,3aR,6aS)-2-(4-(difluoromethoxy)-1H-indole-2-carbonyl)-N—((S)-1-hydroxy-3-((S)-2-oxopyrrolidin-3-yl)propan-2-yl)octahydrocyclopenta[c]pyrrole-1-carboxamide (965 mg, 1.913 mmol, 71.7% yield) as white solid. 1HNMR (Chloroform-d) δ 10.45 (s, 1H), 7.95 (d, J=8.0 Hz, 1H), 7.29 (app d, J=8.3 Hz, 1H), 7.19 (t, J=8.0 Hz, 1H), 6.99 (s, 1H), 6.85-6.47 (m, 2H), 6.12 (s, 1H), 4.51 (d, J=3.4 Hz, 1H), 4.27 (t, J=9.4 Hz, 1H), 4.01 (m, 1H), 3.74 (td, J=11.1, 4.3 Hz, 2H), 3.61 (dd, J=11.6, 4.2 Hz, 1H), 3.22 (m, 2H), 3.06-2.93 (m, 1H), 2.75 (m, 1H), 2.60-2.50 (m, 1H), 2.34 (m, 1H), 2.17 (m, 3H), 1.95-1.83 (m, 3H), 1.83-1.67 (m, 3H), 1.67-1.45 (m, 5H).

Step 3: (1S,3aR,6aS)-2-(4-(difluoromethoxy)-1H-indole-2-carbonyl)-N—((S)-1-hydroxy-3-((S)-2-oxopyrrolidin-3-yl)propan-2-yl)octahydrocyclopenta[c]pyrrole-1-carboxamide (0.958 g, 1.899 mmol) was dissolved in DCM (12.66 mL), then cooled to 0° C. under a nitrogen atmosphere. Dess-Martin periodinane (1.127 g, 2.66 mmol) was then added in one portion. After 1 h, saturated aqueous Na$_2$S$_2$O$_3$ was poured into the resulting brown suspension. The phases were separated and the organic phase was washed with saturated aqueous NaHCO$_3$, then brine, then dried over MgSO$_4$ and concentrated. The residue was then subjected to silica gel chromatography, eluting with DCM/MeOH. Fractions containing the product were concentrated, and the resulting brown foam was then subjected to silica gel chromatography a second time, eluting with MTBE/acetone, to afford (1S,3aR,6aS)-2-(4-(difluoromethoxy)-1H-indole-2-carbonyl)-N—((S)-1-oxo-3-((S)-2-oxopyrrolidin-3-yl)propan-2-yl)octahydrocyclopenta[c]pyrrole-1-carboxamide (390 mg, 0.776 mmol, 40.9% yield) as a colorless foam. 1HNMR (Chloroform-d) δ 9.82 (s, 1H), 9.52 (s, 1H), 8.42 (s, 1H), 7.28 (app d, J=8.4 Hz, 1H), 7.21 (t, J=7.9 Hz, 1H), 7.02 (s, 1H), 6.87-6.43 (m, 3H), 5.90 (s, 1H), 4.69 (s, 1H), 4.35 (s, 1H), 4.26 (t, J=9.4 Hz, 1H), 3.82 (dd, J=10.3, 4.6 Hz, 1H), 3.49 (s, 1H), 3.28 (m, 2H), 2.99 (s, 1H), 2.87 (s, 1H), 2.54 (s, 1H), 2.34 (m, 1H), 2.11-1.49 (m, 17H). ESI MS m/z=503.1 [M+H]$^+$.

Ex6: Synthesis of (1S,3aR,6aS)-2-(4-methoxy-1H-indole-2-carbonyl)-N—((S)-1-oxo-3-((S)-2-oxopyrrolidin-3-yl)propan-2-yl)octahydrocyclopenta[c]pyrrole-1-carboxamide

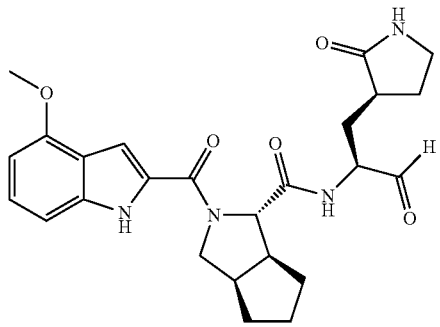 [SMILES: COc1cccc2[nH]c(C(=O)N3C[C@@H]4CCC[C@@H]4[C@H]3C(=O)N[C@H](C=O)C[C@@H]3CCNC3=O)cc12]

The synthesis of Ex6 was of a similar nature as the synthesis of Ex5, with the following changes:
1. (1S,3aR,6aS)-2-(4-(methoxy)-1H-indole-2-carbonyl)octahydrocyclopenta[c]pyrrole-1-carboxylic acid was used in place of (1S,3aR,6aS)-2-(4-(difluoromethoxy)-1H-indole-2-carbonyl)octahydrocyclopenta[c]pyrrole-1-carboxylic acid in Step 1.

Characterization data for Ex6 was obtained: ESI MS m/z=464.1 [M+H]$^+$.

Ex7: Synthesis of (1S,3aR,6aS)—N—((S)-1-cyano-2-((S)-2-oxopiperidin-3-yl)ethyl)-2-(4-methoxy-1H-indole-2-carbonyl)octahydrocyclopenta[c]pyrrole-1-carboxamide

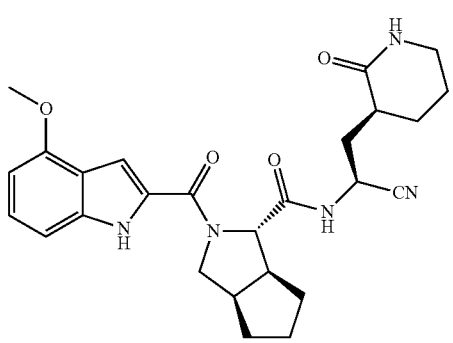 [SMILES: COc1cccc2[nH]c(C(=O)N3C[C@@H]4CCC[C@@H]4[C@H]3C(=O)N[C@H](C#N)C[C@@H]3CCCNC3=O)cc12]

Step 1: A flask was charged with dimethyl (tert-butoxycarbonyl)-L-glutamate (6.5 g) and THF (70 mL). The flask was cooled to −78° C. under a nitrogen atmosphere. Then LiHMDS (52 mL, 1 M in THF) was added over 5 min. After 1 h, 3-bromopropanenitrile (3 mL) was added dropwise. After 90 minutes, the reaction mixture was warmed to −55° C., then quenched with aq. NH$_4$Cl. The reaction mixture was allowed to reach rt, then diluted with 20 mL water. The product was extracted with MTBE then concentrated. An additional 30 mL of MTBE was added, by which a precipitate formed. This was filtered off and the filtrate was concentrated to provide an orange oil that was used directly in the next step.

Step 2: A flask was charged with cobalt(II) chloride hexahydrate (2.8 g). Then a solution of product from Step 1 in THF (20 mL) was transferred to this flask with MeOH washings (140 mL). The flask was cooled to 0° C., then sodium borohydride (3.6 g) was added over 20 min. The reaction was allowed to reach rt and stirred for 24 h. Then, most of the volatiles were removed under reduced pressure. EtOAc (100 mL) and 1 M HCl (40 mL) were added. The product was extracted with EtOAc, and the combined organic layers were washed with 1 M HCl, brine, then concentrated. The residue was purified on silica gel to provide methyl (S)-2-((tert-butoxycarbonyl)amino)-3-((S)-2-oxopiperidin-3-yl)propanoate (1.4 g, 20% over two steps). ESI MS m/z=301.1 [M+H]$^+$.

Step 3: A flask was charged with methyl (S)-2-((tert-butoxycarbonyl)amino)-3-((S)-2-oxopiperidin-3-yl)propanoate (421 mg) and then 4 M ammonia in MeOH (2.8 mL) was added. The reaction mixture was stirred for 72 h, then heated to 65° C. for 1.5 h. The volatiles were removed, and the residue was purified on silica gel to provide tert-butyl ((S)-1-amino-1-oxo-3-((S)-2-oxopiperidin-3-yl)propan-2-yl)carbamate (237 mg). This was added to a flask containing Pd(CO$_2$CF$_3$)$_2$ (28 mg) and MeCN (5 mL). Then, water (2 mL) and 2,2-dichloroacetonitrile (1.3 mL) were added. After purging with nitrogen gas, the flask was heated to 60° C. for 2 h. The reaction mixture was diluted with EtOAc, washed with water, then washed with brine. The organic extract was concentrated and the residue was purified on silica gel to provide tert-butyl ((S)-1-cyano-2-((S)-2-oxopiperidin-3-yl)ethyl)carbamate (88 mg).

Step 4: A vial was charged with tert-butyl ((S)-1-cyano-2-((S)-2-oxopiperidin-3-yl)ethyl)carbamate (88 mg) and DCM (1 mL). Then, TFA (2 mL) was added. After 1 h, the volatiles were removed and the product, (S)-2-amino-3-((S)-2-oxopiperidin-3-yl)propanenitrile 2,2,2-trifluoroacetate, was used without further purification.

Step 5: A vial was charged with (1S,3aR,6aS)-2-(4-methoxy-1H-indole-2-carbonyl)octahydrocyclopenta[c]pyrrole-1-carboxylic acid (50 mg), (S)-2-amino-3-((S)-2-oxopiperidin-3-yl)propanenitrile 2,2,2-trifluoroacetate (20 mg), DMF (1 mL), and DIPEA (0.1 mL). Then HATU (40 mg) was added. After 30 min, the reaction mixture was purified by RPHPLC to provide the product, (1S,3aR,6aS)—N—((S)-1-cyano-2-((S)-2-oxopiperidin-3-yl)ethyl)-2-(4-methoxy-1H-indole-2-carbonyl)octahydrocyclopenta[c]pyrrole-1-carboxamide (3 mg). ESI MS m/z=478.1 [M+H]$^+$.

Ex8: Synthesis of (1S,3aR,6aS)—N—((S)-4-(cyclohexylamino)-3,4-dioxo-1-((S)-2-oxopyrrolidin-3-yl)butan-2-yl)-2-(4-(difluoromethoxy)-1H-indole-2-carbonyl)octahydrocyclopenta[c]pyrrole-1-carboxamide

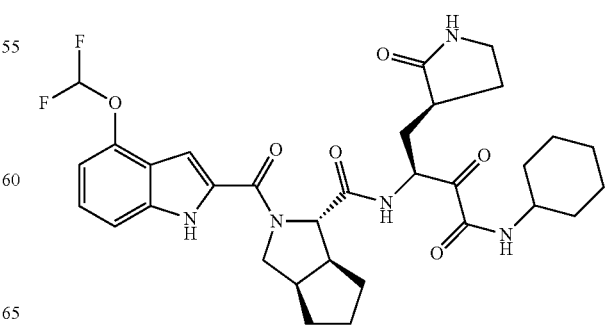

Step 1: A vial was charged with (1S,3aR,6aS)-2-(4-(difluoromethoxy)-1H-indole-2-carbonyl)-N—((S)-1-oxo-3-((S)-2-oxopyrrolidin-3-yl)propan-2-yl)octahydrocyclopenta[c]pyrrole-1-carboxamide (58 mg) and DCM (1 mL). The flask was cooled to 0° C. under a nitrogen atmosphere. Then acetic acid (0.3 mL) was added as a solution in DCM (1 mL). Then isocyanocyclohexane (0.3 mL) was added and the reaction was allowed to reach room temperature. After 2 h, the volatiles were removed. The residue was dissolved in MeOH (1 mL) and cooled to −40° C. Potassium carbonate (23 mg) was added, and the reaction was warmed to 0° C. Then water (0.2 mL) was added followed by 3M Aq. HCl (0.5 mL). The product was extracted with ethyl acetate and concentrated. The residue was purified on silica gel to provide the product, (1S,3aR,6aS)—N-((2S)-4-(cyclohexylamino)-3-hydroxy-4-oxo-1-((S)-2-oxopyrrolidin-3-yl)butan-2-yl)-2-(4-(difluoromethoxy)-1H-indole-2-carbonyl)octahydrocyclopenta[c]pyrrole-1-carboxamide (39 mg). ESI MS m/z=630.1 [M+H]⁺.

Step 2: A vial was charged with (1S,3aR,6aS)—N-((2S)-4-(cyclohexylamino)-3-hydroxy-4-oxo-1-((S)-2-oxopyrrolidin-3-yl)butan-2-yl)-2-(4-(difluoromethoxy)-1H-indole-2-carbonyl)octahydrocyclopenta[c]pyrrole-1-carboxamide (39 mg), DCM (1 mL), and Hunig's base (0.033 mL) at 0° C. Py-SO₃ (30 mg) was added as a solution in DMSO (1 mL). An additional portion of Hunig's base (0.033 mL) and Py-SO₃ (30 mg) in DMSO (1 mL) was added. The reaction mixture was diluted with ethyl acetate and water. The organic layer was removed and aqueous layer was extracted with ethyl acetate. The combined organics were concentrated and the residue was twice crystallized from diethyl ether:THF to provide the product, (1S,3aR,6aS)—N—((S)-4-(cyclohexylamino)-3,4-dioxo-1-((S)-2-oxopyrrolidin-3-yl)butan-2-yl)-2-(4-(difluoromethoxy)-1H-indole-2-carbonyl)octahydrocyclopenta[c]pyrrole-1-carboxamide (2 mg). ESI MS m/z=628.1 [M+H]⁺.

Ex9: Synthesis of (1S,3aR,6aS)—N—((S)-4-(cyclohexylamino)-3,4-dioxo-1-((S)-2-oxopyrrolidin-3-yl)butan-2-yl)-2-(4-methoxy-1H-indole-2-carbonyl)octahydrocyclopenta[c]pyrrole-1-carboxamide

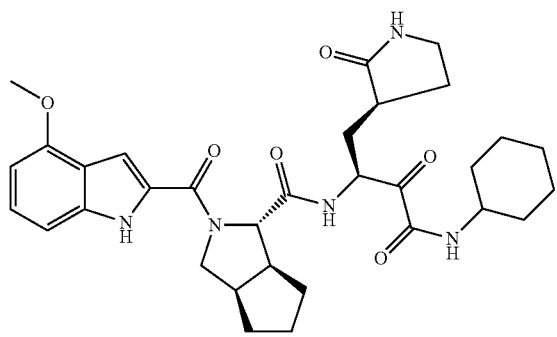 [SMILES: COc1cccc2[nH]c(C(=O)N3C[C@@H]4CCC[C@@H]4[C@H]3C(=O)N[C@@H](C[C@@H]3CCNC3=O)C(=O)C(=O)NC3CCCCC3)cc12]

The synthesis of Ex9 was of a similar nature as the synthesis of Ex8, with the following changes:
1. (1S,3aR,6aS)-2-(4-methoxy-1H-indole-2-carbonyl)-N—((S)-1-oxo-3-((S)-2-oxopyrrolidin-3-yl)propan-2-yl)octahydrocyclopenta[c]pyrrole-1-carboxamide was used in place of (1S,3aR,6aS)-2-(4-(difluoromethoxy)-1H-indole-2-carbonyl)-N—((S)-1-oxo-3-((S)-2-oxopyrrolidin-3-yl)propan-2-yl)octahydrocyclopenta[c]pyrrole-1-carboxamide in Step 1.

Characterization data for Ex9 was obtained: ESI MS m/z=592.1 [M+H]⁺.

Ex10: Synthesis of (1S,3aR,6aS)—N—((S)-4-hydroxy-3-oxo-1-((S)-2-oxopyrrolidin-3-yl)butan-2-yl)-2-(4-methoxy-1H-indole-2-carbonyl)octahydrocyclopenta[c]pyrrole-1-carboxamide

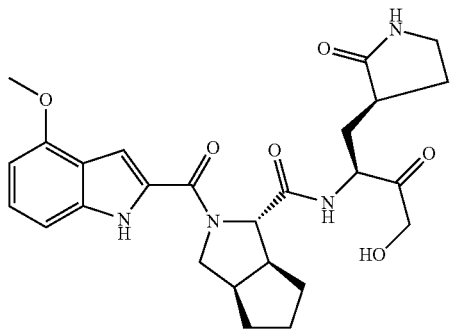 [SMILES: COc1cccc2[nH]c(C(=O)N3C[C@@H]4CCC[C@@H]4[C@H]3C(=O)N[C@@H](C[C@@H]3CCNC3=O)C(=O)CO)cc12]

Step 1: A vial was charged with (1S,3aR,6aS)—N—((S)-4-chloro-3-oxo-1-((S)-2-oxopyrrolidin-3-yl)butan-2-yl)-2-(4-methoxy-1H-indole-2-carbonyl)octahydrocyclopenta[c]pyrrole-1-carboxamide (99 mg), cesium fluoride (67 mg), 2-oxo-2-phenylacetic acid (38 mg), and DMF (2 mL). The flask was heated to 65° C. for 75 min. After cooling to room temperature, the reaction mixture was partitioned between ethyl acetate and water. The product was extracted with ethyl acetate and the combined organics were concentrated. The product, (S)-3-((1S,3aR,6aS)-2-(4-methoxy-1H-indole-2-carbonyl)octahydrocyclopenta[c]pyrrole-1-carboxamido)-2-oxo-4-((S)-2-oxopyrrolidin-3-yl)butyl 2-oxo-2-phenylacetate, was used in the next step without any further purification.

Step 2: A vial was charged with (S)-3-((1S,3aR,6aS)-2-(4-methoxy-1H-indole-2-carbonyl)octahydrocyclopenta[c]pyrrole-1-carboxamido)-2-oxo-4-((S)-2-oxopyrrolidin-3-yl)butyl 2-oxo-2-phenylacetate (121 mg) and MeOH (3 mL). Then, potassium carbonate (27 mg) was added. After 1 h, 1 M aq. HCl was added (0.5 mL). The reaction mixture was filtered and concentrated. The residue was purified by RPHPLC to provide the product, (1S,3aR,6aS)—N—((S)-4-hydroxy-3-oxo-1-((S)-2-oxopyrrolidin-3-yl)butan-2-yl)-2-(4-methoxy-1H-indole-2-carbonyl)octahydrocyclopenta[c]pyrrole-1-carboxamide (3 mg). ESI MS m/z=497.1 [M+H]⁺.

Ex11: Synthesis of (1S,2S,5R)—N—((S)-1-cyano-2-((S)-2-oxopyrrolidin-3-yl)ethyl)-3-(4-(difluoromethoxy)-1H-indole-2-carbonyl)-6,6-dimethyl-3-azabicyclo[3.1.0]hexane-2-carboxamide

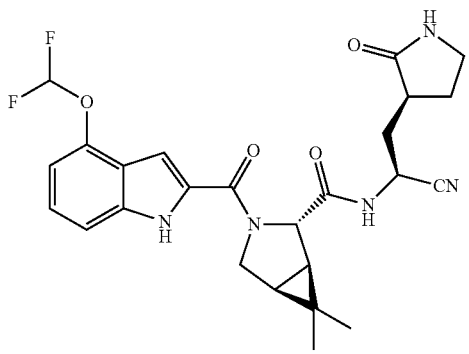 [SMILES: CC1(C)[C@@H]2[C@@H](C(=O)N[C@H](C#N)C[C@@H]3CCNC3=O)N(C(=O)c3cc4c(OC(F)F)cccc4[nH]3)C[C@@H]21]

The synthesis of Ex11 was of a similar nature as the synthesis of Ex3, with the following changes:

1. (1S,2S,5R)-3-(4-(difluoromethoxy)-1H-indole-2-carbonyl)-6,6-dimethyl-3-azabicyclo[3.1.0]hexane-2-carboxylic acid was used in place of (1S,3aR,6aS)-2-(4-(difluoromethoxy)-1H-indole-2-carbonyl)octahydrocyclopenta[c]pyrrole-1-carboxylic acid in Step 7.

Characterization data for Ex11 was obtained: ESI MS m/z=500.1 [M+H]+.

Ex12: Synthesis of (S)—N—((S)-1-cyano-2-((S)-2-oxopyrrolidin-3-yl)ethyl)-1-(4-(difluoromethoxy)-1H-indole-2-carbonyl)pyrrolidine-2-carboxamide

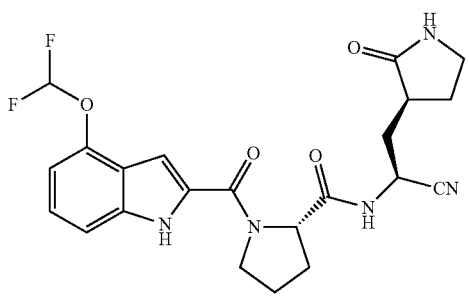 [SMILES: N#C[C@H](C[C@@H]1CCNC1=O)NC(=O)[C@@H]1CCCN1C(=O)c1cc2c(OC(F)F)cccc2[nH]1]

The synthesis of Ex12 was of a similar nature as the synthesis of Ex3, with the following changes:

1. (4-(difluoromethoxy)-1H-indole-2-carbonyl)-L-proline was used in place of (1S,3aR,6aS)-2-(4-(difluoromethoxy)-1H-indole-2-carbonyl)octahydrocyclopenta[c]pyrrole-1-carboxylic acid in Step 7.

Characterization data for Ex12 was obtained: ESI MS m/z=460.1 [M+H]+.

Ex13: Synthesis of (1S,3aR,6aS)—N—((S)-1-cyano-2-((S)-2-oxopyrrolidin-3-yl)ethyl)-2-(4,6-difluoro-1H-indole-2-carbonyl)octahydrocyclopenta[c]pyrrole-1-carboxamide

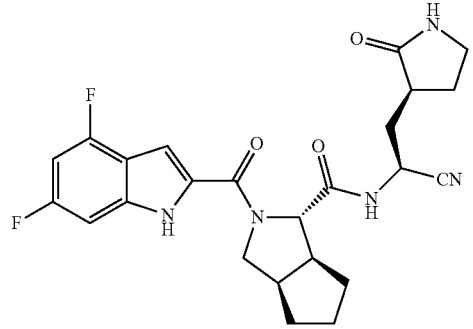 [SMILES: N#C[C@H](C[C@@H]1CCNC1=O)NC(=O)[C@@H]1[C@H]2CCC[C@H]2CN1C(=O)c1cc2c(F)cc(F)cc2[nH]1]

The synthesis of Ex13 was of a similar nature as the synthesis of Ex3, with the following changes:

1. (1S,3aR,6aS)-2-(4,6-difluoro-1H-indole-2-carbonyl)octahydrocyclopenta[c]pyrrole-1-carboxylic acid was used in place of (1S,3aR,6aS)-2-(4-(difluoromethoxy)-1H-indole-2-carbonyl)octahydrocyclopenta[c]pyrrole-1-carboxylic acid in Step 7.

Characterization data for Ex13 was obtained: ESI MS m/z=470.1 [M+H]+.

Ex14: Synthesis of (1S,3aR,6aS)-2-(4-chloro-1H-indole-2-carbonyl)-N—((S)-1-cyano-2-((S)-2-oxopyrrolidin-3-yl)ethyl)octahydrocyclopenta[c]pyrrole-1-carboxamide

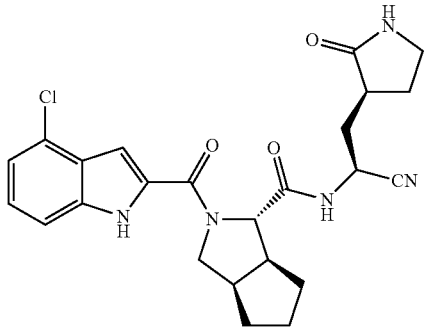 [SMILES: N#C[C@H](C[C@@H]1CCNC1=O)NC(=O)[C@@H]1[C@H]2CCC[C@H]2CN1C(=O)c1cc2c(Cl)cccc2[nH]1]

The synthesis of Ex14 was of a similar nature as the synthesis of Ex3, with the following changes:

1. (1S,3aR,6aS)-2-(4-chloro-1H-indole-2-carbonyl)octahydrocyclopenta[c]pyrrole-1-carboxylic acid was used in place of (1S,3aR,6aS)-2-(4-(difluoromethoxy)-1H-indole-2-carbonyl)octahydrocyclopenta[c]pyrrole-1-carboxylic acid in Step 7.

Characterization data for Ex14 was obtained: ESI MS m/z=469.1 [M+H]+.

Ex15: Synthesis of (1S,3aR,6aS)—N—((S)-4-(benzylamino)-3,4-dioxo-1-((S)-2-oxopyrrolidin-3-yl)butan-2-yl)-2-(4-(difluoromethoxy)-1H-indole-2-carbonyl)octahydrocyclopenta[c]pyrrole-1-carboxamide

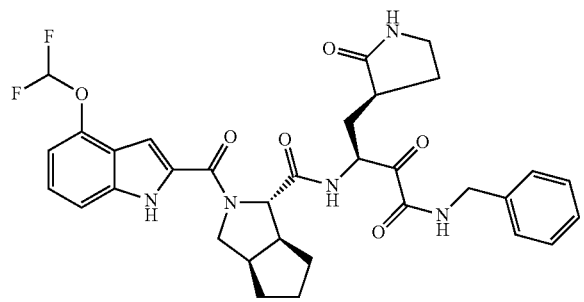 [SMILES: O=C(NCc1ccccc1)C(=O)[C@H](C[C@@H]1CCNC1=O)NC(=O)[C@@H]1[C@H]2CCC[C@H]2CN1C(=O)c1cc2c(OC(F)F)cccc2[nH]1]

The synthesis of Ex15 was of a similar nature as the synthesis of Ex8, with the following changes:
1. (isocyanomethyl)benzene was used in place of isocyanocyclohexane in Step 1.

Characterization data for Ex15 was obtained: ESI MS m/z=636.1 [M+H]$^+$.

Ex16: Synthesis of (1R,2S,5S)—N—((S)-1-cyano-2-((S)-2-oxopyrrolidin-3-yl)ethyl)-3-(5,7-difluoro-1H-indole-2-carbonyl)-6,6-dimethyl-3-azabicyclo[3.1.0]hexane-2-carboxamide

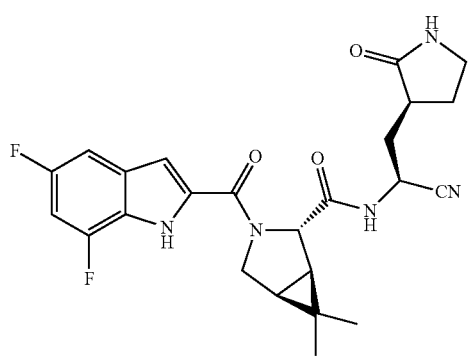 [SMILES: CC1(C)[C@@H]2[C@@H](C(=O)N[C@H](C#N)C[C@@H]3CCNC3=O)N(C(=O)c3cc4cc(F)cc(F)c4[nH]3)C[C@@H]21]

The synthesis of Ex16 was of a similar nature as the synthesis of Ex3, with the following changes:
1. 5,7-difluoro-1H-indole-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex16 was obtained: ESI MS m/z=470.1 [M+H]$^+$.

Ex17: Synthesis of (1R,2S,5S)—N—((S)-1-cyano-2-((S)-2-oxopyrrolidin-3-yl)ethyl)-3-(5,6-difluoro-1H-indole-2-carbonyl)-6,6-dimethyl-3-azabicyclo[3.1.0]hexane-2-carboxamide

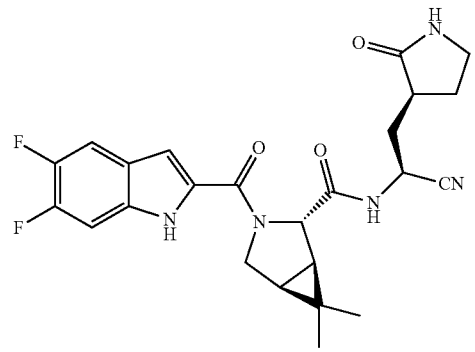 [SMILES: CC1(C)[C@@H]2[C@@H](C(=O)N[C@H](C#N)C[C@@H]3CCNC3=O)N(C(=O)c3cc4cc(F)c(F)cc4[nH]3)C[C@@H]21]

The synthesis of Ex17 was of a similar nature as the synthesis of Ex3, with the following changes:
1. 5,6-difluoro-1H-indole-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex17 was obtained: ESI MS m/z=470.1 [M+H]$^+$.

Ex18: Synthesis of (1R,2S,5S)—N—((S)-1-cyano-2-((S)-2-oxopyrrolidin-3-yl)ethyl)-3-(4,6-difluoro-1H-indole-2-carbonyl)-6,6-dimethyl-3-azabicyclo[3.1.0]hexane-2-carboxamide

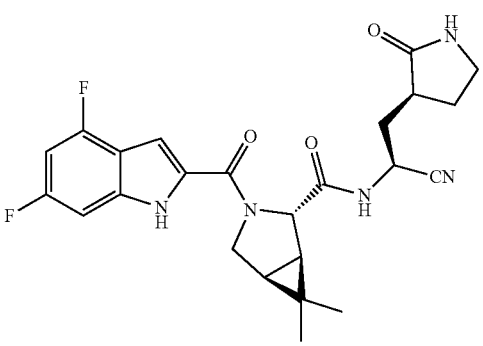 [SMILES: CC1(C)[C@@H]2[C@@H](C(=O)N[C@H](C#N)C[C@@H]3CCNC3=O)N(C(=O)c3cc4c(F)cc(F)cc4[nH]3)C[C@@H]21]

The synthesis of Ex18 was of a similar nature as the synthesis of Ex3, with the following changes:
1. 4,6-difluoro-1H-indole-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex18 was obtained: ESI MS m/z=470.1 [M+H]$^+$.

Ex19: Synthesis of (2S,4S)—N—((S)-1-cyano-2-((S)-2-oxopyrrolidin-3-yl)ethyl)-1-(4-(difluoromethoxy)-1H-indole-2-carbonyl)-4-phenoxypyrrolidine-2-carboxamide

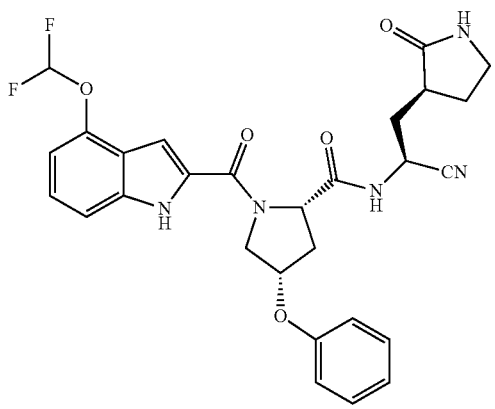 [SMILES: N#C[C@H](C[C@@H]1CCNC1=O)NC(=O)[C@@H]1C[C@H](Oc2ccccc2)CN1C(=O)c1cc2c(OC(F)F)cccc2[nH]1]

The synthesis of Ex19 was of a similar nature as the synthesis of Ex3, with the following changes:
1. ethyl (2S,4S)-4-phenoxypyrrolidine-2-carboxylate hydrochloride was used in place of Ethyl (1S,3aR,6aS)-octahydrocyclopenta[c]pyrrole-1-carboxylate hydrochloride in Step 5.

Characterization data for Ex19 was obtained: ESI MS m/z=552.1 [M+H]+.

Ex20: Synthesis of (1R,2S,5S)—N—((S)-1-cyano-2-((S)-2-oxopyrrolidin-3-yl)ethyl)-3-(4,7-difluoro-1H-indole-2-carbonyl)-6,6-dimethyl-3-azabicyclo[3.1.0]hexane-2-carboxamide

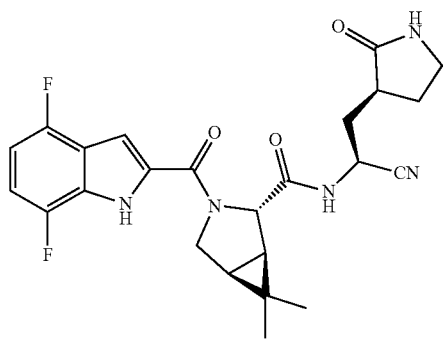 [SMILES: CC1(C)[C@@H]2[C@@H](C(=O)N[C@H](C#N)C[C@@H]3CCNC3=O)N(C(=O)c3cc4c(F)ccc(F)c4[nH]3)C[C@@H]21]

The synthesis of Ex20 was of a similar nature as the synthesis of Ex3, with the following changes:
1. 4,7-difluoro-1H-indole-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex20 was obtained: ESI MS m/z=470.1 [M+H]+.

Ex21: Synthesis of (1R,2S,5S)-3-(4-chloro-1H-indole-2-carbonyl)-N—((S)-1-cyano-2-((S)-2-oxopyrrolidin-3-yl)ethyl)-6,6-dimethyl-3-azabicyclo[3.1.0]hexane-2-carboxamide

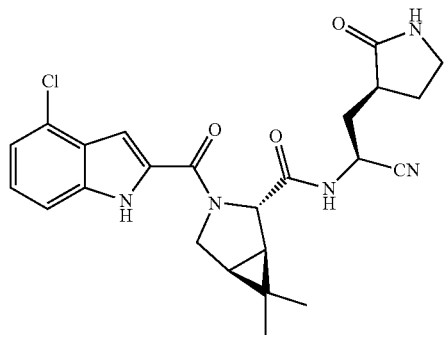 [SMILES: CC1(C)[C@@H]2[C@@H](C(=O)N[C@H](C#N)C[C@@H]3CCNC3=O)N(C(=O)c3cc4c(Cl)cccc4[nH]3)C[C@@H]21]

The synthesis of Ex21 was of a similar nature as the synthesis of Ex3, with the following changes:
1. 4-chloro-1H-indole-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex21 was obtained: ESI MS m/z=469.1 [M+H]+.

Ex22: Synthesis of (1R,2S,5S)-3-(4-chlorobenzofuran-2-carbonyl)-N—((S)-1-cyano-2-((S)-2-oxopyrrolidin-3-yl)ethyl)-6,6-dimethyl-3-azabicyclo[3.1.0]hexane-2-carboxamide

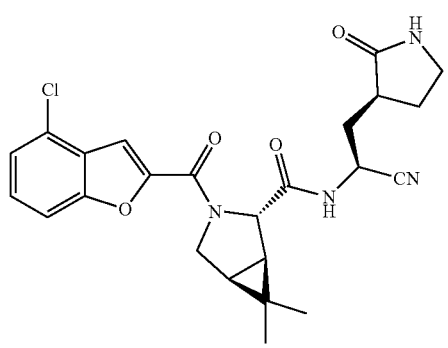 [SMILES: CC1(C)[C@@H]2[C@@H](C(=O)N[C@H](C#N)C[C@@H]3CCNC3=O)N(C(=O)c3cc4c(Cl)cccc4o3)C[C@@H]21]

The synthesis of Ex22 was of a similar nature as the synthesis of Ex3, with the following changes:
1. 4-chlorobenzofuran-2-carboxylic acid was used in place of 4-(difluoromethoxy)-1H-indole-2-carboxylic acid in Step 4.
2. ethyl (1R,2S,5S)-6,6-dimethyl-3-azabicyclo[3.1.0]hexane-2-carboxylate hydrochloride was used in place of Ethyl (1S,3aR,6aS)-octahydrocyclopenta[c]pyrrole-1-carboxylate hydrochloride in Step 5.

Characterization data for Ex22 was obtained: ESI MS m/z=470.1 [M+H]+.

Ex23: Synthesis of (1R,2S,5S)—N—((S)-1-cyano-2-((S)-2-oxopyrrolidin-3-yl)ethyl)-3-((S)-2-(cyclopentanecarboxamido)-3,3-dimethylbutanoyl)-6,6-dimethyl-3-azabicyclo[3.1.0]hexane-2-carboxamide

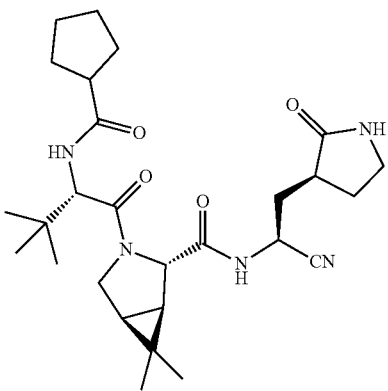 [SMILES: CC(C)(C)[C@H](NC(=O)C1CCCC1)C(=O)N1C[C@H]2[C@@H]([C@H]1C(=O)N[C@H](C#N)C[C@@H]1CCNC1=O)C2(C)C]

Step 1: A vial was charged with Boc-L-tert-leucine (1.55 g), DCM (20 mL), and DMF (5 mL). The vial was cooled to 0° C. then HATU (2.2 g) was added. Then Hunig's base (1.8 g) was added. The yellow suspension was stirred for 2 min then methyl (1R,2S,5S)-6,6-dimethyl-3-azabicyclo[3.1.0]hexane-2-carboxylate hydrochloride was added. Then Hunig's base (1.8 g) was added and the reaction was allowed to reach room temperature. After 2 h, the reaction mixture was diluted with ethyl acetate and partitioned with water. The product was extracted with ethyl acetate. The combined organics were concentrated and the residue was purified on silica gel to provide the product, methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate (1.5 g). ESI MS m/z=383.1 [M+H]$^+$.

Step 2: A vial was charged with methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate (300 mg) and MeOH (4 mL). The vial was cooled to 0° C. then 2.5 M aq. LiOH (2 mL) was added. After 3.5 h, the reaction mixture was concentrated. Then, 4 M HCl in dioxanes (5.5 mL) was added and the reaction mixture was stirred for 1 h. Then the reaction mixture was concentrated, to provide the product, (1R,2S,5S)-3-((S)-2-amino-3,3-dimethylbutanoyl)-6,6-dimethyl-3-azabicyclo[3.1.0]hexane-2-carboxylic acid, which was used in crude form without further purification. ESI MS m/z=269.1 [M+H]$^+$.

Step 3: A vial was charged with (1R,2S,5S)-3-((S)-2-amino-3,3-dimethylbutanoyl)-6,6-dimethyl-3-azabicyclo[3.1.0]hexane-2-carboxylic acid (304 mg), triethylamine (0.42 mL), and MeCN (6 mL). The vial was stirred at 0° C., then cyclopentanecarbonyl chloride (147 mg) was added dropwise under a nitrogen atmosphere. After 1 h, DCM (25 mL) was added. The reaction mixture was partitioned with water (25 mL) and stirred at room temperature. After 10 min, the organic layer was removed. The aqueous layer was acidified to pH 5 with 1 M Aq. HCl. The product was extracted with ethyl acetate, dried over sodium sulfate, filtered, and concentrated. The product, (1R,2S,5S)-3-((S)-2-(cyclopentanecarboxamido)-3,3-dimethylbutanoyl)-6,6-dimethyl-3-azabicyclo[3.1.0]hexane-2-carboxylic acid, was used in crude form without further purification. ESI MS m/z=365.1 [M+H]$^+$.

Step 4: A vial was charged with (1R,2S,5S)-3-((S)-2-(cyclopentanecarboxamido)-3,3-dimethylbutanoyl)-6,6-dimethyl-3-azabicyclo[3.1.0]hexane-2-carboxylic acid (130 mg) and DMF (5 mL). DIEA (139 mg) was then added. HATU (274 mg) was then added at room temperature and the reaction mixture was stirred for 10 min. Then, tert-butyl ((S)-1-cyano-2-((S)-2-oxopyrrolidin-3-yl)ethyl)carbamate (155 mg) was added. After 1 h, the reaction mixture was poured into water and extracted with ethyl acetate. The combined organic layers were washed with brine, dried over sodium sulfate, filtered, and concentrated. The residue was purified by RPHPLC to provide the product, (1R,2S,5S)—N—((S)-1-cyano-2-((S)-2-oxopyrrolidin-3-yl)ethyl)-3-((S)-2-(cyclopentanecarboxamido)-3,3-dimethylbutanoyl)-6,6-dimethyl-3-azabicyclo[3.1.0]hexane-2-carboxamide (45 mg). ESI MS m/z=500.1 [M+H]$^+$. 1H NMR (300 MHz, DMSO-d$_6$) δ 8.96 (d, J=8.5 Hz, 1H), 7.76 (d, J=9.2 Hz, 1H), 7.66 (s, 1H), 5.04-4.89 (m, 1H), 4.38 (d, J=9.2 Hz, 1H), 4.12 (s, 1H), 3.91-3.76 (m, 2H), 3.20-2.98 (m, 2H), 2.82-2.66 (m, 1H), 2.47-2.37 (m, 1H), 2.23-2.01 (m, 2H), 1.76-1.42 (m, 11H), 1.28 (d, J=7.6 Hz, 1H), 1.02 (s, 3H), 0.94 (s, 9H), 0.82 (s, 3H).

Ex24: Synthesis of (1R,2S,5S)—N—((S)-1-cyano-2-((S)-2-oxopyrrolidin-3-yl)ethyl)-3-((S)-3,3-dimethyl-2-(2-phenylacetamido)butanoyl)-6,6-dimethyl-3-azabicyclo[3.1.0]hexane-2-carboxamide

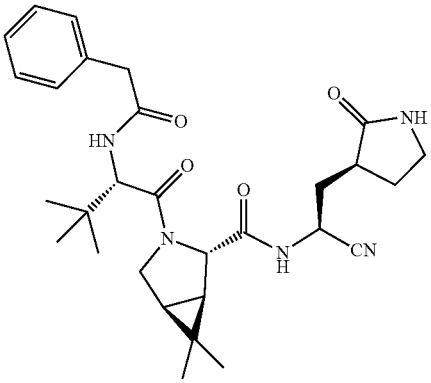 [SMILES: CC(C)(C)[C@H](NC(=O)Cc1ccccc1)C(=O)N1C[C@H]2[C@@H]([C@H]1C(=O)N[C@H](C#N)C[C@@H]1CCNC1=O)C2(C)C]

The synthesis of Ex24 was of a similar nature as the synthesis of Ex23, with the following changes:
1. 2-phenylacetyl chloride was used in place of cyclopentanecarbonyl chloride in Step 3.

Characterization data for Ex24 was obtained: ESI MS m/z=522.1 [M+H]$^+$. 1H NMR (300 MHz, DMSO-d$_6$) δ 8.97 (d, J=8.6 Hz, 1H), 8.13 (d, J=9.0 Hz, 1H), 7.66 (s, 1H), 7.30-7.14 (m, 6H), 5.03-4.88 (m, 1H), 4.36 (d, J=6.0 Hz, 1H), 4.11 (s, 1H), 3.90-3.81 (m, 1H), 3.74 (d, J=10.4 Hz, 1H), 3.56-3.41 (m, 2H), 3.19-2.99 (m, 2H), 2.27-1.99 (m, 3H), 1.77-1.63 (m, 2H), 1.54-1.48 (m, 1H), 1.27 (d, J=7.6 Hz, 1H), 1.01 (s, 3H), 0.91 (s, 9H), 0.74 (s, 3H).

Ex25: Synthesis of (1R,2S,5S)—N—((S)-1-cyano-2-((S)-2-oxopyrrolidin-3-yl)ethyl)-3-((S)-2-(cyclohexanecarboxamido)-3,3-dimethylbutanoyl)-6,6-dimethyl-3-azabicyclo[3.1.0]hexane-2-carboxamide

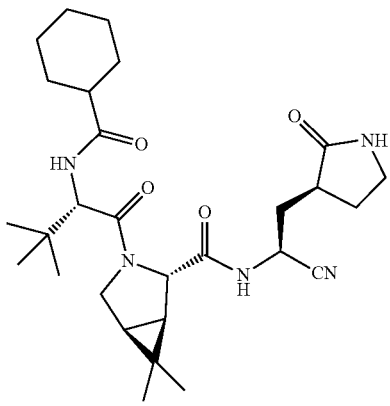 [SMILES: CC(C)(C)[C@H](NC(=O)C1CCCCC1)C(=O)N1C[C@H]2[C@@H]([C@H]1C(=O)N[C@H](C#N)C[C@@H]1CCNC1=O)C2(C)C]

The synthesis of Ex25 was of a similar nature as the synthesis of Ex23, with the following changes:
1. cyclohexanecarbonyl chloride was used in place of cyclopentanecarbonyl chloride in Step 3.

Characterization data for Ex25 was obtained: ESI MS m/z=514.1 [M+H]$^+$. 1H NMR (300 MHz, DMSO-d$_6$) δ 8.95 (d, J=8.5 Hz, 1H), 7.73-7.62 (m, 2H), 5.00-4.90 (m, 1H), 4.35 (d, J=9.2 Hz, 1H), 4.11 (s, 1H), 3.90-3.77 (m, 4H), 3.19-2.99 (m, 2H), 2.45-2.24 (m, 2H), 2.22-2.00 (m, 2H), 1.75-1.47 (m, 8H), 1.24-1.10 (m, 4H), 1.01 (s, 3H), 0.93 (s, 9H), 0.82 (s, 3H).

Ex26: Synthesis of (1R,2S,5S)—N—((S)-1-cyano-2-((S)-2-oxopyrrolidin-3-yl)ethyl)-3-((S)-3,3-dimethyl-2-propionamidobutanoyl)-6,6-dimethyl-3-azabicyclo[3.1.0]hexane-2-carboxamide

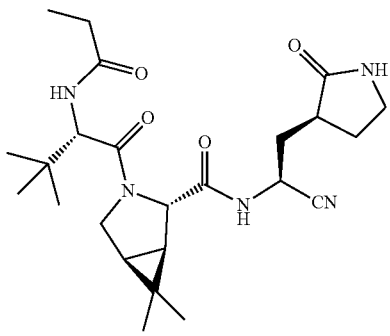 [SMILES: CCC(=O)N[C@H](C(=O)N1C[C@H]2[C@@H]([C@H]1C(=O)N[C@H](C#N)C[C@@H]1CCNC1=O)C2(C)C)C(C)(C)C]

The synthesis of Ex26 was of a similar nature as the synthesis of Ex23, with the following changes:
1. propionyl chloride was used in place of cyclopentanecarbonyl chloride in Step 3.

Characterization data for Ex26 was obtained: ESI MS m/z=460.1 [M+H]$^+$. 1H NMR (300 MHz, DMSO-d$_6$) δ 8.96 (d, J=8.6 Hz, 1H), 7.79 (d, J=8.9 Hz, 1H), 7.65 (s, 1H), 5.01-4.90 (m, 1H), 4.34 (d, J=9.0 Hz, 1H), 4.11 (s, 1H), 3.89-3.76 (m, 2H), 3.08 (dq, J=16.4, 9.4 Hz, 2H), 2.45-2.35 (m, 1H), 2.19-2.01 (m, 4H), 1.78-1.63 (m, 2H), 1.58-1.50 (m, 1H), 1.28 (d, J=7.7 Hz, 1H), 1.02 (s, 3H), 0.94 (t, J=6.0 Hz, 1H), 0.92 (s, 9H), 0.84 (s, 3H).

Ex27: Synthesis of (1R,2S,5S)—N—((S)-1-cyano-2-((S)-2-oxopyrrolidin-3-yl)ethyl)-3-((S)-2-isobutyramido-3,3-dimethylbutanoyl)-6,6-dimethyl-3-azabicyclo[3.1.0]hexane-2-carboxamide

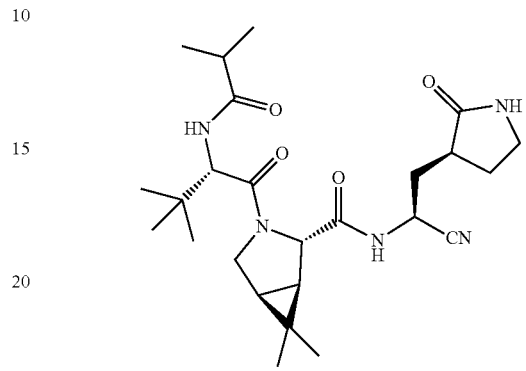

The synthesis of Ex27 was of a similar nature as the synthesis of Ex23, with the following changes:
1. isobutyryl chloride was used in place of cyclopentanecarbonyl chloride in Step 3.

Characterization data for Ex27 was obtained: ESI MS m/z=474.1 [M+H]$^+$. 1H NMR (300 MHz, DMSO-d$_6$) δ 8.95 (d, J=8.5 Hz, 1H), 7.76 (d, J=9.2 Hz, 1H), 7.65 (s, 1H), 5.01-4.89 (m, 1H), 4.39 (d, J=9.2 Hz, 1H), 4.12 (s, 1H), 3.91-3.75 (m, 2H), 3.20-2.97 (m, 2H), 2.58 (dd, J=13.6, 6.8 Hz, 1H), 2.46-2.36 (m, 1H), 2.23-2.02 (m, 2H), 1.78-1.63 (m, 2H), 1.56-1.49 (m, 1H), 1.28 (d, J=7.6 Hz, 1H), 1.02 (s, 3H), 1.00-0.85 (m, 15H), 0.82 (s, 3H).

Ex28: Synthesis of (1R,2S,5S)—N—((S)-1-cyano-2-((S)-2-oxopyrrolidin-3-yl)ethyl)-3-((S)-3,3-dimethyl-2-pivalamidobutanoyl)-6,6-dimethyl-3-azabicyclo[3.1.0]hexane-2-carboxamide

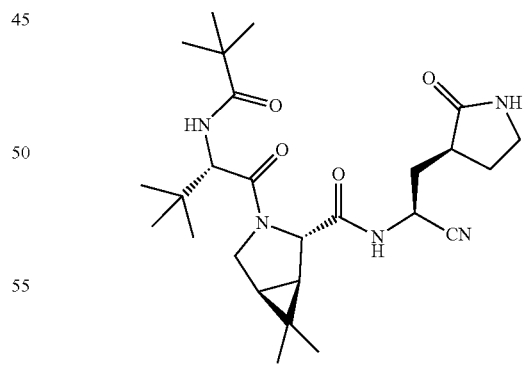

The synthesis of Ex28 was of a similar nature as the synthesis of Ex23, with the following changes:
1. pivaloyl chloride was used in place of cyclopentanecarbonyl chloride in Step 3.

Characterization data for Ex28 was obtained: ESI MS m/z=488.1 [M+H]$^+$. 1H NMR (300 MHz, DMSO-d$_6$) δ 8.95 (d, J=8.5 Hz, 1H), 7.67 (s, 1H), 6.88 (d, J=7.3 Hz, 1H), 5.02-4.89 (m, 1H), 4.46 (s, 1H), 4.13 (s, 1H), 3.93-3.81 (m, 1H), 3.73 (d, J=10.3 Hz, 1H), 3.21-2.98 (m, 2H), 2.45-2.36 (m, 1H), 2.19-2.04 (m, 2H), 1.79-1.63 (m, 2H), 1.58-1.49 (m, 1H), 1.29 (d, J=7.6 Hz, 1H), 1.08 (s, 9H), 1.02 (s, 3H), 0.92 (s, 9H), 0.81 (s, 3H).

Ex29: Synthesis of (1R,2S,5S)-3-((S)-2-acetamido-3,3-dimethylbutanoyl)-N—((S)-1-cyano-2-((S)-2-oxopyrrolidin-3-yl)ethyl)-6,6-dimethyl-3-azabicyclo[3.1.0]hexane-2-carboxamide

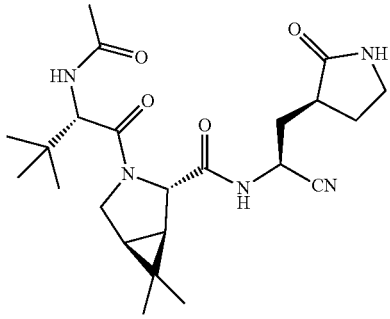 [SMILES: CC(=O)N[C@H](C(=O)N1C[C@H]2[C@@H]([C@H]1C(=O)N[C@H](C#N)C[C@@H]1CCNC1=O)C2(C)C)C(C)(C)C]

The synthesis of Ex29 was of a similar nature as the synthesis of Ex23, with the following changes:
1. acetyl chloride was used in place of cyclopentanecarbonyl chloride in Step 3.

Characterization data for Ex29 was obtained: ESI MS m/z=446.1 [M+H]$^+$. 1H NMR (300 MHz, DMSO-d$_6$) δ 8.97 (d, J=8.6 Hz, 1H), 7.87 (d, J=8.7 Hz, 1H), 7.65 (brs, 1H), 4.99-4.92 (m, 1H), 4.30 (d, J=8.7 Hz, 1H), 4.11 (s, 1H), 3.90-3.75 (m, 2H), 3.18-2.99 (m, 2H), 2.45-2.35 (m, 1H), 2.20-1.98 (m, 2H), 1.83 (s, 3H), 1.79-1.62 (m, 2H), 1.57-1.50 (m, 1H), 1.28 (d, J=7.7 Hz, 1H), 1.02 (s, 3H), 0.94 (s, 9H), 0.86 (s, 3H).

Biological Activity

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 µL of test compound was dissolved in DMSO then incubated with SARS-CoV-2 3CL-protease (10 nM) in 10 µL assay buffer (50 mM HEPES [pH 7.5], 1 mM DTT, 0.01% BSA, 0.01% Triton-X 100) for 30 min at RT. Next, 10 µL of 3CL-protease substrate (40 µM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate.

Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 µM). Data were fitted to normalized activity (variable slope) versus concentration fit in GraphPad Prism 7 to determine IC$_{50}$. All experiments were run in duplicate, and IC$_{50}$ ranges are reported as follows: A<0.1 µM; B 0.1-1 µM; C>1 µM.

TABLE 7

Summary of Activities

| Example Number | FRET IC$_{50}$ |
|---|---|
| 1 | B |
| 2 | A |
| 3 | B |
| 4 | B |
| 5 | A |
| 6 | A |
| 7 | A |
| 8 | A |
| 9 | A |
| 10 | B |
| 11 | B |
| 12 | C |
| 13 | B |
| 14 | B |
| 15 | A |
| 16 | B |
| 17 | B |
| 18 | B |
| 19 | C |
| 20 | B |
| 21 | B |
| 22 | C |
| 23 | A |
| 24 | A |
| 25 | A |
| 26 | A |
| 27 | A |
| 28 | A |
| 29 | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (VI-6a),

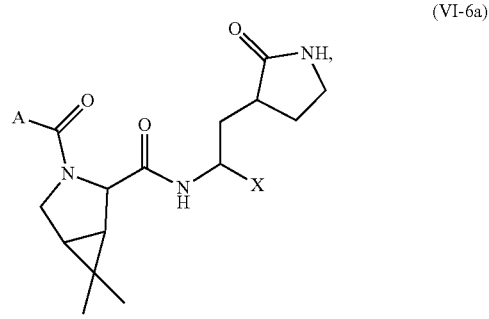

(VI-6a)

or a pharmaceutically acceptable salt thereof, wherein
X is —CN; and
A is optionally substituted C$_1$-C$_8$ alkyl or optionally substituted heteroaryl.

2. The compound of claim 1 wherein A is optionally substituted C$_1$-C$_8$ alkyl.

3. The compound of claim 1 wherein A is optionally substituted heteroaryl.

4. The compound of claim 1 wherein A is selected from the group consisting of

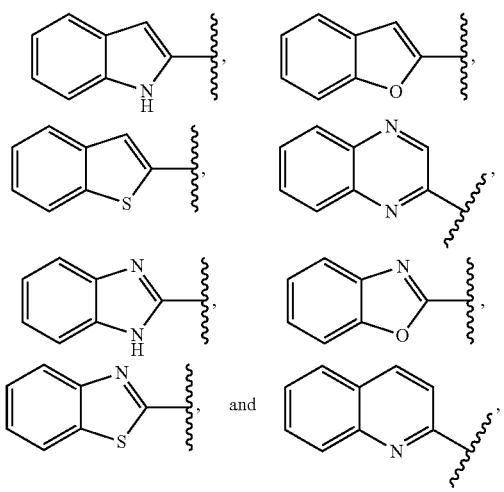

each of which is optionally substituted.

5. The compound of claim 1 which is represented by Formula (X-e),

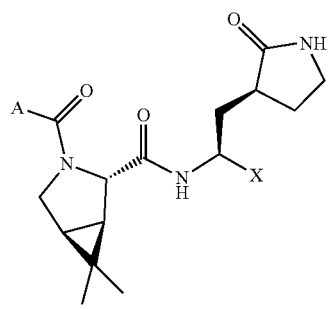

(X-e)

or a pharmaceutically acceptable salt thereof, wherein A and X are as defined in claim 1.

6. The compound of claim 5 wherein A is selected from the group consisting of

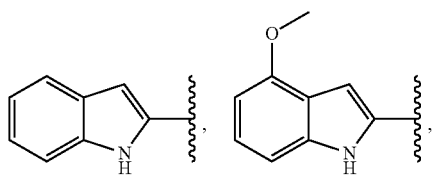

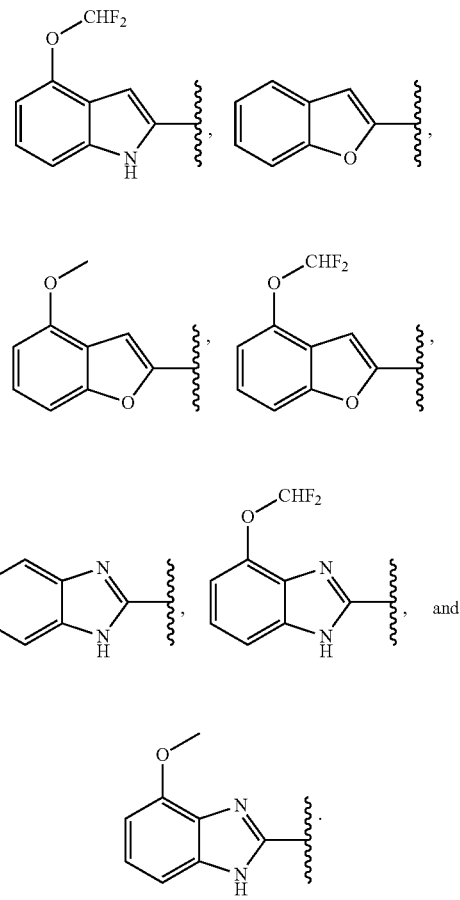

7. A pharmaceutical composition comprising the compound of claim 1 and a pharmaceutically acceptable carrier or excipient.

8. A method of treating a coronavirus infection in a subject in need thereof, comprising administering to the subject a therapeutically effective amount of the compound of claim 1.

9. The compound of claim 5 wherein A is optionally substituted $C_1$-$C_8$ alkyl.

10. A method of treating a coronavirus infection in a subject in need thereof, comprising administering to the subject a therapeutically effective amount of the compound of claim 2.

\* \* \* \* \*